US009664486B2

(12) United States Patent
Scott et al.

(10) Patent No.: US 9,664,486 B2
(45) Date of Patent: May 30, 2017

(54) REMOTE TREATMENT SYSTEM

(71) Applicant: COOLGARDIE, LLC, Austin, TX (US)

(72) Inventors: Alastair Gordon Scott, Riederau am Ammersee (DE); Andrew Haywood Smith, Bramford (GB)

(73) Assignee: Coolgardie LLC, Austin, TX (US)

( * ) Notice: Subject to any disclaimer, the term of this patent is extended or adjusted under 35 U.S.C. 154(b) by 0 days.

(21) Appl. No.: 14/844,611

(22) Filed: Sep. 3, 2015

(65) Prior Publication Data

US 2016/0015499 A1 Jan. 21, 2016

Related U.S. Application Data

(63) Continuation-in-part of application No. PCT/US2014/027445, filed on Mar. 14, 2014, and a
(Continued)

(51) Int. Cl.
*F42B 12/54* (2006.01)
*F42B 7/08* (2006.01)
(Continued)

(52) U.S. Cl.
CPC ............... *F42B 12/54* (2013.01); *A61D 7/00* (2013.01); *A61M 5/20* (2013.01); *F42B 7/08* (2013.01);
(Continued)

(58) Field of Classification Search
CPC .......... F42B 12/36; F42B 12/46; F42B 12/54; F42B 7/08; F42B 10/16; F42B 10/34;
(Continued)

(56) References Cited

U.S. PATENT DOCUMENTS 1,815,300 A * 7/1931 Harris ..................... F42B 12/54
102/512
1,819,415 A * 8/1931 Harris ..................... F42B 12/54
102/512
(Continued)

FOREIGN PATENT DOCUMENTS

DE 2260529 A1 6/1974
GB 2393236 A 3/2004
WO WO-2014/152532 A1 9/2014

OTHER PUBLICATIONS

International Search Report and Written Opinion for Application No. PCT/US2014/027445, dated Jul. 25, 2014.
(Continued)

*Primary Examiner* — James S Bergin
(74) *Attorney, Agent, or Firm* — Marshall, Gerstein & Borun LLP

(57) ABSTRACT

A remote treatment system may include a cone assembly including a spine and a cone body at least partially surrounding the spine, a marking payload, a syringe coupled to a portion of the cone assembly and adapted to store a syringe payload for treating a target, and a vanes cup. The vanes cup may have an inner diameter sized to receive an outer diameter of the syringe. The vanes cup may also include stabilization means for stabilizing the remote treatment system. Further, a pressure means within the vanes cup may be configured to apply a pressure against the payload within the syringe. In response to an impact between the cone assembly and the target, the payloads are expressed from the remote treatment system.

20 Claims, 49 Drawing Sheets

Related U.S. Application Data continuation-in-part of application No. 13/804,838, filed on Mar. 14, 2013, now Pat. No. 9,151,582, said application No. 14/844,611 is a continuation-in-part of application No. 13/804,838, filed on Mar. 14, 2013, now Pat. No. 9,151,582.

(60) Provisional application No. 62/195,710, filed on Jul. 22, 2015, provisional application No. 61/924,527, filed on Jan. 7, 2014.

(51) Int. Cl.
*A61D 7/00* (2006.01)
*A61M 5/20* (2006.01)
*F42B 10/16* (2006.01)
*F42B 10/34* (2006.01)
*F42B 12/34* (2006.01)
*F42B 12/36* (2006.01)

(52) U.S. Cl.
CPC .............. *F42B 10/16* (2013.01); *F42B 10/34* (2013.01); *F42B 12/34* (2013.01); *F42B 12/362* (2013.01)

(58) Field of Classification Search
CPC .......... F42B 12/34; F42B 12/362; A61D 7/00; A61M 5/20
USPC ................. 102/502, 512; 604/130, 93.01, 48
See application file for complete search history.

(56) References Cited

U.S. PATENT DOCUMENTS

| | | | |
|---|---|---|---|
| 3,022,785 A * | 2/1962 | Crockford | F42B 12/54 473/581 |
| RE25,279 E * | 10/1962 | Crockford et al. | F42B 12/54 102/512 |
| 3,093,077 A * | 6/1963 | Harris | F42B 12/54 102/512 |
| 3,207,157 A * | 9/1965 | Murdoch | A61M 5/2033 473/581 |
| 3,209,696 A * | 10/1965 | Palmer | F42B 12/54 102/512 |
| 3,396,660 A * | 8/1968 | Bilson | F42B 12/54 102/512 |
| 3,419,274 A * | 12/1968 | MacDonald | F42B 12/50 102/512 |
| 3,502,025 A | 3/1970 | Payne | |
| 3,584,582 A | 6/1971 | Muller | |
| 3,820,465 A | 6/1974 | Delphia | |
| 4,103,893 A * | 8/1978 | Walker | F42B 12/54 473/581 |
| 4,243,036 A | 1/1981 | Ott | |
| 4,735,612 A * | 4/1988 | Chevalier | F42B 12/54 102/512 |
| 4,863,428 A * | 9/1989 | Chevalier | F42B 12/54 102/512 |
| 5,318,576 A | 6/1994 | Plassche, Jr. et al. | |
| 6,605,059 B1 * | 8/2003 | Middleton | F42B 12/54 604/130 |
| 6,736,070 B2 | 5/2004 | Baltos | |
| 6,807,908 B2 | 10/2004 | Brydges-Price | |
| 7,013,810 B1 | 3/2006 | Brydges-Price | |
| 7,993,348 B2 | 8/2011 | Conte et al. | |
| 9,358,090 B2 * | 6/2016 | Taylor | F42B 12/54 |
| 2005/0107738 A1 | 5/2005 | Slater et al. | |
| 2014/0261045 A1 | 9/2014 | Scott | |
| 2016/0015499 A1 | 1/2016 | Scott et al. | |

OTHER PUBLICATIONS

Invitation to Pay Additional Fees with Communication Relating to Search Results in International Application No. PCT/US2016/043076 dated Oct. 27, 2016, 7 pages.

International Search Report and Written Opinion in International Application No. PCT/US2016/043076 dated Dec. 19, 2016, 17 pages.

\* cited by examiner

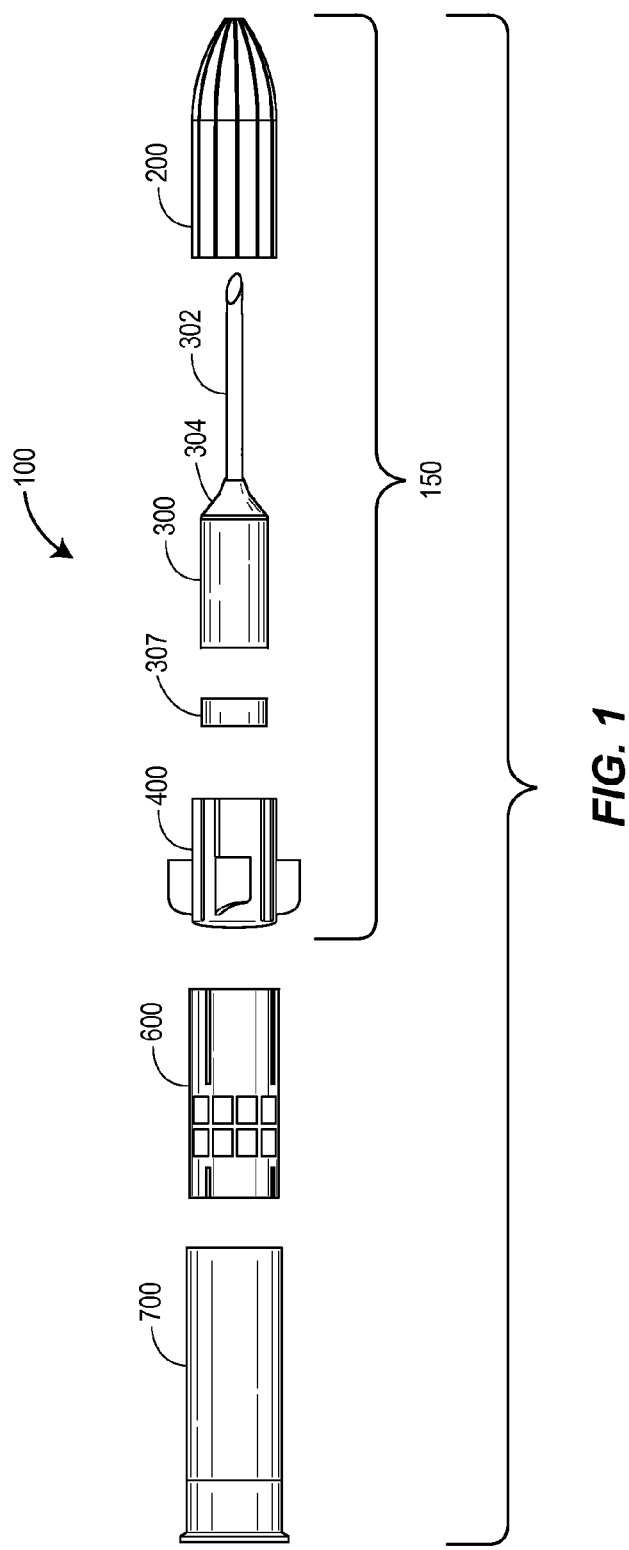

200

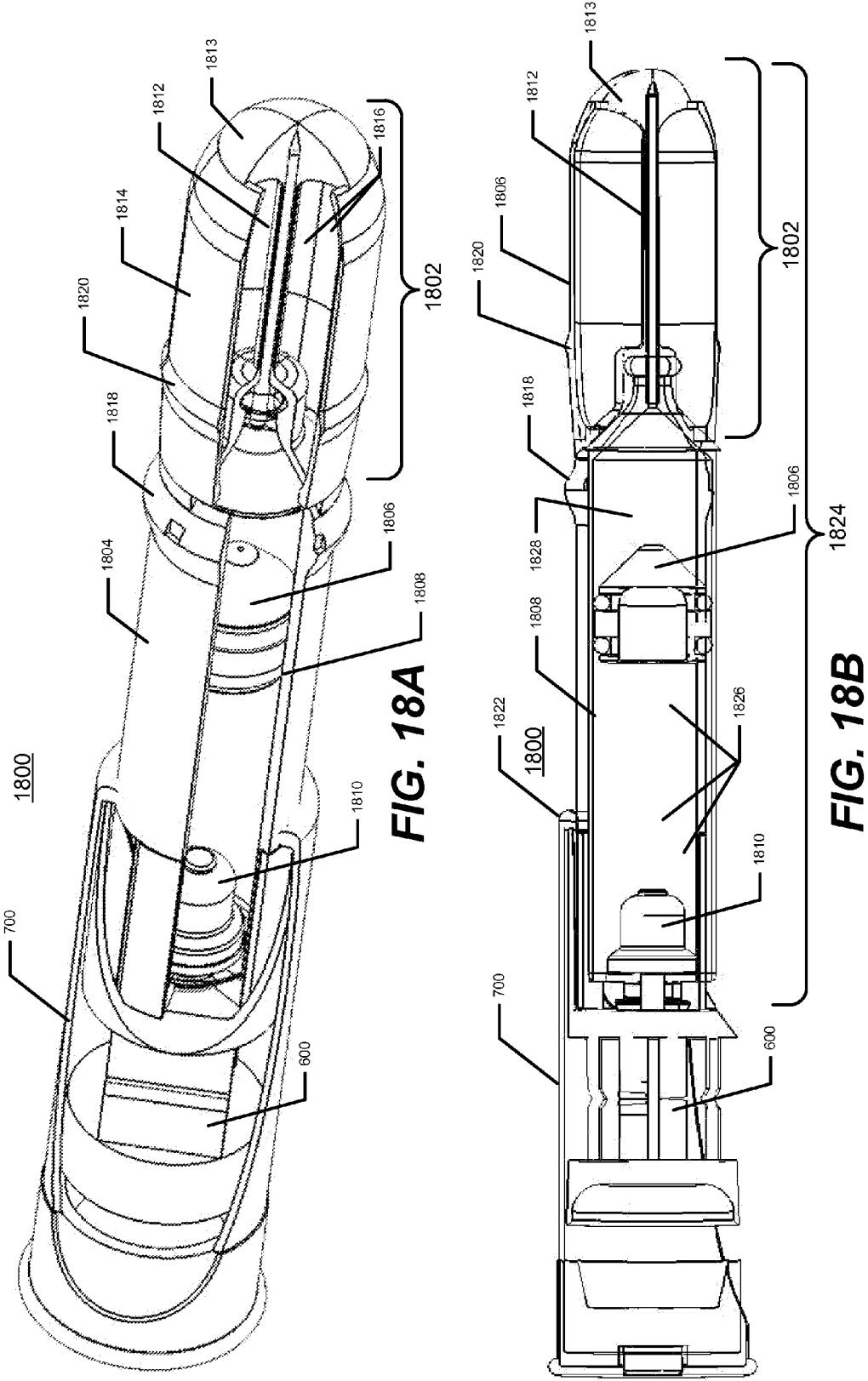

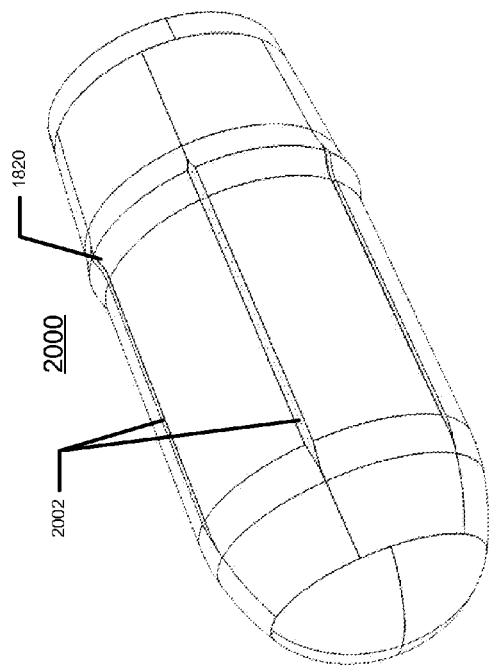
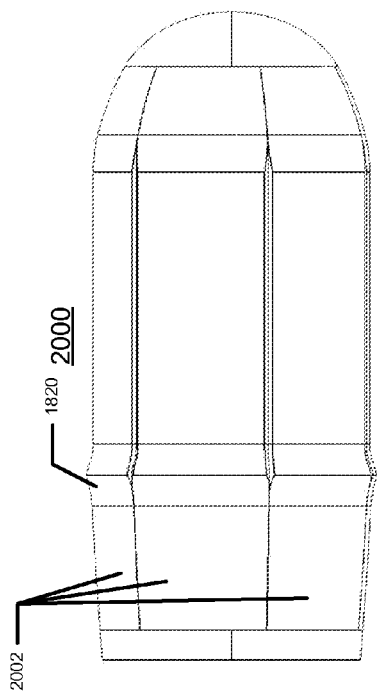
FIG. 20A
FIG. 20B
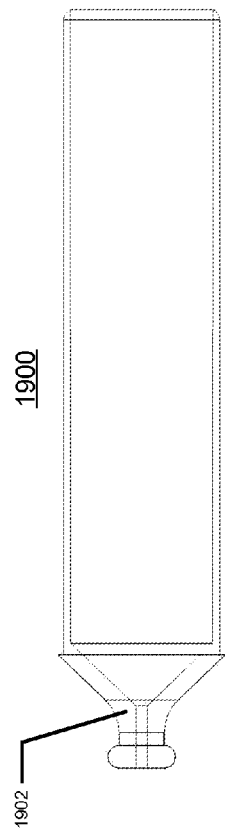
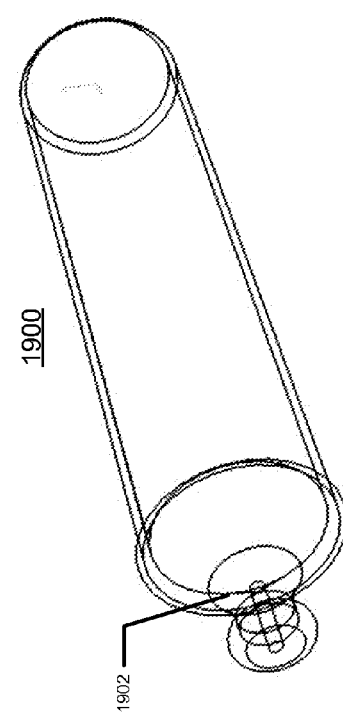
FIG. 19A
FIG. 19B
FIG. 19C

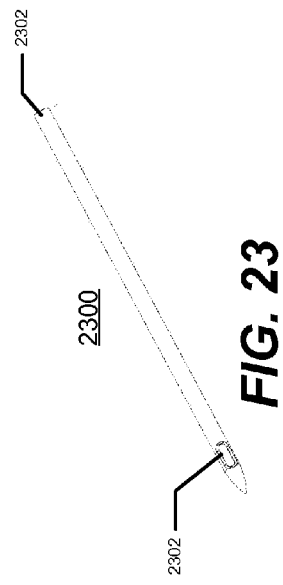
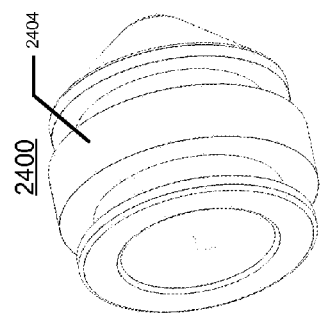
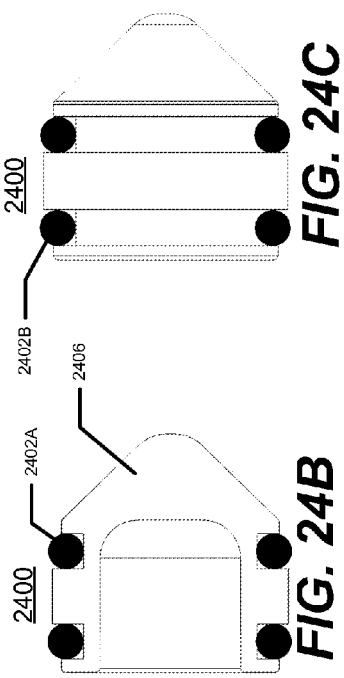
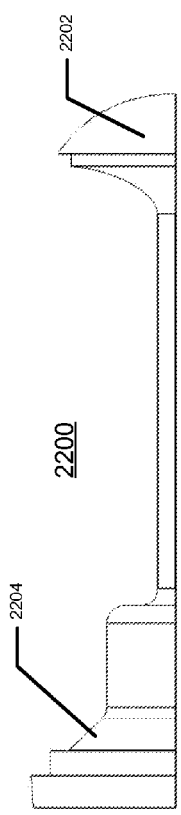
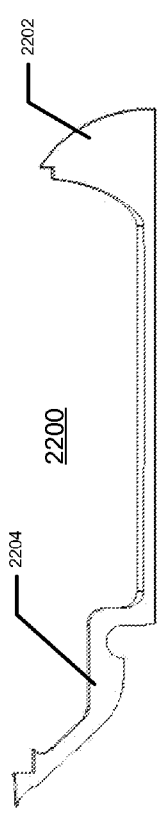
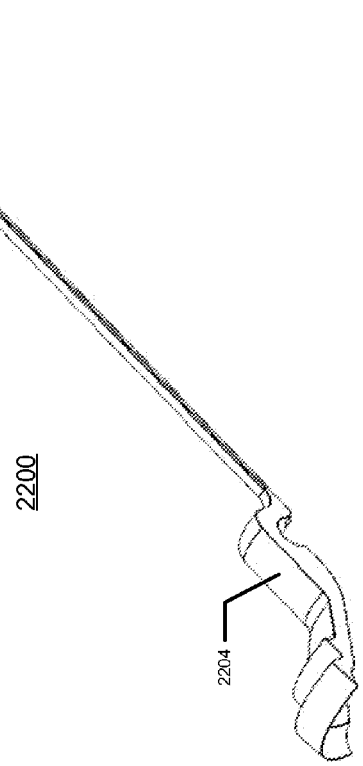

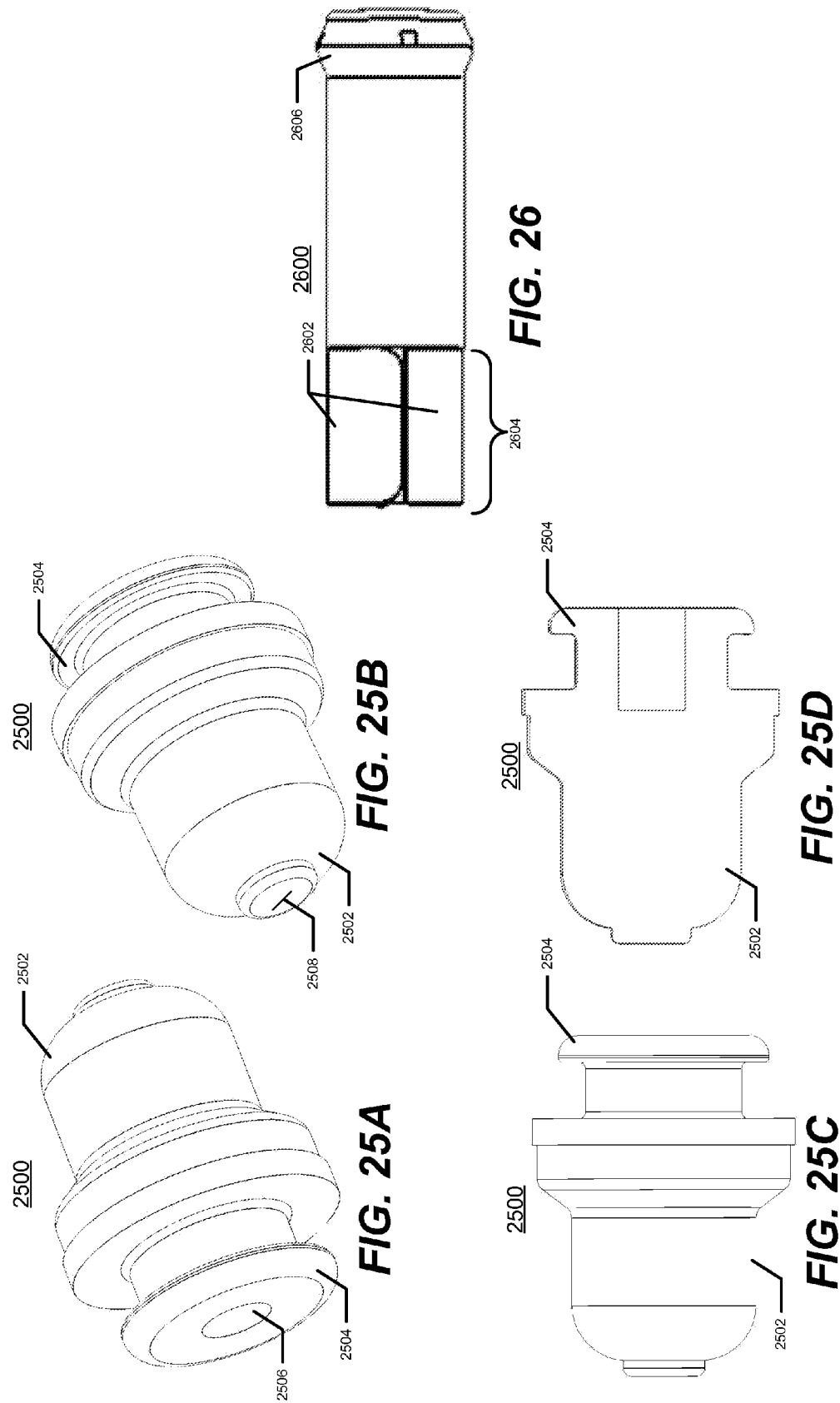

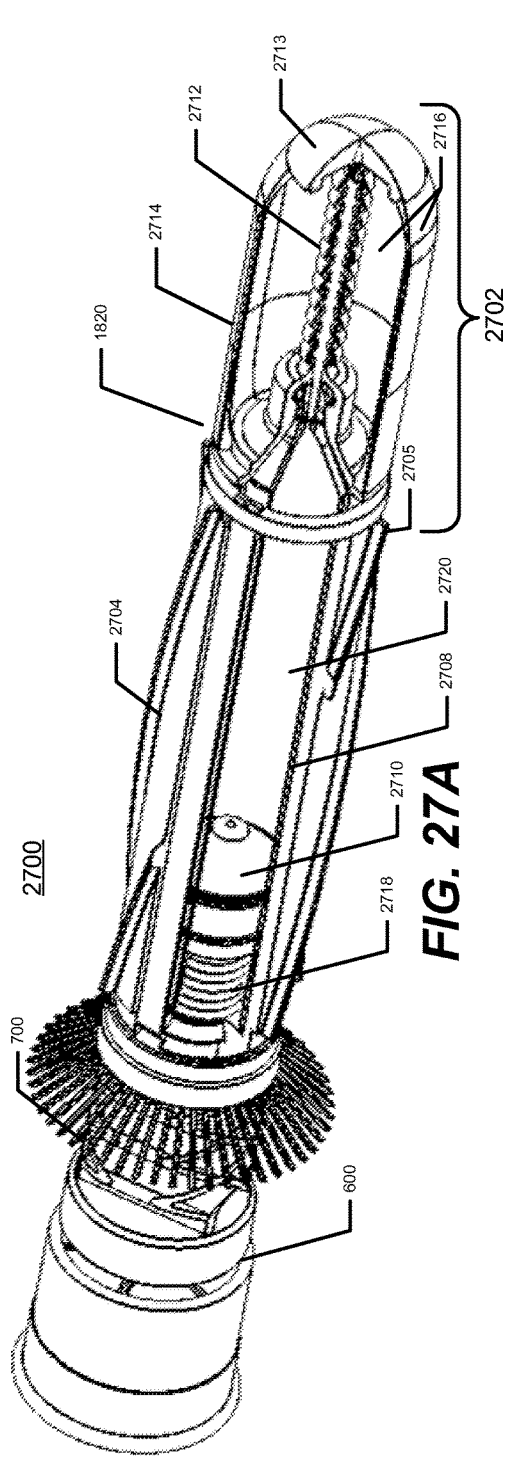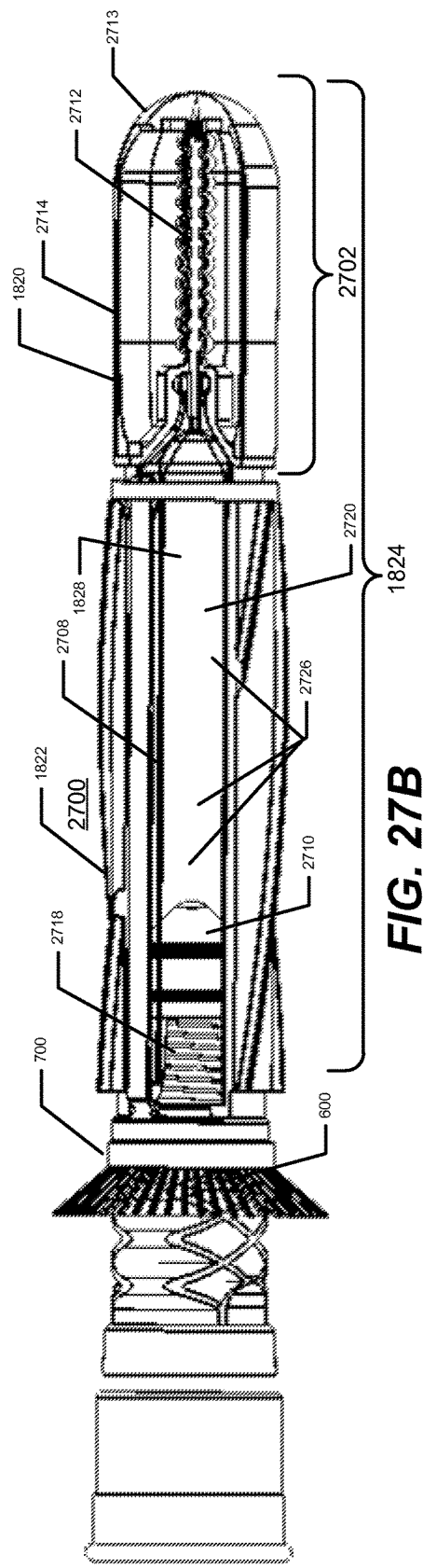
FIG. 27A
FIG. 27B

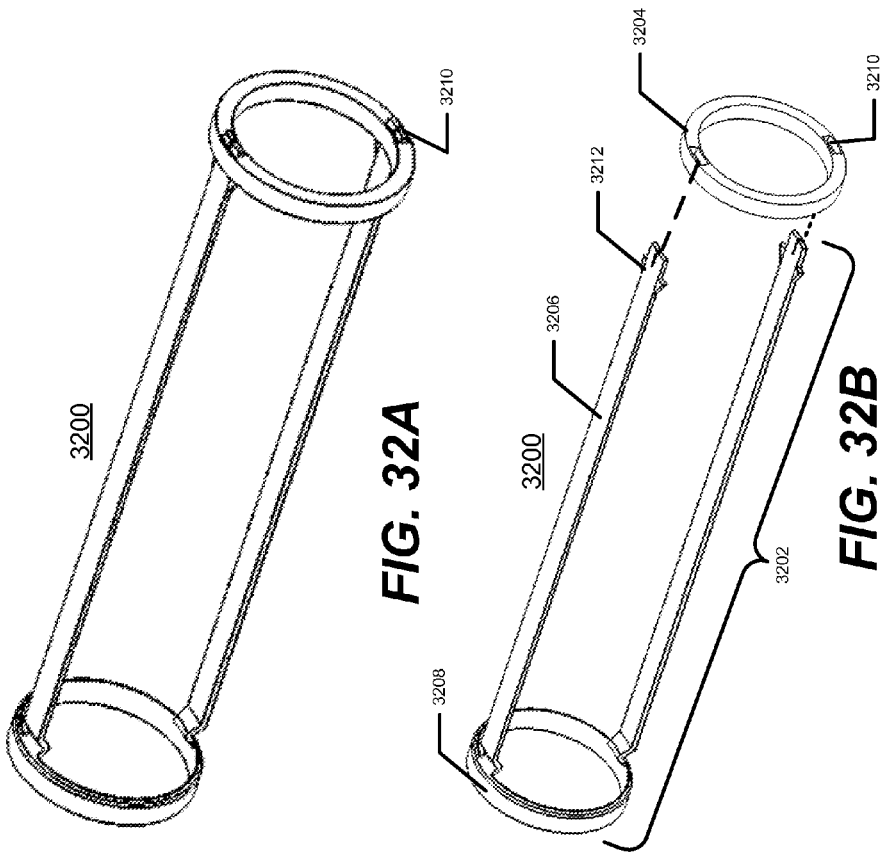
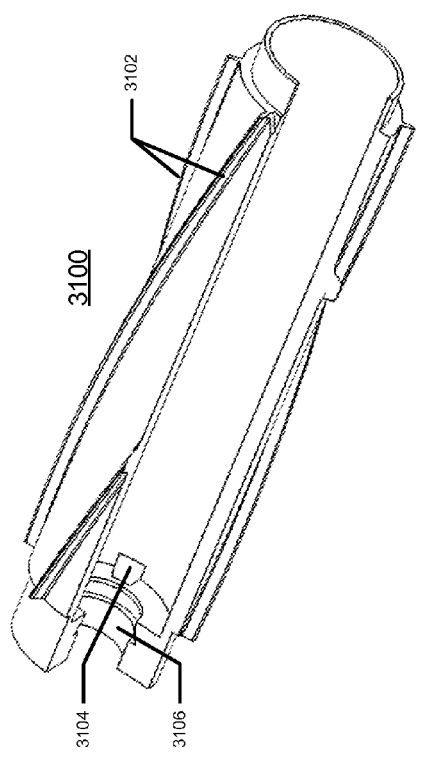
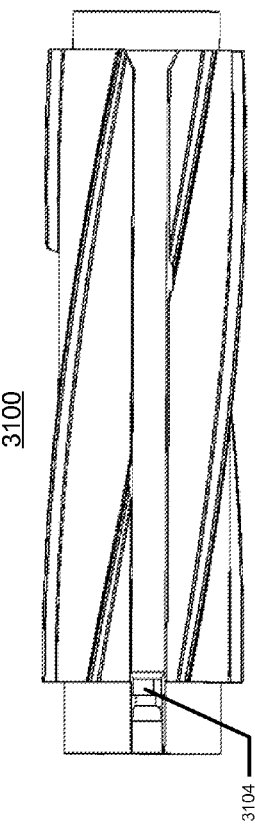
FIG. 32A
FIG. 32B
FIG. 31A
FIG. 31B

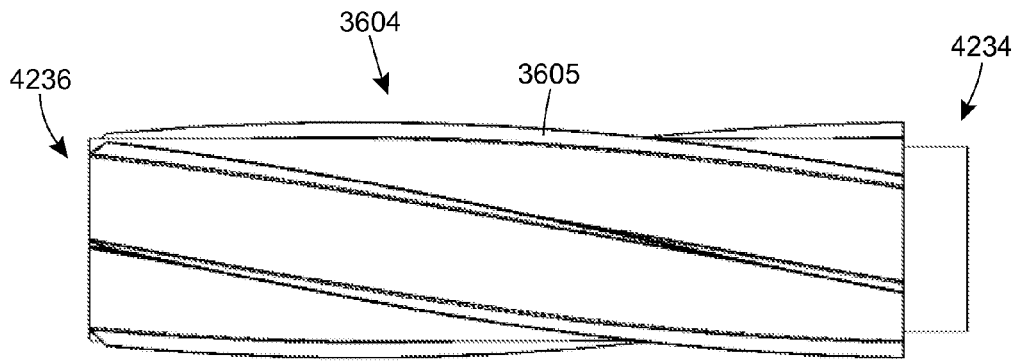
FIG. 42A
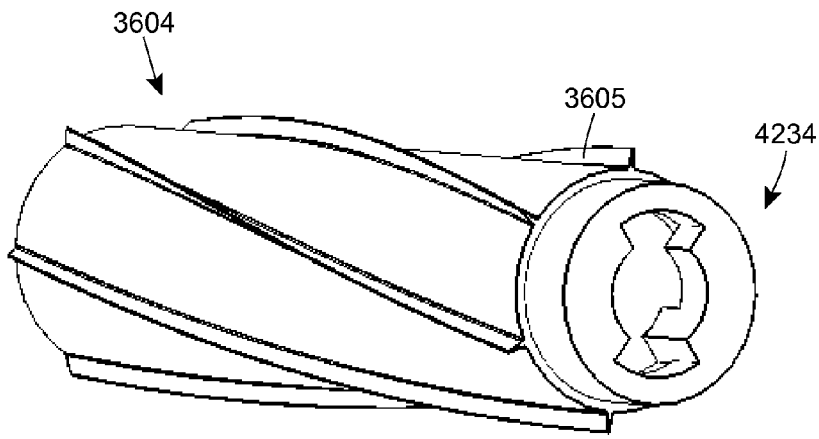
FIG. 42B
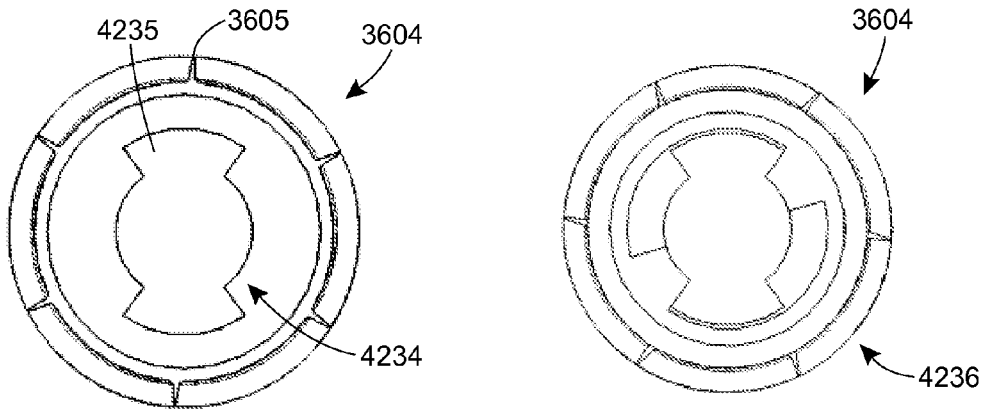
FIG. 42C  FIG. 42D

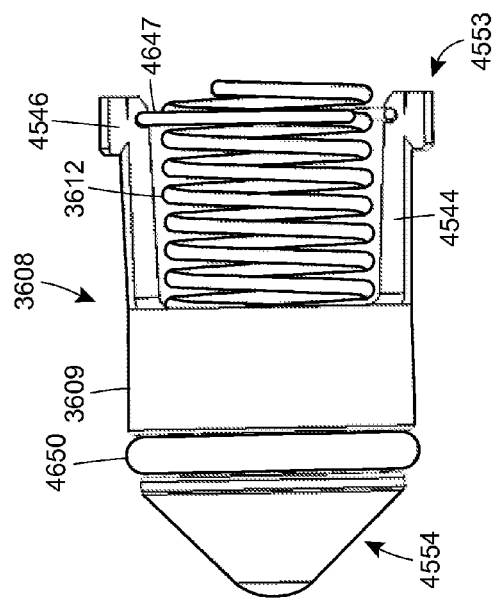
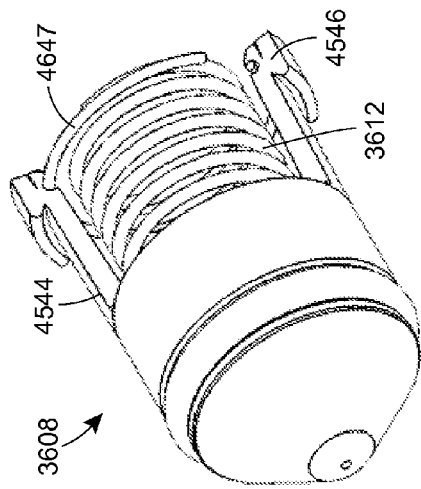
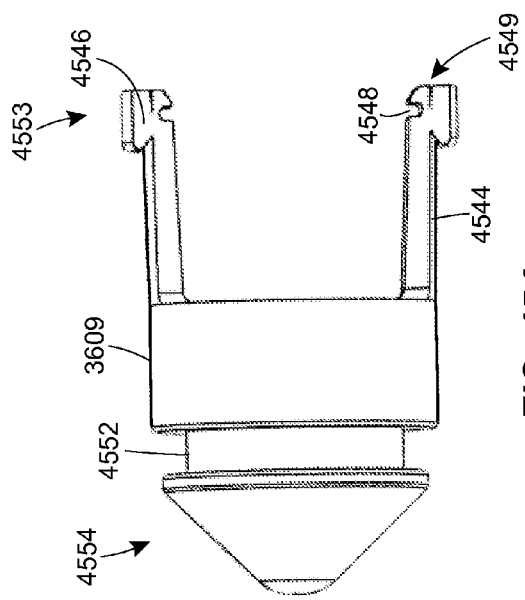
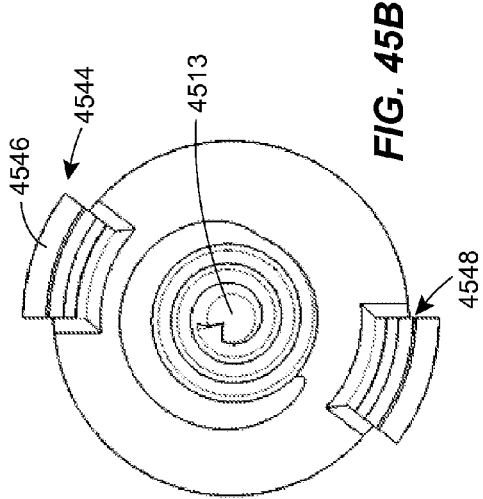
FIG. 46A
FIG. 46B
FIG. 45A
FIG. 45B

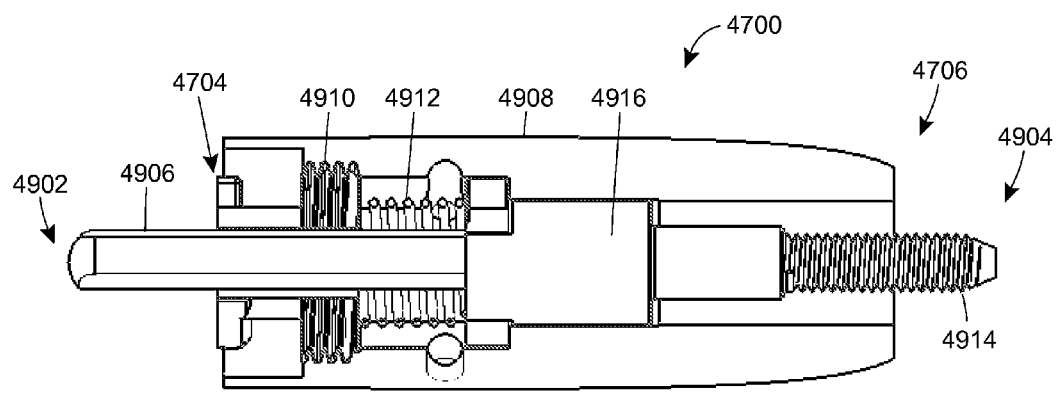
FIG. 49A
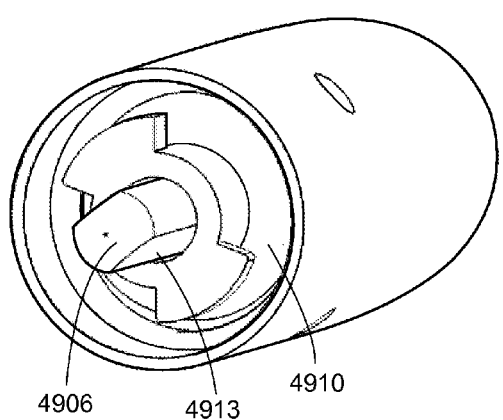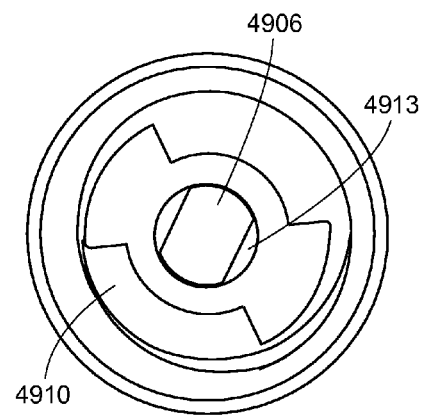
FIG. 49B　　　FIG. 49C

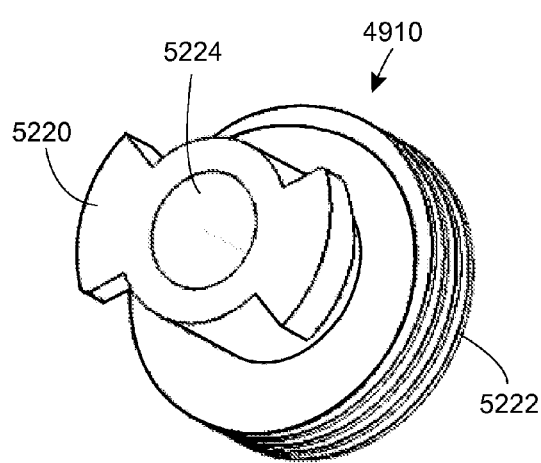
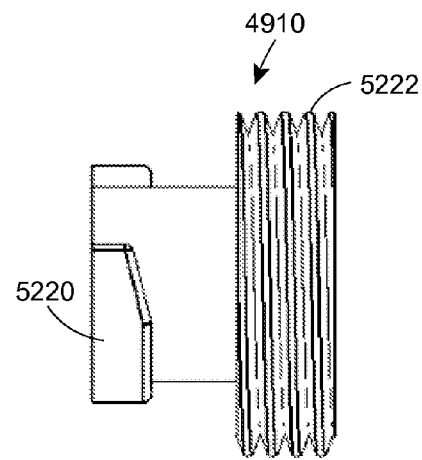
FIG. 52A  FIG. 52B
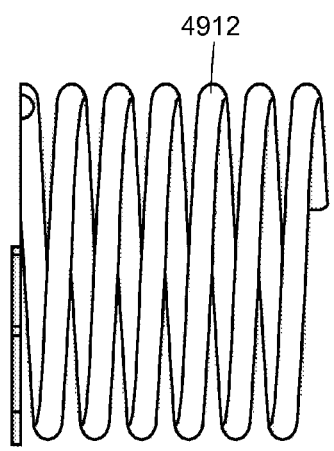
FIG. 53

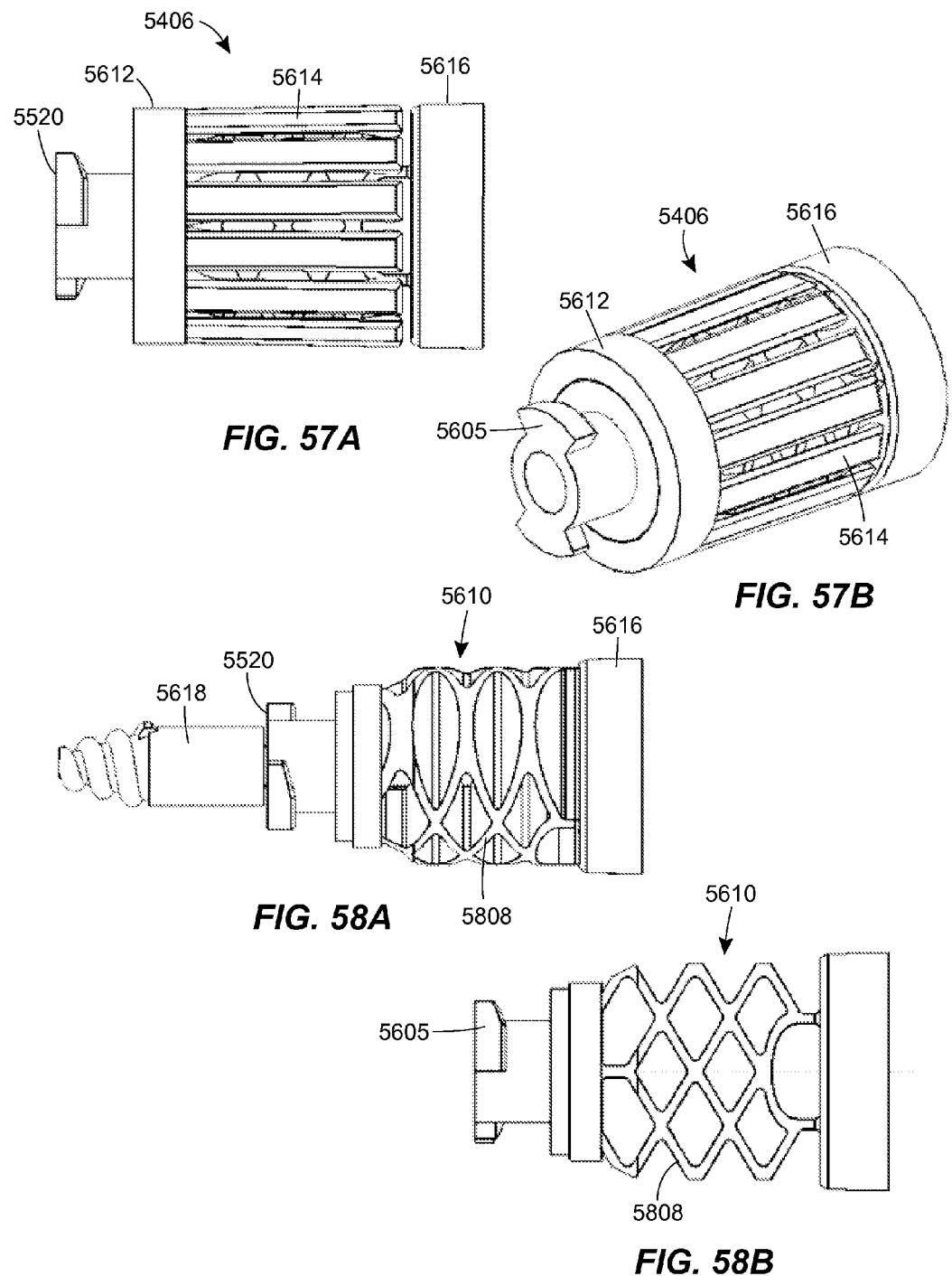

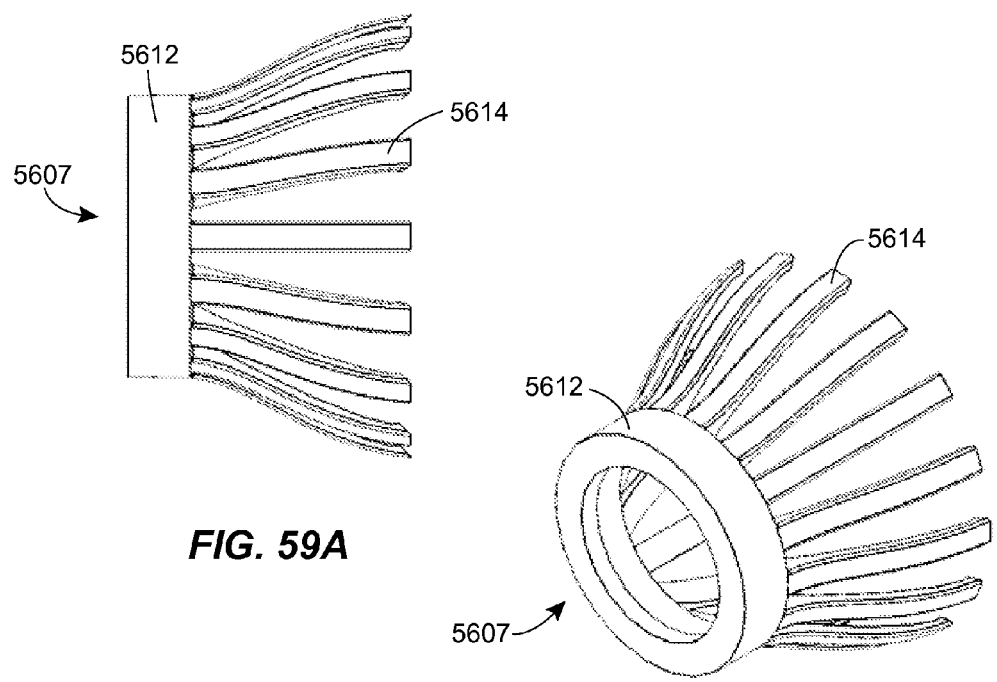
FIG. 59A
FIG. 59B
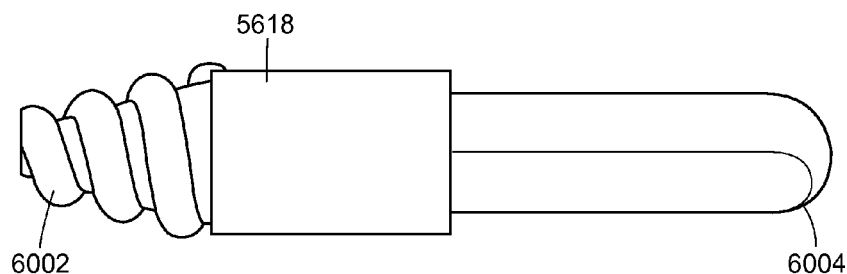
FIG. 60

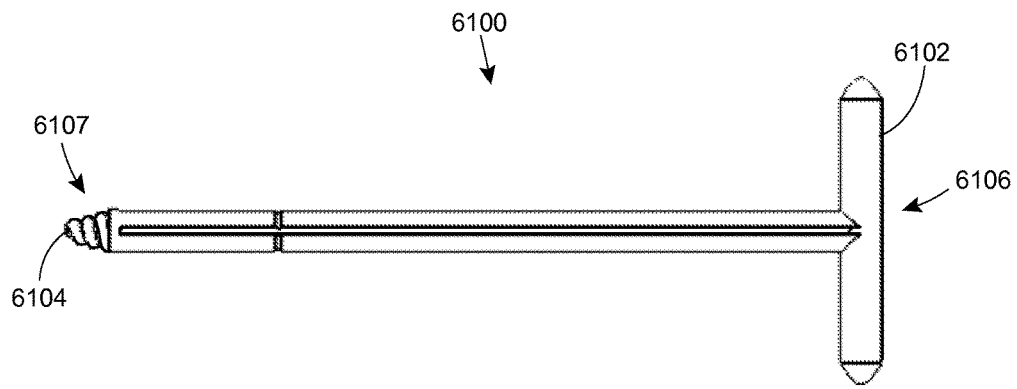
FIG. 61
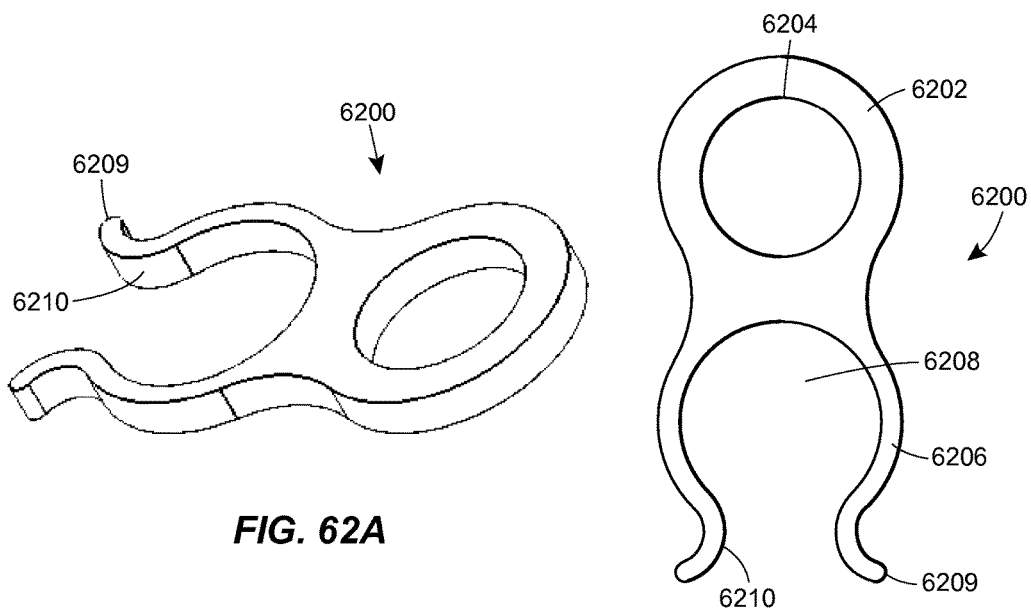
FIG. 62A
FIG. 62B

REMOTE TREATMENT SYSTEM

CROSS-REFERENCE TO RELATED APPLICATIONS

This application is a continuation-in-part of U.S. application Ser. No. 13/804,838 filed Mar. 14, 2013, and is a continuation-in-part of International Patent Appl. No. PCT/US14/27445 filed Mar. 14, 2014, which is a continuation-in-part of U.S. application Ser. No. 13/804,838 filed Mar. 14, 2013, and claims priority under 35 U.S.C. §119(e) to U.S. Provisional Appl. No. 61/924,527 filed Jan. 7, 2014. This application also claims priority under 35 U.S.C. §119(e) to U.S. Provisional Appl. No. 62/195,710 filed Jul. 22, 2015. The entire respective disclosures of each of the above-identified application are incorporated herein by reference.

TECHNICAL FIELD

The present disclosure relates generally to a system for delivering one or more payloads by a projectile fired from a remote location to a target.

BACKGROUND

Remote treatment systems are mechanical devices capable of administering one or more payloads (e.g., a liquid, a vaccine, an anesthetic, other medical treatment, a tracking device, a marker dye, a dye invisible to the naked eye, a tagging device, etc.), usually in a single dose or application to a target, such as the soft tissue of an unrestrained animal, usually by means of a ballistic projectile. A typical system for distance treatment includes a blowpipe or a gun and a dart containing a product, most often just carrying an anesthetic. However, modern delivery systems or methods suffer many shortcomings. For example, the target must be first located and then approached closely. Under most circumstances, animals or other targets must be within five to thirty yards of the shooter for the method or a projectile-based device to be effective. Many animal species are secretive and extremely difficult to locate, let alone approach closely. Also, many devices for close-range targets can be used only on large animals. Typical methods using projectiles tend to be inaccurate and the preferred target area on small animals may be very small. A misplaced shot might easily injure or kill the target. Even if placed correctly, the impact energy or penetration depth could be injurious or lethal to smaller animals. Furthermore, devices for close-range targets are often complicated to use, and training and experience are necessary for those devices capable of reaching targets beyond close-range, and most devices should not be used without some degree of formal instruction by experienced practitioners.

SUMMARY

In accordance with an embodiment of the present disclosure, a remote treatment system includes a remote treatment system including a cone assembly having a spine and a cone body at least partially surrounding the spine and adapted to store a cone payload, a syringe coupled to a portion of the cone assembly and adapted to store a syringe payload for treating and marking a target, and a vanes cup having an inner diameter sized to receive an outer diameter of the syringe. The vanes cup includes stabilization means with vanes or fins for stabilizing the remote treatment system. The remote treatment system also includes a pressure means at least partially disposed within the vanes cup and configured to apply a pressure against the syringe payload within the syringe in response to an impact between the cone assembly and the target, such that the syringe payload is expressed from the syringe.

The features and advantages described in this summary and the following detailed description are not all-inclusive. Many additional features and advantages may be apparent to one of ordinary skill in the art in view of the drawings, specification, and claims hereof.

BRIEF DESCRIPTION OF THE DRAWINGS

Embodiments of the disclosure are better understood with reference to the following drawings, wherein:

FIG. 1 is an exploded view of components of a remote treatment system;

FIGS. 18A and 18B are various views of an embodiment of the remote treatment system;

FIGS. 19A, 19B, and 19C are various views of a syringe assembly;

FIGS. 20A, 20B, 20C, and 20D are various views of another embodiment of a cone assembly;

FIGS. 22A, 22B, and 22C are various views of an inner spine section;

FIG. 23 is a view of a cannula;

FIGS. 24A, 24B, and 24C are various views of a piston;

FIGS. 25A, 25B, 25C, and 25D are various views of a ventil;

FIG. 26 is a view of a fins cup with fins folded flat;

FIGS. 27A, and 27B are various views of an embodiment of the remote treatment system;

FIGS. 31A and 31B are various views of a vanes cup;

FIGS. 32A and 32B are various views of a sliding assembly;

FIGS. 42A-D are various views of the vanes cup;

FIGS. 45A and 45B are various views of a piston of the remote treatment system of FIGS. 36A and 36B;

FIGS. 46A and 46B are various views of a piston assembly of the remote treatment system of FIGS. 36A and 36B, the piston assembly including the piston of FIGS. 45A and 45B;

FIGS. 49A, 49B, and 49C are various views of the bow bayonet assembly;

FIGS. 52A and 52B are various views of the anchor of the bayonet assembly;

FIG. 53 is a side view of the coil of the bayonet assembly;

FIGS. 57A and 57B are various views of the shell wad assembly in a loaded position;

FIGS. 58A and 58B are various views of a wad with a wad rod and without the wad rod, respectively;

FIGS. 59A and 59B are various views of a plurality of flights of a skirt of the shell wad assembly "in-flight";

FIG. 60 is a side view of a wad rod of the wad assembly;

FIG. 61 is a side view of a tool bar;

FIGS. 62A and 62B are various views of a safety clip apparatus;

Figure 2A:
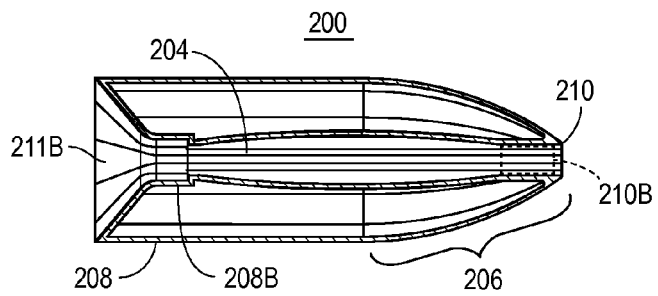
FIGS. 2A, 2B, 2C, 2D, 2E, 2F, 2G, 2H, 2I, 2J, 2K, 2L, 2M, and 2N are various views of one embodiment of a cone assembly.

Throughout the drawings, like reference numerals refer to like, similar or corresponding features or functions. The drawing figures depict a preferred embodiment of the invention for purposes of illustration and clearness of understanding only. One skilled in the art will readily recognize from the following discussion that alternative embodiments of the structures and methods illustrated herein may be employed without departing from the principles of the invention described herein.

DETAILED DESCRIPTION

In the following detailed description of the preferred embodiments, reference is made to the accompanying drawings, which illustrate one or more specific embodiments for practicing the teachings of the invention. The illustrated embodiments are not intended to be exhaustive of all possible embodiments. Instead, those of skill in the art will understand that other possible embodiments may be utilized, and that structural or logical changes may be made without departing from the scope of the disclosure.

FIG. 1 illustrates an exploded view of several components or assemblies of a remote treatment system (RTS), generally designated 100. As used herein, treatment, tag, chip injection, or inoculation may be defined as any introduction of foreign matter into or onto a target. A target may be any animal such as livestock, wild animals, humans, marine wildlife, avian wildlife, other land mammals, or any target into or onto which a payload may be delivered via syringe or other means as herein described. Treatment, marking, tagging, tracking, or inoculation may include introduction of a growth medium, anesthesia of an animal for handling or relocation, anti-parasitic management, biological and chemical control, broad spectrum and highly specific treatments in animal husbandry or wild animal management, control of indigenous life in security sector reform programs, disease prevention, drenching and worming, distribution of serums or antigenic substances, injecting of vitamins and minerals, delivery of any medicine and drug, introduction of a microorganism or other agent for disease eradication, microbial bacteriological genetic transfer, producing or boosting immunity to specific diseases, scientific and defense industry experimental and non-experimental research, and vaccination, and scientific and defense industry deployment.

In some embodiments, the RTS 100 may be a fin-stabilized discarding sabot (FSDS) that is fired from a delivery device or system such as a smoothbore firearm (i.e., a shotgun), a rifled shotgun or "slug-gun", a rifle, air gun, etc. The RTS 100 may include a projectile assembly 150, a wad 600 (when deployed in a smoothbore firearm), and a shell 700. Integrating a shotgun or rifle wad into the functionality allows, by design, for the possibility of "caseless ammunition" deployment. The projectile assembly 150 may include a cone assembly 200, a syringe assembly 300, and a fins-cup assembly 400. Generally, the syringe assembly 300 is filled with a payload such as a vaccine, an anesthetic, vitamins, etc. The gun fires a charge in the shell, which causes the wad 600 to carry the projectile assembly 150 through a barrel of the firearm. Once the wad 600 and the projectile assembly 150 reach the muzzle of the barrel, air resistance causes the wad 600 to fall away from the projectile assembly 150. The projectile assembly 150 then flies to a target, stabilized by fins on the fins-cup. The projectile assembly 150 then impacts the target, causing the cone assembly to flatten, a needle or cannula of the syringe assembly 300, when fitted by the operator, to enter the target, and a payload of the syringe assembly 300 to be expressed into the target and, in some cases, a cone payload to be expressed onto or into the target. Once the syringe is emptied into the target, in some embodiments the projectile assembly 150 may fall away from the animal or other target; in other embodiments, the assembly 150 may remain in the animal or other target for a period of time, then fall away. In still other embodiments, the projectile assembly 150 (or parts thereof) may stay with the target for longer or shorter periods.

Upon impact, a cone assembly 200 may increase the area over which kinetic energy from the projectile assembly 150 is transferred to the target. For example, the projectile assembly may include a deformable plastic or foam body that carries one or more cannula. Upon firing, the deformable cone assembly 200 may compress to conform to various smoothbore or other bore barrel configurations. For example, some shotguns include a choke tube (e.g., full, modified, improved, etc.) or may include a plurality of non-parallel barrels. The deformable cone assembly may conform to these various barrel configurations as it travels down the barrel. Upon impact, the cone assembly may deform and spread the kinetic energy of the projectile assembly 150 into an area of the target as the cannula enter the target to deliver the payload. In some embodiments, the force of impact renders the cone assembly unusable.

Referring to FIGS. 2A-F, one embodiment of the cone assembly 200 may include a plurality of deformable sections 202 surrounding a core 204 having an axis A-A. While the drawing figures illustrate a cone having twelve sections 202, other embodiments may include fewer or more sections. The sections 202 may be flexibly joined about the axis A-A. The sections 202 may form the cone 200 as a single body having scoring indentations or as multiple bodies joined by joints 205 that allow the cone 200 to deform around the core 204 and the axis A-A.

In some embodiments, when the sections 202 are joined, the outside surface of the cone 200 may be shaped generally as a projectile having a conical portion or ogive 206 and a cylindrical portion 208. In other embodiments, a cone assembly 200 may be shaped to fit snugly in the barrel of a firearm before and upon firing. For example, immediately before curving down to the apex, the cone assembly may bulge outward to have a gentle contact with the inside diameter of the barrel to aid in guarding against rocking or wobble as the projectile assembly 150 moves down the barrel upon or after firing. Drawing FIGS. 5A-E illustrate embodiments of the projectile assembly with a bulging area in the cone assembly.

The outside surface of the cone 200 may be shaped generally as a projectile having a conical portion or ogive 206 and a cylindrical portion 208. The ogive 206 may include a fore-end ring 210 that is formed by the plurality of radially joined segment sections 202. In other embodiments, a separate fore-end sleeve 210B may be placed in a sealing relation to the cannula and connected to each section 202 via the fore-end ring 210. The fore-end ring 210 may be adapted to fit in sealing relation against a corresponding sealing surface around a body fitted within the core 204 along axis A-A running from the cone assembly apex to a center of the cone assembly base. For example, the fore-end ring 210 may provide a seal around a cannula 302 of the syringe assembly 300 at an exit port 310 to prevent the payload from leaking from the syringe body 306 or pouch 360 (FIG. 3, described below). In some embodiments, tips of the sections 202 may collectively form the fore-end ring 210. In other embodiments, the fore-end ring 210 may be a separate element from the sections 202 (e.g., an o-ring, a gasket, etc.). In any event, when the cone assembly is "at rest" and in an extended first position, the fore-end ring 210 may provide a seal for the cannula 302 to prevent any liquid or other material inside the syringe assembly 300 from seeping or leaking out of the syringe assembly 300. The cone assembly 200 may begin with the ogive 206 and terminate at a cone base 211B. The cone base 211B may include a base ring 208B joining the base portion of the segments and may abut a hub/head assembly 304 of the syringe assembly 300.

FIG. 2G illustrates a cone section 202 when "at rest" (e.g., before the RTS impacts a target and the fore-end ring 210 is in an extended first position). The cone section 202 may include an inner rib 212 (i.e., a first portion) and an outer rib 214 (i.e., a second portion). The inner and outer ribs may surround a cone payload area 215. The cone payload area 215 may carry a marking material (e.g., a marking dye). In some embodiments, the cone assembly 200 may carry an isotopic labeling compound. In response to impact with a target, the ribs 212 and 214 may shift around one or more pivots that connect the inner and outer ribs 212, 214 from an undeformed first position and a deformed second position. This shifting may also cause the fore-end ring 210 to shift along the longitudinal axis of the core 204 from an extended first position toward the base ring 208B in a retracted second position. This shifting may cause the joints 205 to open and any payload within the payload area to escape through the opened joints 205, thus marking the target. While the cone ribs 212, 214 shift from an undeformed position to a deformed second position, the cone ribs 212, 214 may break, such that the cone may only be used once. However, in another embodiment, the ribs need not break. The cone payload area 215 may also carry the payload to a topical area of the target without penetration of the target surface. For example, the cone payload area 215 may carry a fluorescent or other high-visibility marking dye, an infrared marking liquid, a topical treatment, or other types of liquid or viscous payloads, whether or not there is a syringe payload.

The inner rib 212 may include a fore-end ring section 210A, and an inner rib hinge section 216. The fore-end ring section 210A may form a portion of the fore-end ring 210 when formed with any remaining sections 202 to make a complete cone 200 around the core 204. Similarly, a base ring section 208A may form a portion of the base ring 208B when formed with any remaining sections 202 to make a complete cone 200. The inner rib hinge section 216 may include a leading inner arm 216A and a trailing inner arm 216B that terminates at an inner rib hinge base 216C. In a preferred embodiment, the inner rib hinge 216 section may curve into the cone payload area 215 toward the outer rib 214. For example, the leading inner arm 216A may curve toward the outer rib portion 214 until it reaches axis B-B, then the trailing inner arm 216B may curve away from axis B-B and the outer rib portion 214 until it terminates at the inner rib hinge base 216C. In other embodiments, the leading inner arm 216A may have no curve and follow the axis A-A along the core 204, or may curve out from the cone payload area 215 toward the core 204 and away from the outer rib 214. The inner rib hinge base 216C may be formed by an overlap area with the trailing inner arm 216B along a longitudinal axis of the inner rib 212. The outer rib 214 may include an outer rib arm 214A and a cone base section 211A joined at an outer rib knuckle 214C. The outer rib 214 may join the inner rib 212 at the inner rib hinge base 216C and the fore-end ring section 210A.

Figure 2B:
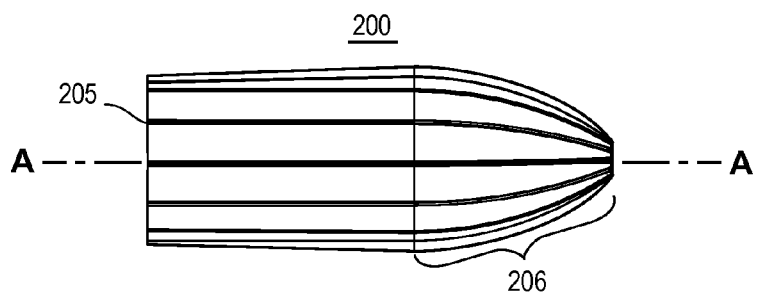
Figure 2C:
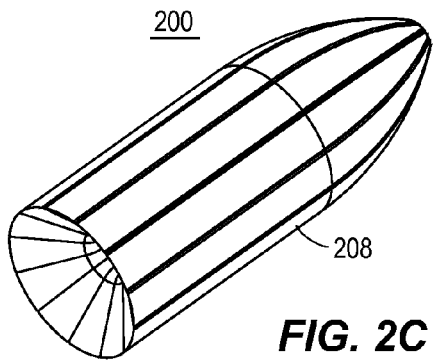
Figure 2D:
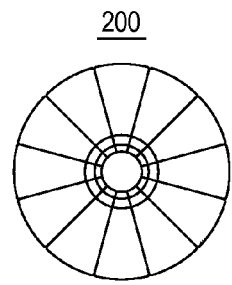
Figure 2E:
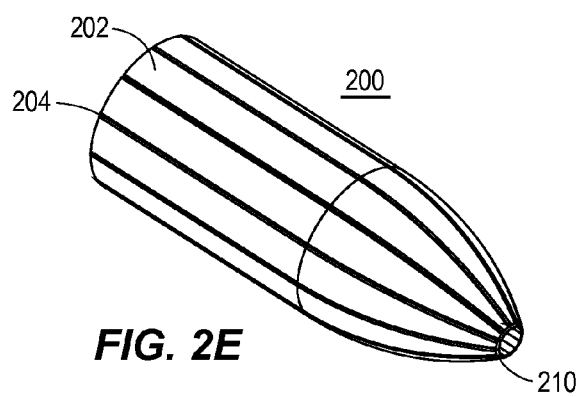
Figure 2F:
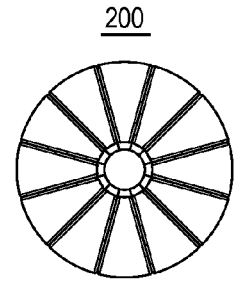
Figure 2G:
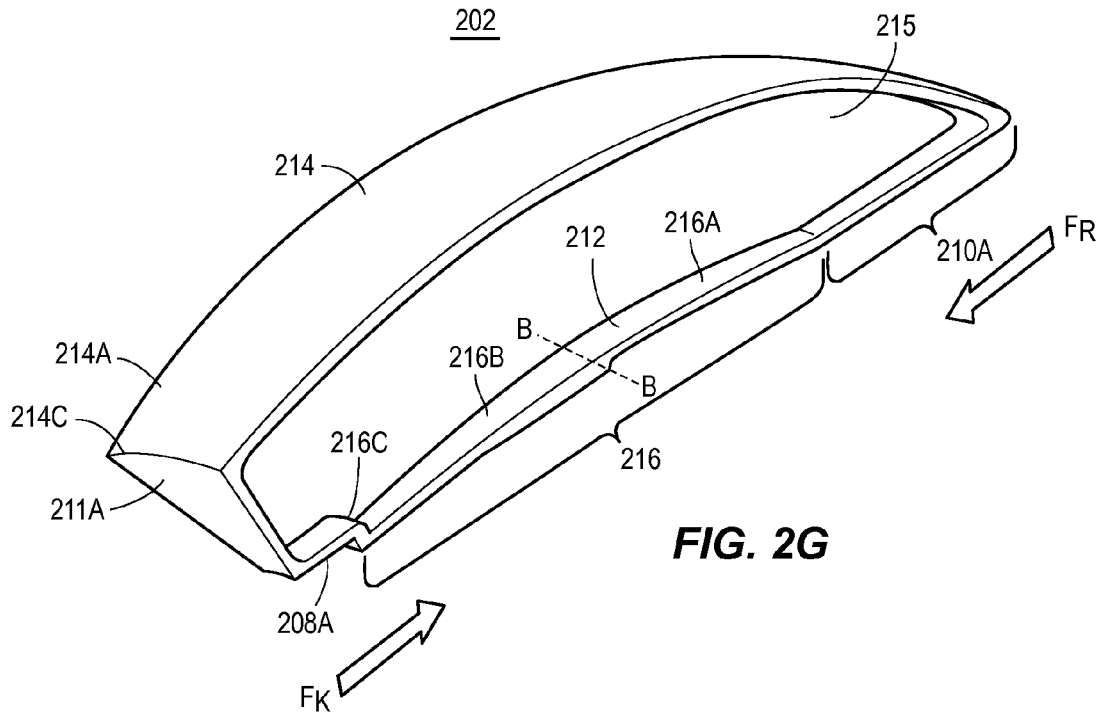
Figure 2H:
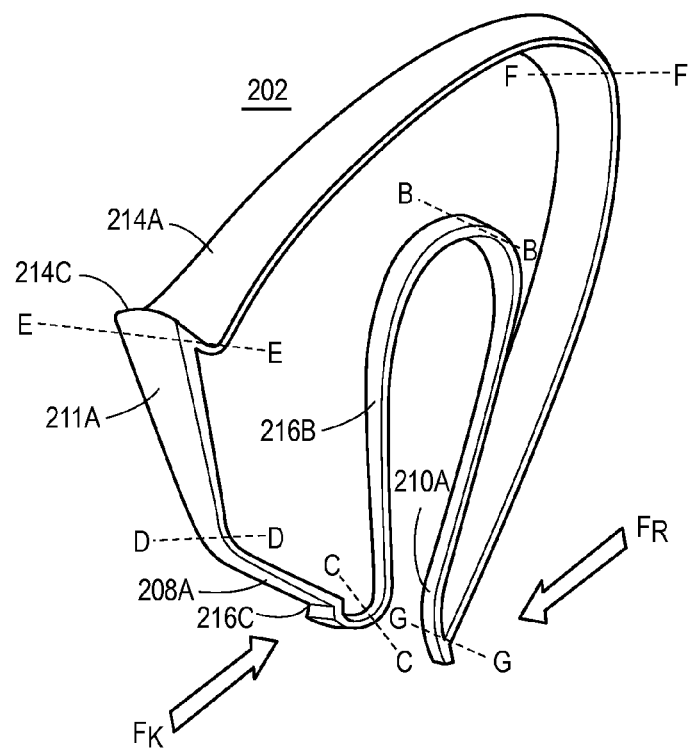
Figure 2I:
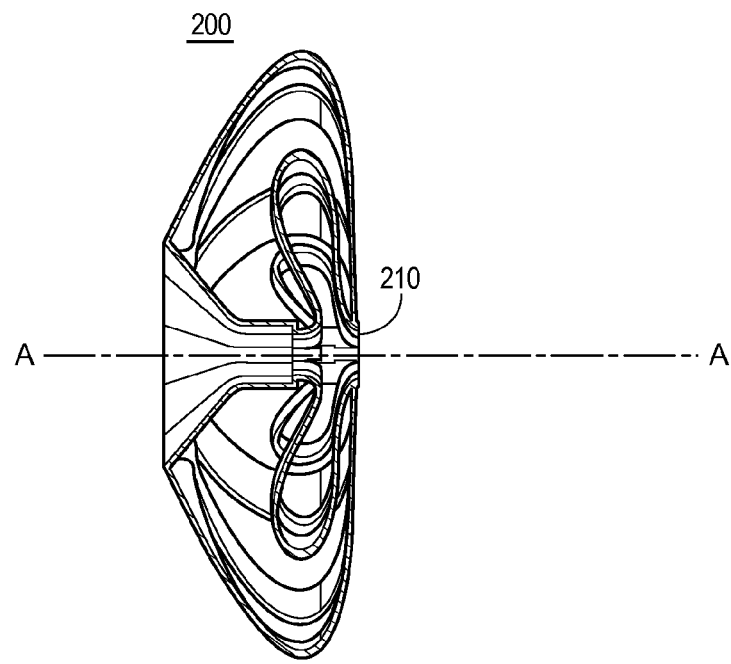
Figure 2J:
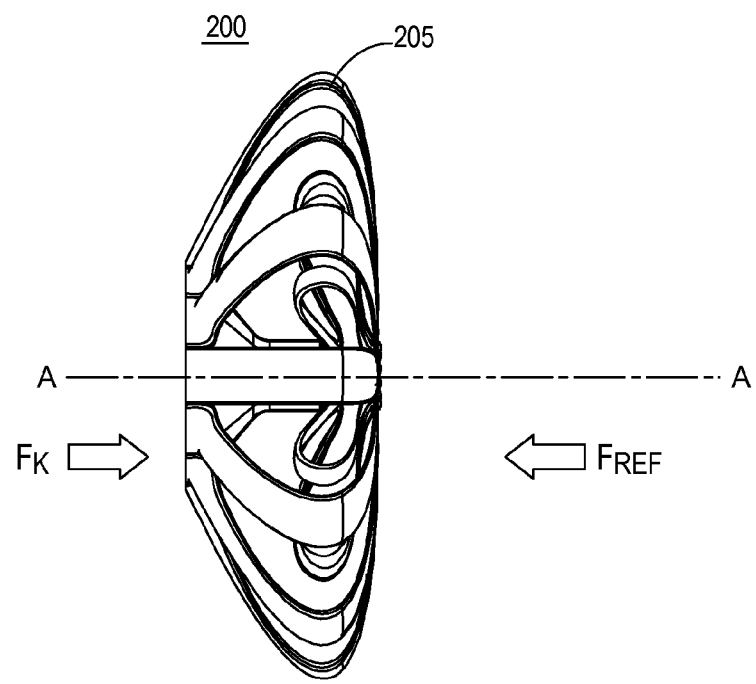
Figure 2K:
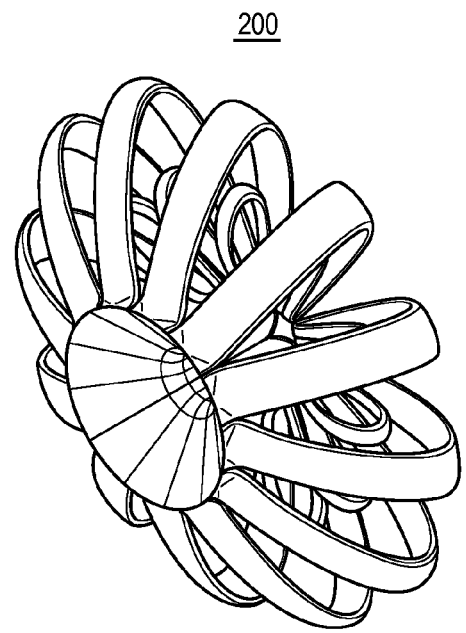
Figure 2L:
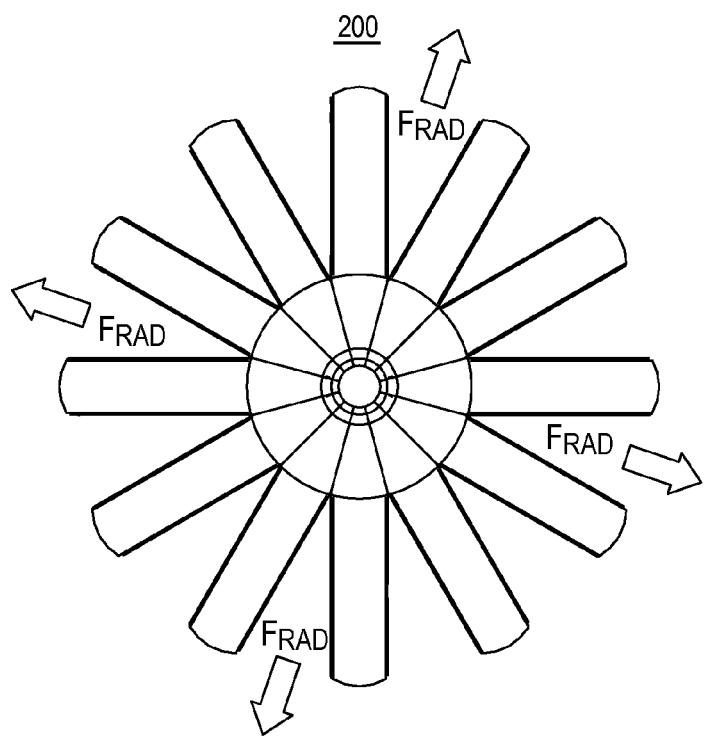
Figure 2M:
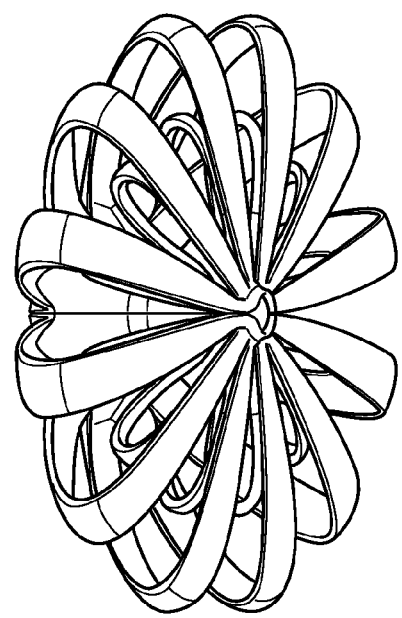
Figure 2N:
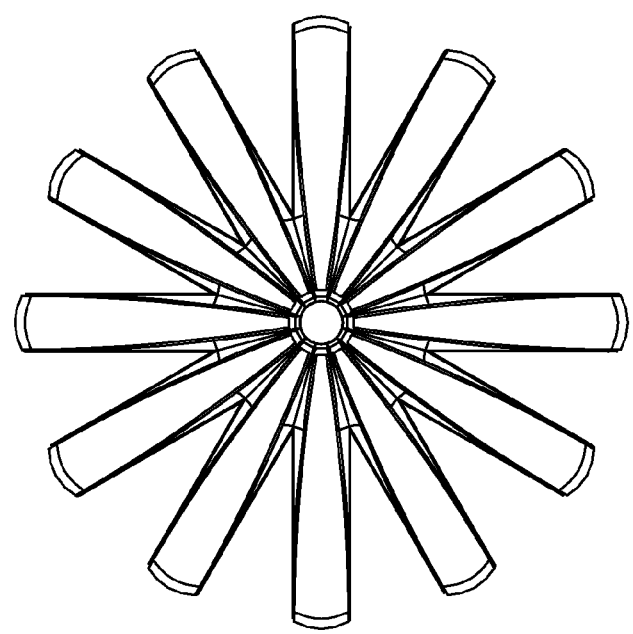

FIG. 2H illustrates a cone section 202 when deformed after impact with a target and shows the fore-end ring 210 in a retracted second position. The kinetic energy of the projectile assembly 150 in flight ($F_K$) is transferred through the projectile assembly 150 to the target along axis A-A and causes the cone assembly to pivot from an undeformed first position and a deformed second position. As some of the projectile assembly's kinetic energy is reflected from the target back toward the projectile assembly ($F_{REF}$), the fore-end ring 210A and the cone base section 211A a shift toward each other due to the inner rib 212 and outer rib 214 shifting about a plurality of pivots within each cone assembly section 202. In response to impact, the forces deform each cone section 200 radially outwardly from a center of the fore-end ring 210 and around a pivot defined by axis A-A. The inner and outer ribs may deform radially away from the core 204 center and a pivot defined by axis A-A as the forces move the fore-end ring section 210A and the cone base section 211A toward each other along the core 204. The impact forces may generally cause the leading inner arm 216A and the trailing inner arm 216B to shift toward each other around a pivot defined by axis B-B, the trailing inner arm 216B and inner rib hinge base 216C to deform toward each other around a pivot defined by axis C-C, the inner rib hinge base 216C and the cone base section 211A to deform away from each other around a pivot defined by axis D-D, the cone base section 211A and the leading outer arm 214A to deform away from each other at a pivot defined by axis E-E, the leading outer arm 214A to deform at a pivot defined by axis F-F, and the leading outer arm 214A to deform toward the fore-end ring section 210A at a pivot defined by axis G-G. One or more of the inner and outer arms may include structures along one or more of the axes A-A through G-G that cause the cone 200 to remain deformed after it impacts the target. For example, the cone 200 may include scoring along the axes that permits the cone to further break apart in response to impact.

FIGS. 2I-2N illustrate the cone assembly 200 after impact with a target and deformation of each cone section 202. As shown, impact may impart forces along the axis A-A and drive the fore-end ring 210 and the cone base section 211A toward each other and into a retracted second position. In doing so, the impact forces also cause the joints 205 to separate as the surface of the cone assembly 200 is subjected to radial forces ($F_{RAD}$) perpendicular to the axis A-A resulting from compression of the cone assembly 200 during impact.

Figure 2O:
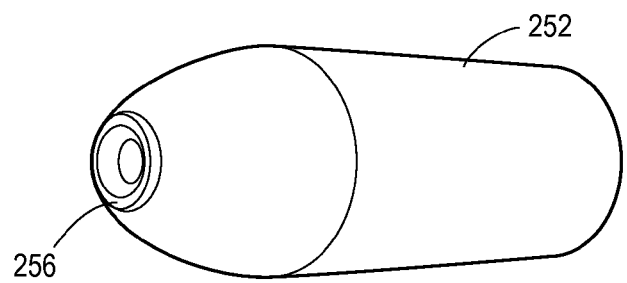
FIGS. 2O, 2P, and 2Q are various views of another embodiment of a cone assembly.
Figure 2P:
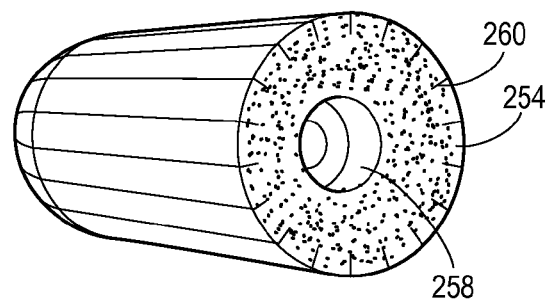
Figure 2Q:
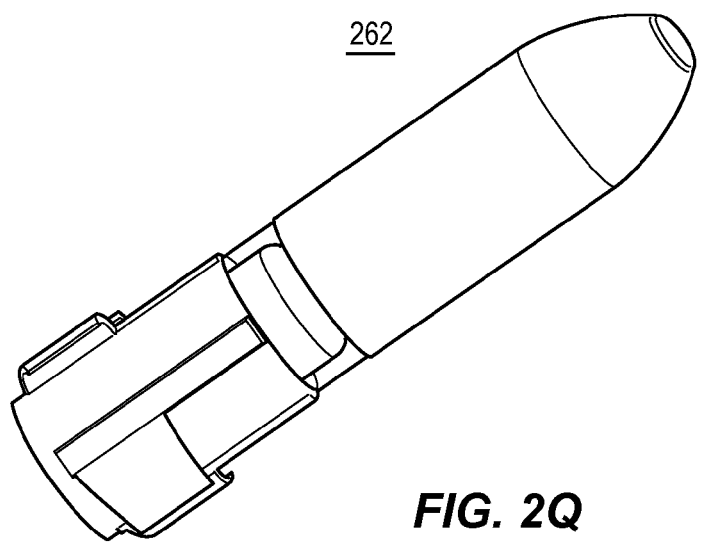

FIGS. 2O-2Q illustrate an alternative embodiment of the cone assembly 200. A foam cone may be formed of a solid, spongy, cellular material, such as polyurethane, for example. In some embodiments, the foam cone 250 is constructed from a polyester resin and catalyst in the presence of a gas such as carbon dioxide. The foam cone 250 may be shaped to a bullet shape, similar to the cone assembly 200. An outer surface (i.e., a first portion) 252 of the foam cone 250 may be treated such that the cellular structure of the foam cone interior (i.e., a second portion) 254 is concealed. Sealing or otherwise treating the outer surface 252 of the foam cone 250 may also improve the ballistic profile of the foam cone 250 over a cone with an exposed cellular structure.

The foam cone 250 may include a fore-end ring 256 and a base ring 258, which collapse toward each other around a pivot as a result of impact forces from an undeformed first position and a deformed second position. The internal cellular structure of the foam cone 250 may also hold a payload similar to the payload carried by the cone 202, as described above.

The cone surface 252 may also include slots 260. The slots may be molded or cut into the foam. The slots 260 may allow the foam cone 250 to spread upon impact to lower the amount of kinetic energy transferred from the projectile assembly 262 to the target. The slots 260 may also allow the payload carried within the foam cone's internal cellular structure to be released from the core and onto the target upon impact.

Figure 3A:
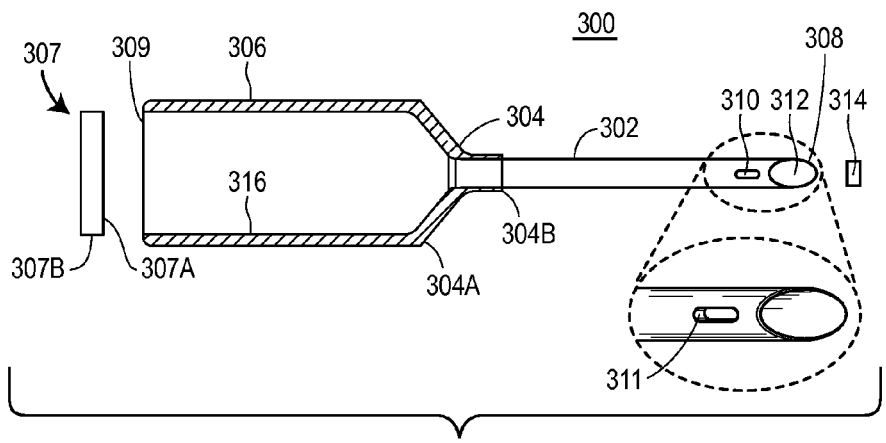
FIGS. 3A, 3B, 3C, 3D, 3E, 3F, 3G, 3H, and 3I are various views of a syringe assembly.
Figure 3B:
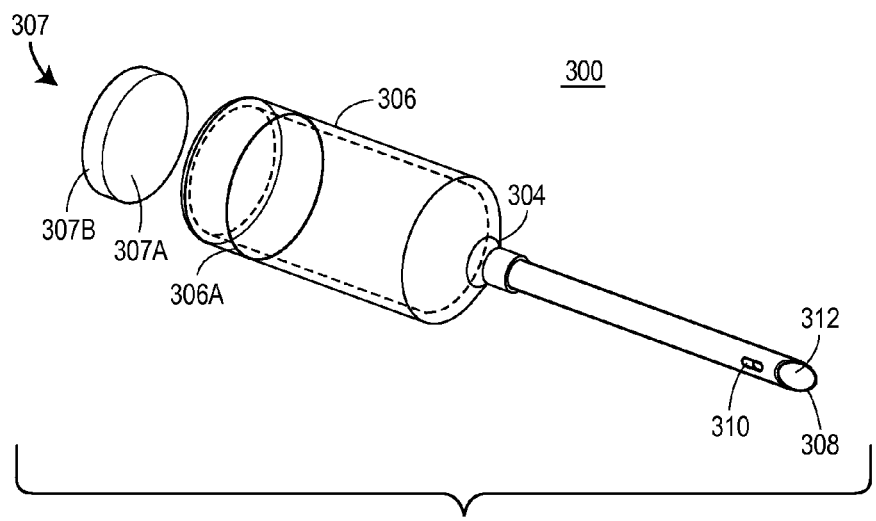
Figure 3C:
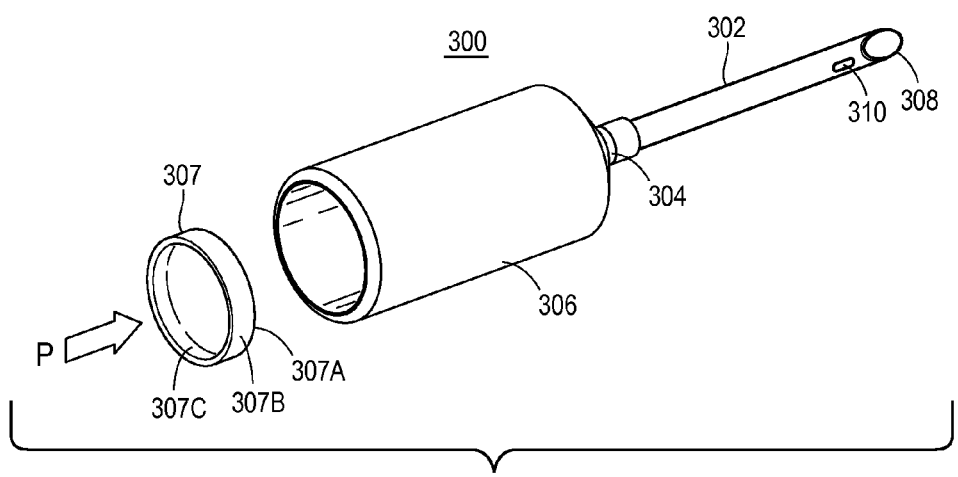

FIGS. 3A-3C illustrate a payload or syringe assembly 300. The payload assembly 300 may include an implantable or attachable payload such as a satellite or radio tracking and information or data harvesting systems and infrastructures (e.g., a global positioning system (GPS) locator, an IRIDIUM satellite constellation or other satellite system, link microchip, a radio transmitter, a radio frequency identification chip, etc.). The assembly 300 may include a needle or cannula 302, a hub/head 304, a hollow cylindrical barrel or body 306, and a plunger assembly 307. The cannula 302 may include a hollow or a solid bevel tip 308 and at least one exit port 310 located on a longitudinal side of the cannula. While the embodiment described is generally described as having one cannula, the syringe assembly 300 may include a plurality of cannulae. For example, a syringe assembly 300 for an intramuscular injection may include a single cannula 302, but a syringe assembly 300 for a subcutaneous injection may include a plurality of shorter cannulae. While FIGS. 3A-3C illustrate two oval-shaped exit ports 310, the cannula 302 may include any number of exit ports of various shapes and sizes (e.g., circular, square, etc.). Furthermore, the one or more exit ports 310 may also be shaped to include a baffle 311. The baffle 311 may direct a payload from the port 301 at a rearward acute angle in relation to the longitudinal axis of the cannula 302 and generally toward the hub/head 304. In any event, placement of the exit ports 310 may counteract a force that might act to push the syringe assembly 300 out of a target in reaction to the payload being expressed into the target. Furthermore, the solid bevel tip 308 may also facilitate puncturing the skin or hide of the target and, because the tip is solid, any hair or soft tissue fragments removed by the puncturing process are less likely to impede the flow of the payload upon impact than a typical front-ported cannula. Oval, or other shaped, exit ports 310 may be approximately one millimeter or less to two millimeters or more at their widest diameter and one-half or less to one millimeter at their narrowest diameter. The cannula 302 may be approximately three centimeters in length, although many other lengths are possible in different applications of the RTS.

In other embodiments, the bevel 308 includes an opening 312, which may be closed with a bevel plug 314 once the syringe body 306 is filled. The bevel plug 314 may be made of a self-sealing material. The self-sealing bevel plug 314 may be adapted to fit in sealing relation against a corresponding sealing surface within the tip of the cannula 302. For example, the syringe body 306 may be filled by inserting a filling tube or other type of filling device though the bevel plug 314 where the filling device is a smaller gauge than the cannula 302. The payload of the filling assembly may then be expressed into the syringe body 306, and the filling assembly may then be removed from the bevel plug 314. In some embodiments, the syringe body 306 includes a payload volume of 4.5 to 10 mL; however the body may include various other payload volumes. For a 4.5 mL payload, a filler assembly may have a capacity of approximately 20 mL or more. The self-sealing bevel plug 314 may then seal the payload within the syringe body 306.

The hollow cylindrical body 306 may be constructed of clear polyurethane, latex, or other resin material to allow a user to see a fill level. There may be markings for quantities of fill. The body 306 may include a hub/head or front end 304 and an open end 309 that oppose each other along the longitudinal axis of the syringe body 306. The hub/head 304 may be shaped as a cone conforming the to the cone assembly base 211B and include a base 304A having a diameter that conforms to the outer diameter of the hollow cylindrical body 306. The hub/head or front end 304 may also include a hollow cylindrical apex 304B having an inner diameter sized to receive an outer diameter of the cannula in a sealing relation. The outer diameter of the body 306 may be sized to fit in sealing relation against a corresponding sealing surface such as an inner diameter of the fins-cup assembly 400 (FIG. 4). The hub/head 304 may also be sized to receive the cone assembly base 211B. The base 211B and hub/head 304 may be affixed to each other in a sealing relation such that the cone assembly and syringe assembly remain connected during filling of the syringe body, fitting of the syringe to the fins-cup assembly 400, fitting of the completed projectile assembly 150 to the wad assembly 600 and shell 700, during flight of the projectile 150, and upon impact with a target. The body 306 may include a sealing ring 306A, may be sized such that an airtight seal exists between the inner diameter of the fins-cup assembly 400 (FIG. 4) and the outer diameter of the syringe body 306, or may be glued or sonically welded together, as described herein.

Kinetic energy or a pressure means may cause the payload to be expressed from the syringe assembly 300 in response to impact with a target. In some embodiments, kinetic energy may include the energy transferred to the payload in response to the projectile assembly's impact with a target while the pressure means may include one or more a pressurized fluid and a coil, tube, or conical spring 307D (e.g., a conical coil spring as shown in FIG. 5C) that may provide a pressure P (FIG. 3C) against the payload to express the payload from the syringe body 306. Once the fore-end ring 210A slides below the exit ports 310 of the cannula as the cone assembly 200 deforms to the retracted second position in response to impact, the payload may be expressed from the exit ports 310 due to increased pressure within the syringe body 306 against the payload. For example, kinetic energy of the projectile assembly 150 during flight may be transferred to the payload in response to impact with a target. This kinetic energy may cause the increased pressure within the syringe body 306 to express the payload into the target. In another example, in response to impact with a target, a plunger assembly 307 may be moved from a rear opening of the syringe body 306 toward the hub/head 304. The plunger assembly 307 may include one or more of a plunger seal 307A and a cup 307B. While FIGS. 3A, 3B, and 3C show each of the seal 307A and cup 307B as approximately one-half of the entire plunger assembly 307, each of the seal 307A and cup 307B may be more or less of the entire assembly 307. For example, the seal 307A may be the top face of the cup 307B.

The plunger seal 307A may be adapted to fit in sealing relation against a corresponding sealing surface such as an inner wall 316 of the syringe body 306 to form a seal between the plunger seal 307A and an inner wall 316 of the syringe body 306. In some embodiments, the plunger seal 307A includes a rubber or plastic gasket. When the fore-end ring 210A slides from the extended first position past the exit ports 310 to the retracted second position in response to impact, a pressure against the plunger seal 307A may push the seal along the inside of the body 306 toward the cannula 302, allowing the syringe assembly 300 to express a payload through the exit port 310. In some embodiments, kinetic energy during flight of the projectile assembly 150 may be transferred to the plunger assembly 307, without additional force, upon impact with a target. The kinetic energy of the plunger assembly 307 may increase pressure against the payload and, once the fore-end ring 210A slides past the exit ports 310 to the retracted second position in response to impact, the pressure may release the payload through the exit ports 310. The kinetic energy may force the plunger assembly 307 from an opening of the syringe body 306 toward the hub/head 304 of the cannula 302 upon impact to increase the pressure of the payload within the body 306. In other embodiments, a plunger cup 307B may provide an enclosed or hollow area 307C behind the plunger seal 307A for a compressed fluid (e.g., a gas such as air or $CO_2$) or a coil spring 307D (shown in FIG. 5C). The coil spring 307D may be compression coil spring that is designed to resist being compressed. The compression coil spring 307D may also be conically-shaped. Either the wide or narrow portion of the conical spring 307D may abut the plunger assembly. The compressed gas or compressed coil spring may bias the plunger assembly against the payload to create a positive pressure within the syringe assembly 300.

As shown in FIG. 3C, pressure P exerted against the cup 307B biases the plunger assembly 307 toward the cannula 306. The pressure P may be applied by one or more of the kinetic energy, compressed fluid, and coil spring 307D. The pressure may also be created by a chemical reaction within the syringe body 306. For example, one or more capsules containing a chemical may break upon impact with the target and react with another chemical present in the body 306. The reaction may release a gas to pressurize the body. In some embodiments, the body 306 is constructed of a material including a chemical that reacts with the chemical present in the breakable capsule. For example, a syringe body made of a metal (e.g., zinc) may react with hydrochloric or sulfuric acid to produce hydrogen gas. Further, the pressure may be translated to the plunger seal 307A to create a positive pressure within the syringe body 306. The pressure P may be equalized within the syringe body 306 to express the payload through an exit port 310 when the fore-end ring 210A slides past the exit ports 310 to the retracted second position in response to impact. In some embodiments, one or more of the compressed gas and coil spring 307D may exert a pressure between 10 and 15 Newton-meters, or approximately 7.3 to 11 foot-pounds within the syringe body. This pressure may cause the payload to be expressed from the exit ports 310 with or without the assistance of the plunger assembly 307 and/or coil spring. When used with the plunger assembly 307, the pressure may bias the cup and plunger against the payload and to move the plunger assembly 307 down the syringe body 306 to express the payload through the one or more exit ports 310. Further, when the syringe assembly 300 and the plunger assembly are joined, the plunger seal 402 may be fitted within the body 306 against the payload to remove any air from within the syringe body 306 to eliminate any danger of an air embolism during deployment of the remote treatment system (RTS) 100.

Figure 3D:
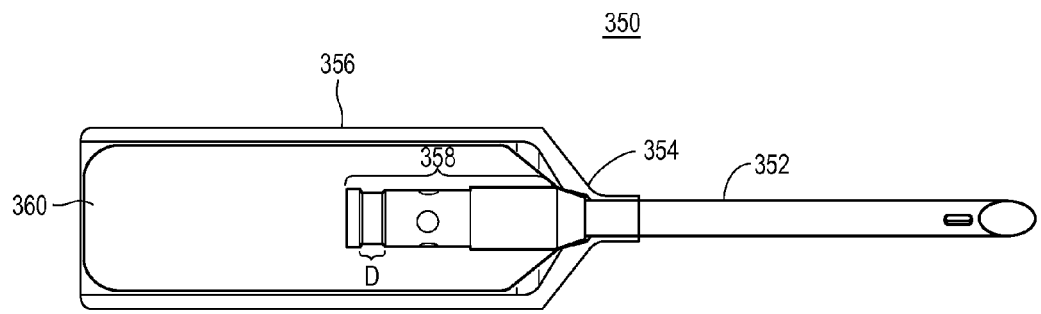
Figure 3E:
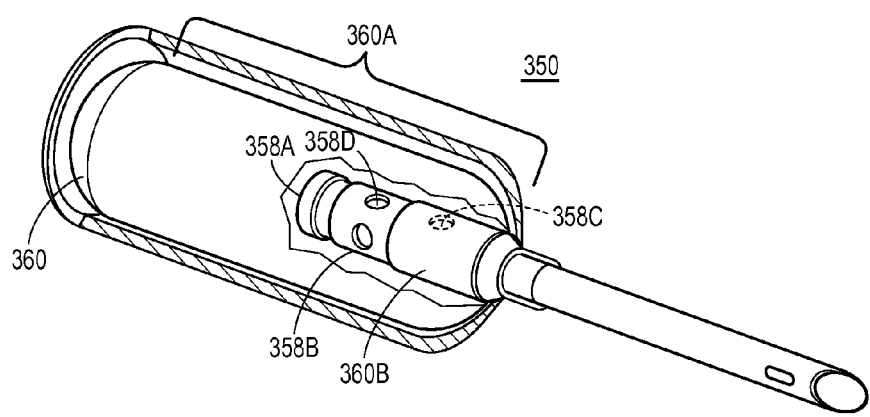
Figure 3F:
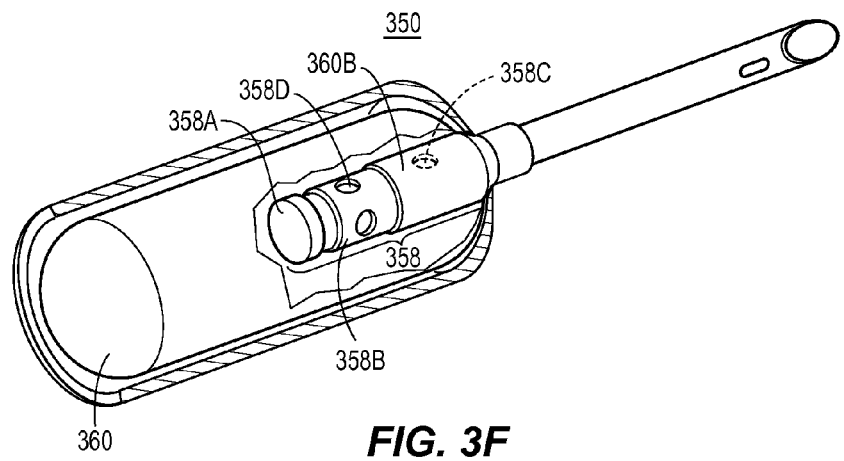

FIGS. 3D-F illustrate an alternative embodiment of a syringe assembly 350 including a needle or cannula 352, a hub/head 354, a barrel or body 356, a slider assembly 358, and a pouch 360. The slider assembly 358 may include a slider body 358A and a slider frame 358B (e.g., a cage). The slider frame 358B may be a hollow cylinder having inner diameters sized to receive the slider body 358A at one end of the slider frame 358B and the cannula 352 at the opposite end of the slider frame 358B. The slider body 358A and the slider frame 358B may each include a plurality of holes. The slider frame 358B may include a filling hole 358C and a purging hole 358D, while the slider body 358A may include a purging hole 358D. The pouch 360 may include a pouch body 360A and a pouch neck 360B. The pouch 360 may be made of latex, rubber, or other flexible material to act like a bladder or balloon to hold a payload within the syringe body 356. The pouch neck 360B may be stretched to fit over a portion of the slider assembly 358. In some embodiments, the pouch neck 360B is sized to fit in sealing relation against a corresponding sealing surface such as the cannula or a slider assembly 358. The pouch neck 360B may be fitted over the filling holes 358C of the slider assembly 358 to create a seal between the filling holes 358C and the interior of the pouch body 360A and the interior of the cannula 352.

Figure 3G:
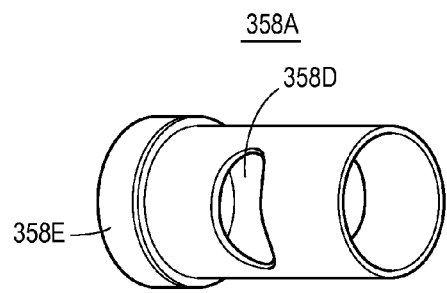
Figure 3H:
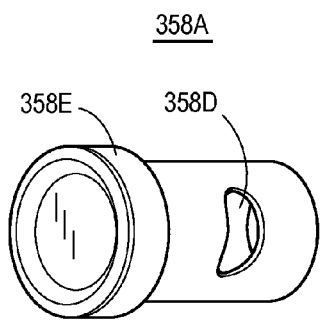
Figure 3I:
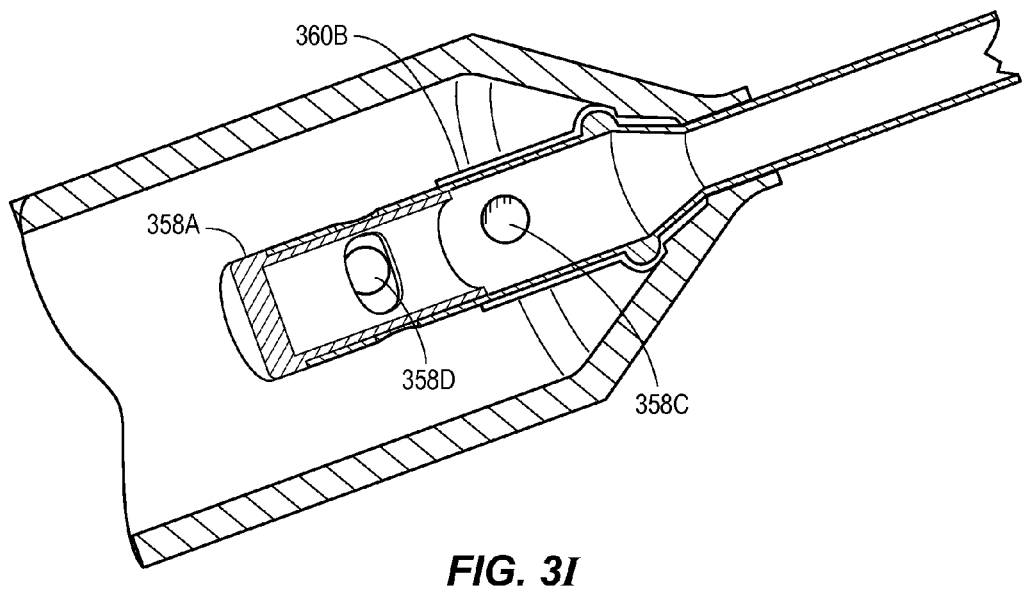

With reference to FIG. 3G, the slider body 358A may include one or more slider body purging holes 358D and a weight cap 358E. The slider body purging holes 358D may be positioned on the slider body 358A to close the slider assembly purging holes 358D in a closed first position and open the slider assembly purging holes 358D in an open second position. For example, FIGS. 3D-F illustrate the slider body 358A in a closed first position where the weight cap 358E is positioned a distance D from an opening of the slider assembly 358. In this first position, the slider body purging holes 358D are not aligned with the slider frame purging holes 358D. In contrast, FIG. 3I illustrates the slider body 358A moved to an open second position with the weight cap 358E positioned directly against the opening of the slider assembly 358. In this open second position, the slider body purging holes 358D are aligned with the slider frame purging holes 358D. In some embodiments, the slider body 358A may be moved into the open second position by the force of impact with a target. The weight cap 358E may be increased or decreased in size and weight to account for varying forces during firing and impact with the RTS 100 and to assure that the slider body 358A will move to the open second position in response to impact with a target.

While filling the pouch assembly, the slider body 385C may be positioned within the opening of the slider body assembly 358 such that the slider body purging holes 358D are not aligned with the slider frame purging holes 358D (e.g., the closed first position described above). During filling of the pouch assembly 360, a positive pressure at the slider assembly filling holes 358C behind the pouch neck 360B may be caused by a payload being forced into the cannula 352 and pushing through the filling holes 358C against the pouch neck 360B. Once the filling pressure exceeds the ability of the pouch neck 360B to maintain its seal between the filing holes 358C and the interior of the pouch body 360A, the payload may enter pouch body 360A. The pouch body 360A may be filled with a payload to a pressure that allows the payload to be purged from the body through the purge holes 358D in an even manner and into a target, while maintaining a seal over the filling holes 358C. In some embodiments, the pouch 360 may be filled to a pressure adequate to express the payload from the exit ports upon impact. The pressure within the pouch may be between 5 and 20 Newton-meters, or approximately 3 to 15 foot-pounds.

Where the syringe assembly includes the slider assembly 358 (e.g., FIGS. 3D-I), the bevel tip 362 of the cannula 352 may be hollow. Further, the sealing relation between the cone assembly fore-end ring 210 (FIGS. 2A-N) and the area of the cannula surrounding the exit port need not provide a seal barrier for the payload. In particular, when the pouch is filled, the pressure within the pouch body 360A and the seal between the pouch neck 360B and the filling holes 358C may keep any payload from leaking out of the cannula tip.

Furthermore, the cannula 302 and/or the cannula 352 may include a floating assembly to seal the syringe body and payload from the cannula. A floating assembly may provide a seal between the cannula and the syringe body payload area. Upon impact, the cannula may be driven toward the syringe body, causing the cannula to pierce the seal. The payload may then be released into the target though the cannula. For example, a spring assembly may suspend the cannula 302, 352 a distance from the seal and the impact force may compress the spring, causing the cannula to pierce the seal.

In another embodiment, the syringe assembly may include a needleless syringe. For example, rather than expressing the payload through a cannula 302, 352, the payload may be expressed by compressed gas or other type of force into the target without a cannula. Where the target is an animal, the syringe assembly may express the payload as a high-pressure jet though the animal's hide without the aid of the cannula, as described above, and where the target has thin skin with little hair the pressure would be less. In some embodiments, the needless syringe may employ a burst of high-pressure gas to propel the payload into the target. In other embodiments, the syringe may be equipped with a Lorentz-force actuator that may be tuned to control the depth of the injection into the target.

Figure 4A:
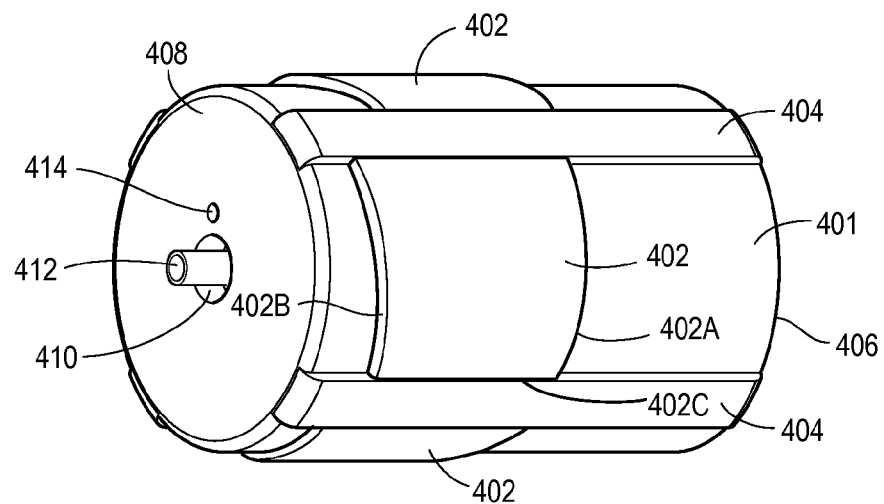
FIGS. 4A, 4B, 4C, and 4D are various views of a fins-cup assembly.
Figure 4B:
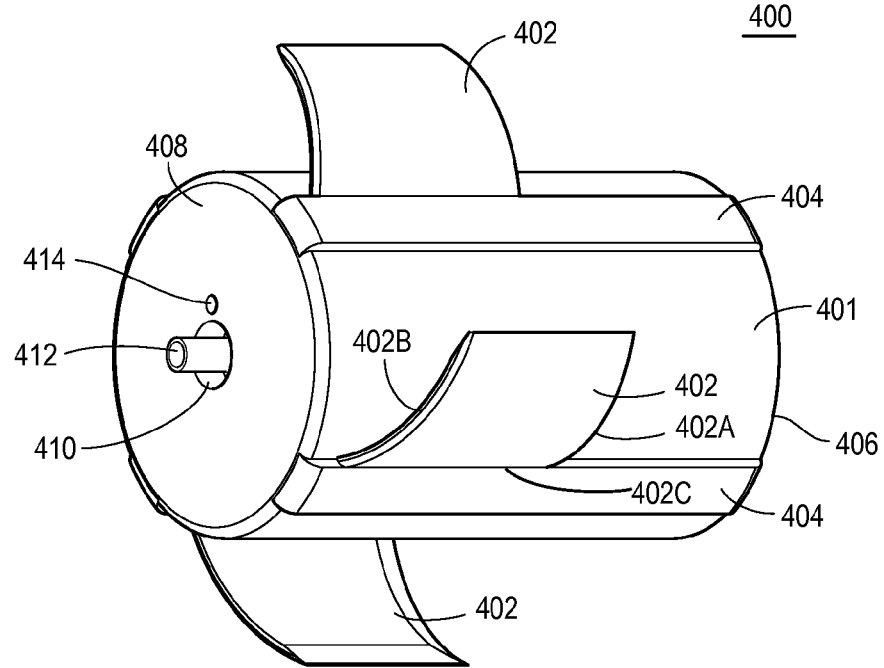

FIGS. 4A and 4B illustrate one embodiment of a fins-cup assembly 400 that may be employed with the syringe assembly of FIGS. 3A, 3B, and 3C. The fins-cup 400 may include a hollow cylindrical body 401 and a stabilizing means 402. An inner diameter of the body 401 may be sized to receive one or more of the syringe open end and plunger assembly 307. In some embodiments, the hollow cylindrical body 401 may be sized to extend longitudinally along the syringe body 306 (FIG. 3A). For example, in various embodiments, the body 401 may extend anywhere from just beyond the syringe open end 306 to the base of the cone assembly 211B (FIG. 2A). In some embodiments, the stabilizing means includes a plurality of fixed fins or a plurality of hinged stabilizing fins 402 to spin or stop spin, each of which is molded integrally with the fins-cup assembly 400 or molded separately and attached to a fins-cup rib 404. While the drawing figures illustrate a fins-cup 400 having four stabilizing fins 402 and ribs 404, the fins-cup 400 may include any number of fins 402 to stabilize the RTS 100 during flight to a target (e.g., two, three, etc.). The fins 402 may each include a leading edge 402A, a trailing edge 402B, and a base 402C. The fins 402, ribs 404, and body 401 may be molded in a single piece or as separate components. At rest (i.e., before being pressed against the body 401 or during flight), the fins 402 may project outwardly from the fins-cup body 401. The fins 402 and ribs 404 may be sized and spaced around the fins-cup 400 such that, when the fins are pressed against the fins-cup body 401 (i.e., when the projectile assembly 150 is inserted within the wad 600), the fins 402 and ribs 404 present a smooth, uniform circumference around the fins-cup 400, as shown in FIG. 4A. The trailing edge of the fins 402 may be angled so that the fins-cup assembly 400 may be twisted to fit into the wad 600. In one embodiment, the bases 402C of the fins 402 are parallel to each other against their ribs 404 to prevent spinning of the projectile assembly 150 during flight. In another embodiment, the plurality of fin bases 402C are uniformly angled against their ribs 404 so that the projectile assembly 150 spins during flight.

The fins-cup body 401 may include an open end 406 and a closed end 408. The open end 406 may receive the syringe assembly 300 while the closed end 408 may include a filling valve 410. The filling valve may be molded integrally with the fins-cup body 401 or may be a separate element that is fixed in a sealing relationship to the closed end 408. The filling valve 410 may include a valve body 410A and a valve stem 410B. In some embodiments, the valve 410 includes a poppet valve that may operate using an axial force against the valve stem 410B to allow a fluid (e.g., a gas such as air or $CO_2$) to enter into the interior of the fins-cup body 401. The closed end 408 may also include a release valve 414. The release valve 414 may release any pressure over an amount required to move the plunger assembly 307 down the syringe body 306 to express the payload from the exit ports 310 upon impact (e.g., 10 to 15 Newton-meters or approximately 7.3 to 11 foot-pounds). In some embodiments, pressure exerted by a gas entering the valve 410 may provide a force within a volume bounded by the fins-cup closed end, the fins-cup body, and the plunger assembly. The force may bias the plunger assembly 307 against the payload within the syringe body 306 so that the payload may be expressed from the syringe body 306 once a seal (i.e., the fore-end ring 210A) slides from the extended first position along the cannula 302 toward the hub/head 304 to the retracted second position and is no longer in a sealing relation to the exit ports 310 in response to impact. To inject a gas or other pressurized fluid through the valve 410, the valve stem 412 may be fitted with a compact bicycle tire pump, electric compressor, a carbon dioxide cartridge, one or more pills or capsules containing a chemical that may break upon impact to react with another chemical to form an expanding gas within the syringe body, or other device. In embodiments that do not include the plunger assembly 307, the valve 410 may be a one-way valve to prevent any payload within the syringe body 306 from leaking, but allow air to enter the body 306 to allow the payload to be expressed from the body 306 through the exit ports 310.

Figure 4C:
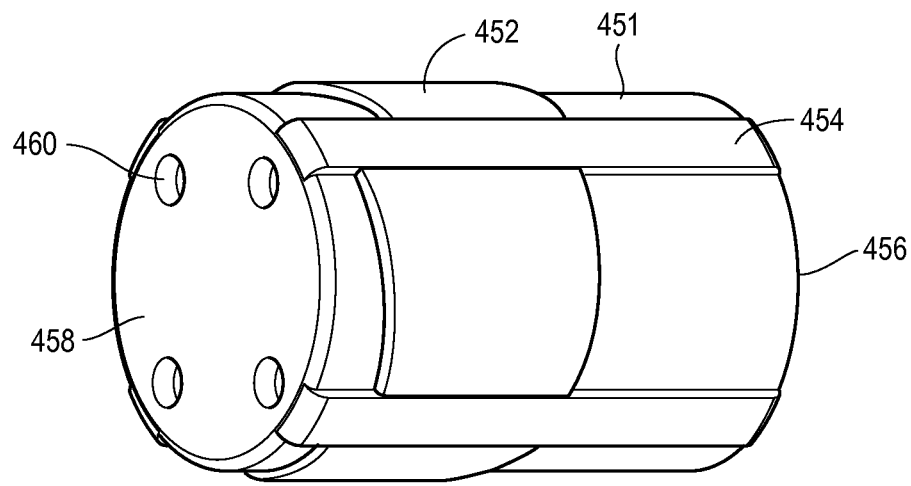
Figure 4D:
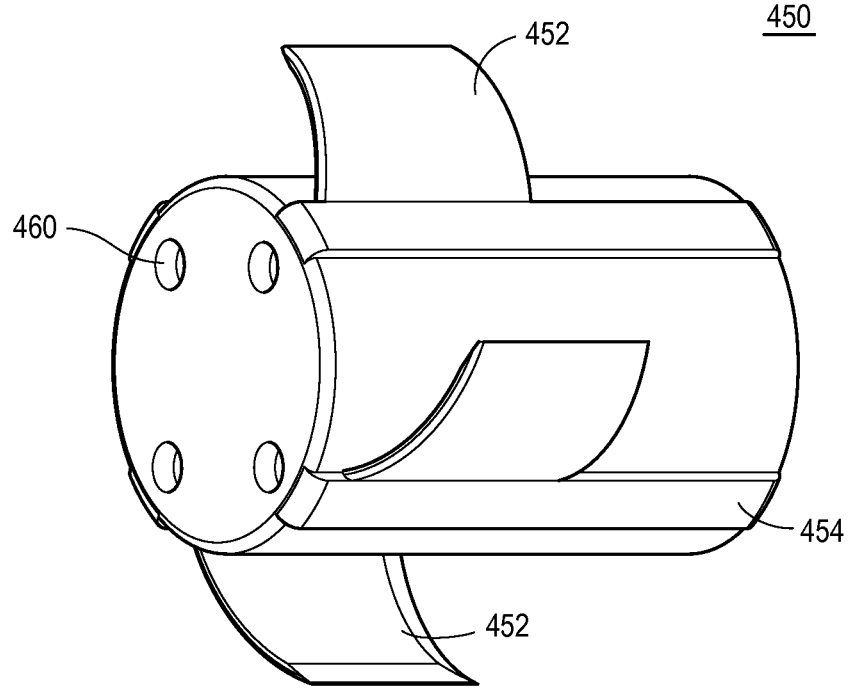

FIGS. 4C and 4D illustrate an alternative embodiment of the fins-cup assembly 450 that may be employed with the syringe assembly of FIGS. 3D-I. The fins-cup 450 includes a body 451 and a plurality of hinged stabilizing fins 452, each of which is attached to a fins-cup rib 454. The fins-cup body 451 may include an open end 456 and a closed end 458. The fins-cup 450 is designed to extend partially along the length of the syringe, however in other embodiments, the fins-cup may extend along the length of the syringe at a further distance, or alternatively, a closer distance to the cone assembly. The closed end 458 may include one or more vent holes 460. When joined, the fins-cup 450 and syringe body 356 form an airtight seal. The vent holes 460 may allow the pouch 360 of the syringe assembly 350 to expand and contract within the syringe body 356 as the payload enters and exits the syringe assembly 350.

Figure 5A:
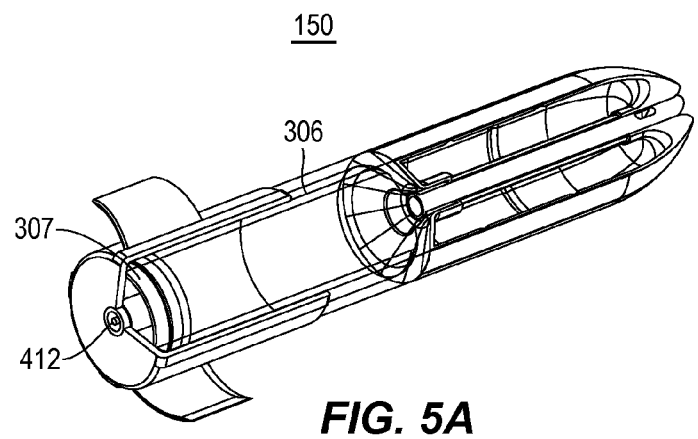
FIGS. 5A, 5B, 5C, 5D, and 5E illustrate perspective views of various embodiments of the projectile assembly.
Figure 5B:
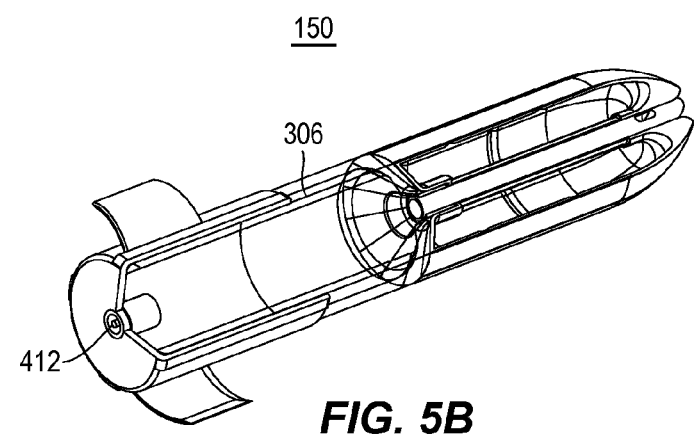
Figure 5C:
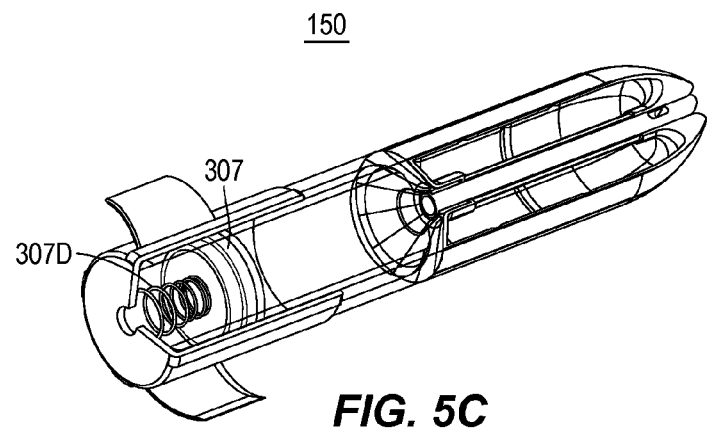
Figure 5D:
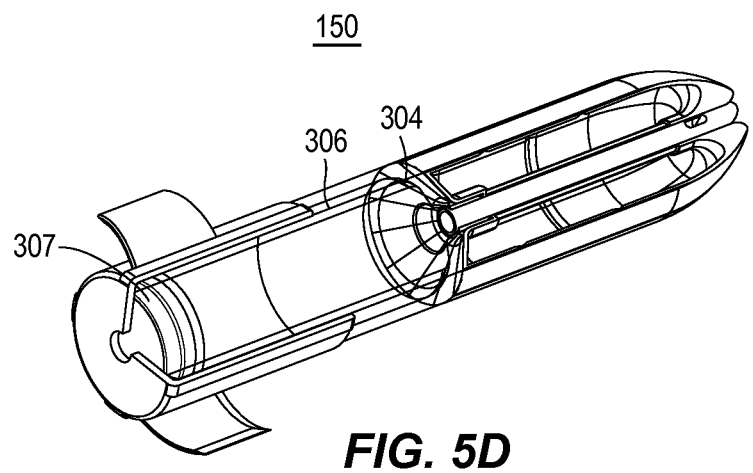
Figure 5E:
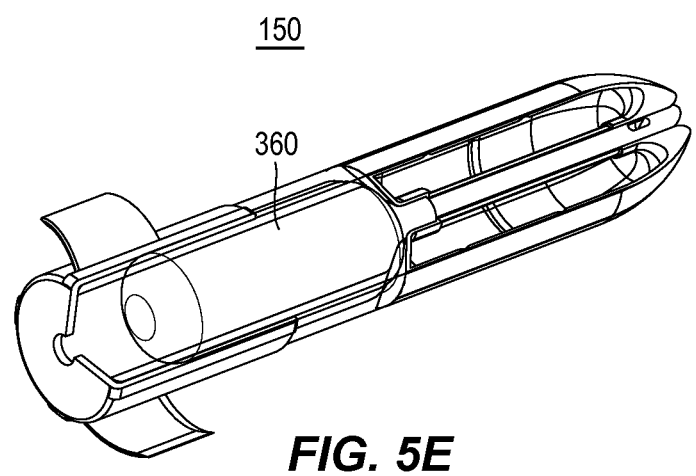

FIGS. 5A-E illustrate various embodiments of the projectile assembly as herein described, with different components to express the payload from the cannula upon impact with a target. FIG. 5A illustrates a projectile assembly having a valve 412 and plunger assembly. As described above, the valve may be used to introduce a gas (e.g., air, $CO_2$, etc.) behind a plunger assembly 307 (FIG. 3) to increase pressure within the syringe body 306. FIG. 5B illustrates a projectile assembly having a valve 412 without any plunger assembly. The valve 412 may be used to introduce a gas to increase a pressure within the syringe body and express the payload from the cannula upon impact. FIG. 5C illustrates a projectile assembly including a plunger assembly 307 and coil spring 307D. The spring may bias the plunger assembly within the syringe body against the payload to also increase a pressure within the syringe body and express the payload from the cannula upon impact. FIG. 5D illustrates a plunger assembly 150 having a plunger assembly 307 within the syringe body 306. Upon impact, the momentum of the plunger assembly 307 within the syringe body 306 may cause the plunger assembly 307 to move toward the hub/head 304. Movement of the plunger assembly 307 upon impact may increase a pressure within the syringe body and express the payload from the cannula upon impact. FIG. 5E illustrates a projectile assembly 150 having a pressurized pouch assembly 360. Though not illustrated in FIG. 5E, but instead illustrated in FIGS. 3D-3I, the projectile assembly 150 can also include a slider assembly 358. Upon filling the pouch assembly, the sealed pouch assembly 360 may have a positive pressure compared to the atmospheric pressure surrounding the projectile assembly 150. Upon impact, the slider body 358A moves forward within the slider frame 358B and the payload is expressed though the cannula by the positive pressure.

Figure 6:
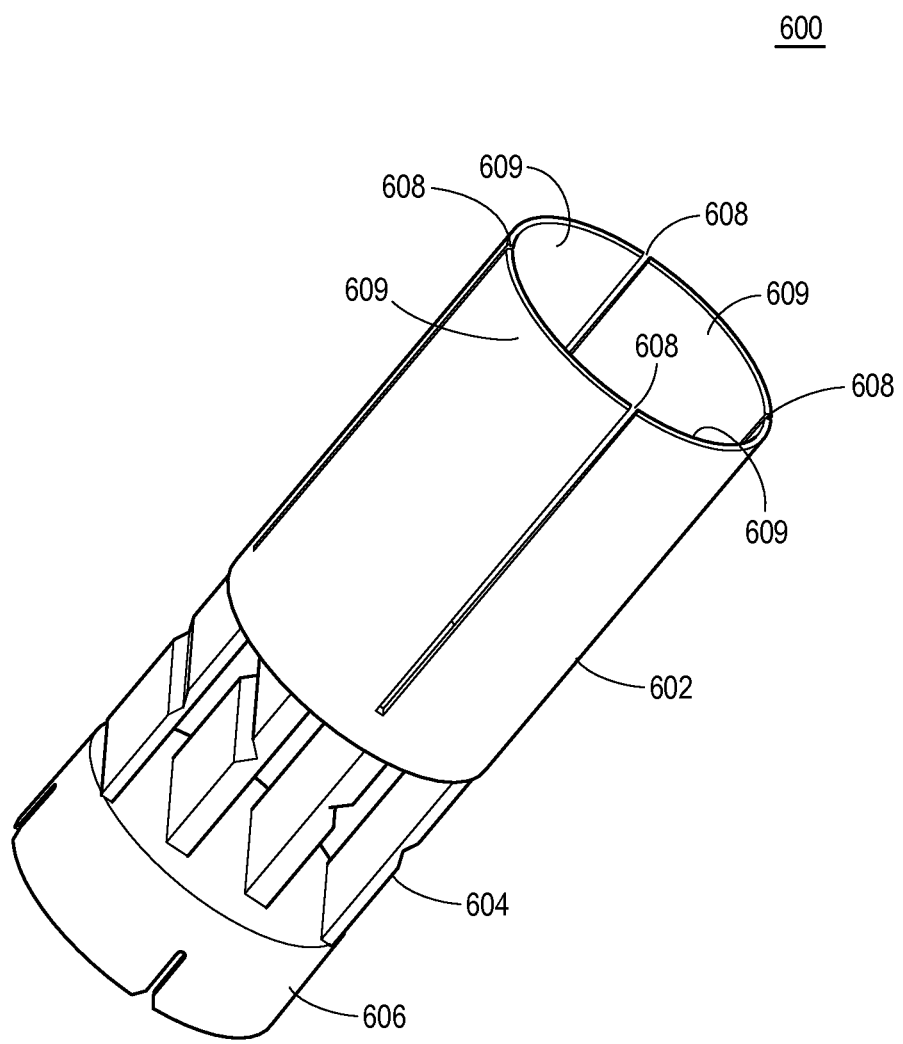
FIG. 6 illustrates a wad assembly.

FIG. 6 illustrates a wad assembly 600 of a shotgun or slug-gun shell into which the projectile assembly 150 may be fitted. The wad assembly 600 may include a skirted or non-skirted wad cup. In some embodiments, the wad assembly 600 may include a casing 602, a wad 604, and a wad cup 605 with skirts 606. The wad 604 may be made of straight parts with thin sections that bend under compression. When fitted to the projectile assembly 150, the wad casing 602 may extend along a length of the projectile assembly 150 to stabilize the projectile assembly as it travels along the length of the firearm barrel upon firing. The wad 600 may include an opening having an inner diameter sized to receive an outer diameter of fins-cup assembly 400, 450 in a sealing relation. In some embodiments, the wad casing 602 may extend to any point along the projectile assembly 150 from the fins-cup assembly closed end 408, 458 to the ogive of the cone assembly 200 or beyond. The wad assembly 600 may be made of a resin such as polyurethane or other type of flexible plastic material. For varying ranges of the RTS 100, the wad 600 may be made with materials of varying rigidity. For example, a longer-range RTS 100 may require a highly rigid wad to ensure most of the charge energy is transferred to the projectile assembly 150. While the wad assembly 600 shown in FIG. 6 includes a skirted wad cup 605, other types of wad cups may be employed (e.g., a fiber, felt, or cardboard disk, nitrocellulose, etc.). The wad assembly 600 also includes slits 608 which define wad sections 609 which aid in releasing the projectile assembly 150 from the wad assembly 600 by expanding and increasing the air resistance of the wad assembly 600 over the projectile assembly 150 once the wad carries the projectile assembly 150 out of the firearm barrel.

Figure 7:
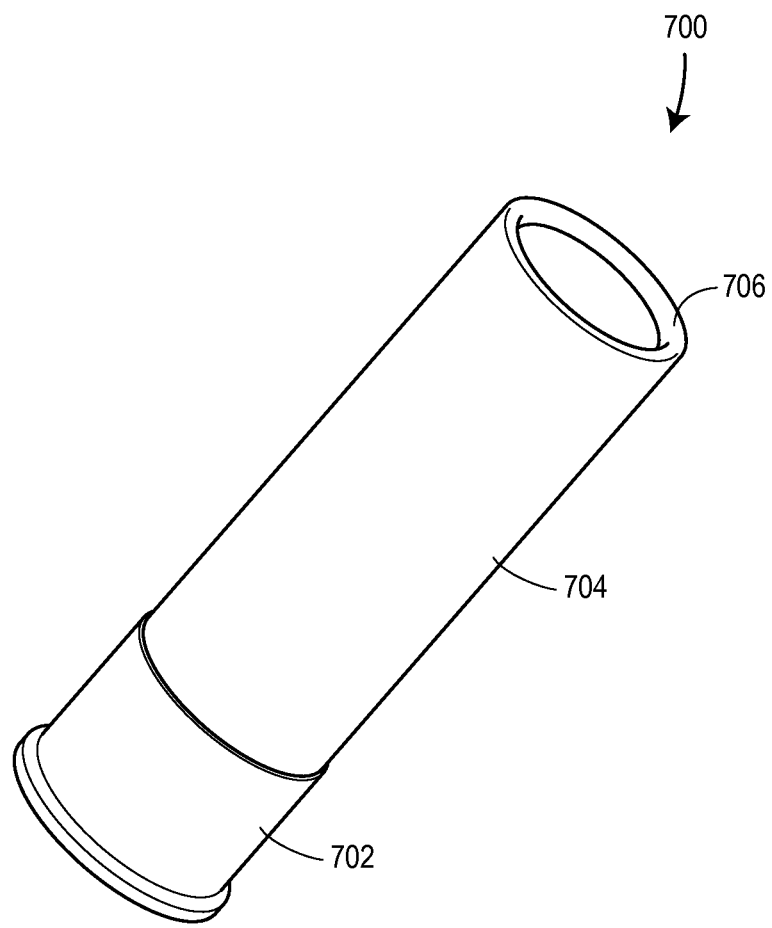
FIG. 7 illustrates a shell.
Figures 8A, 8B, 8C:
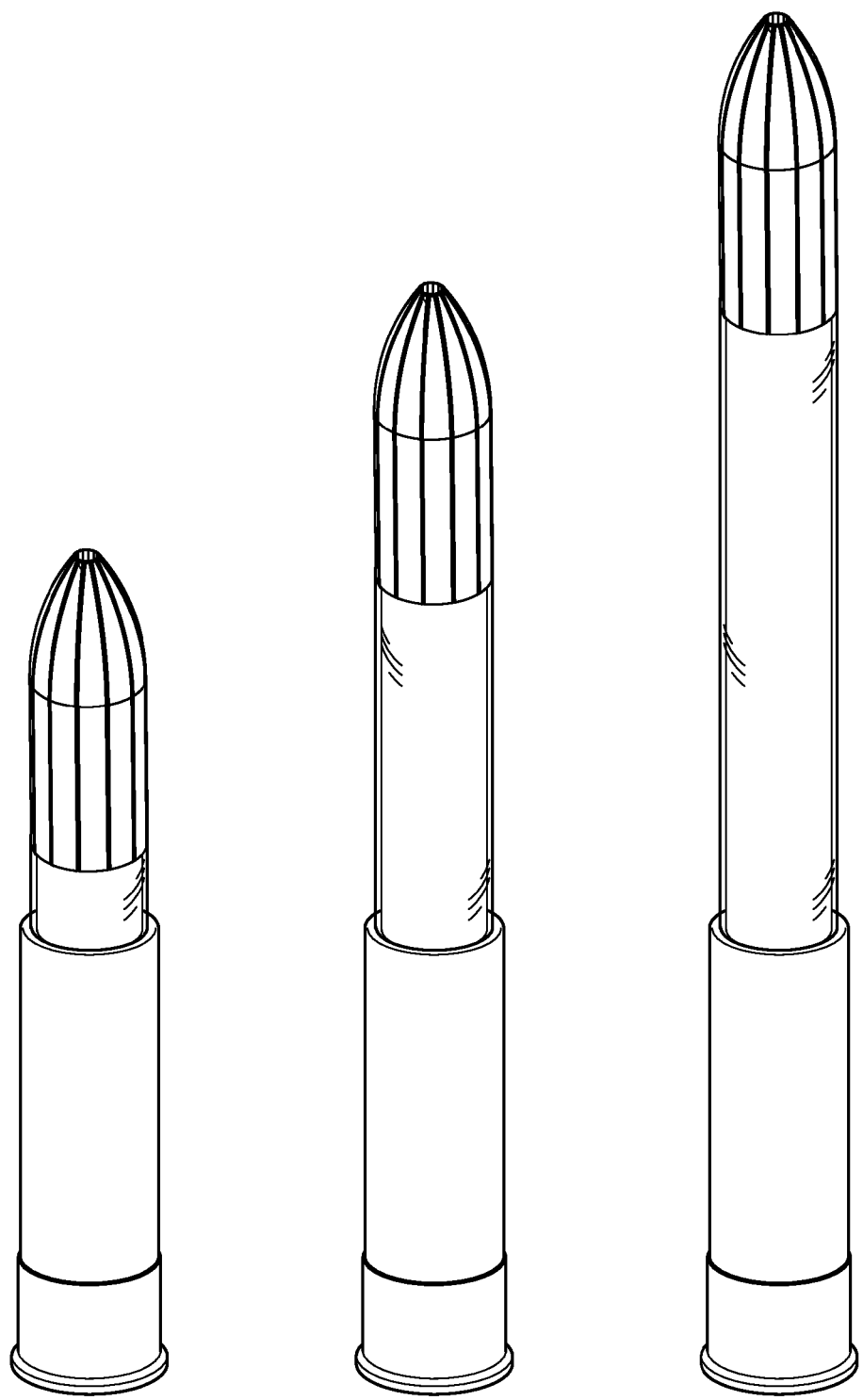
FIGS. 8A, 8B, and 8C illustrate various sizes of a remote treatment system.

FIG. 7 illustrates a shell 700 including a head 702 and a case 704. The case 704 includes a seal 706 which holds the wad 700 in place inside the shell 700. The shell 700 may include a standard 2.75 inch shell, or a longer 3 or 3.5 inch shell, or longer lengths to accommodate various length projectile assemblies. In some embodiments, the seal 706 includes a roll crimp 606 that includes a portion of the case 704 that is formed into a roll covering a leading edge of the wad 600. In other embodiments, the seal 706 may include a fold crimp or other method of holding the wad assembly 600 within the case 704. The head 702 may include a charge or gunpowder that, using the firearm, is ignited by a primer. The amount of charge may vary according to the distance and type of projectile assembly 150. In some embodiments, the head 702 may be a "half-head" type. The amount of gunpowder may vary according to distance and type of projectile assembly 150. For example, as shown by FIGS. 8A-C, a syringe body 306 may be extended to hold varying amounts of payload that require more or less energy and, thus, charge for the projectile assembly 150 to reach the target. The size of the charge may be adjusted to achieve a flight speed of the projectile that is less than the speed of sound (i.e., 348.2 m/s at sea level), e.g., a flight speed that is under the transonic zone (approximately 274.32 m/s at sea level). The size of the charge may arrive at the target at approximately 30.48 m/s, with the range of the projectile assembly 150 being between 10 and 200 meters. However, embodiments of the projectile assembly 150 as herein described may be used with a charge to achieve greater velocities (e.g., supersonic) and, thus, a greater range.

Figure 9:
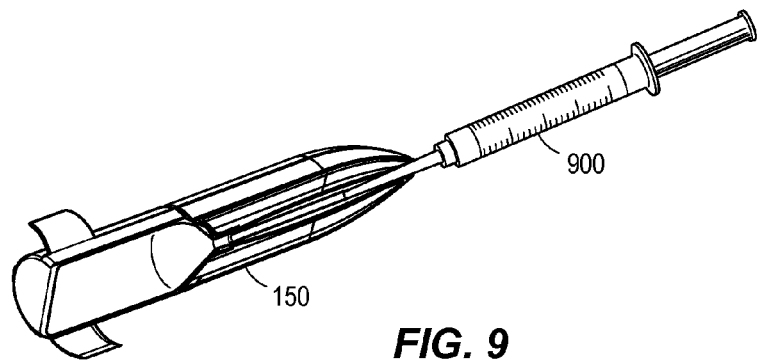
FIG. 9 illustrates a projectile assembly and a filling device for filling a payload area of the remote treatment system.
Figure 10:
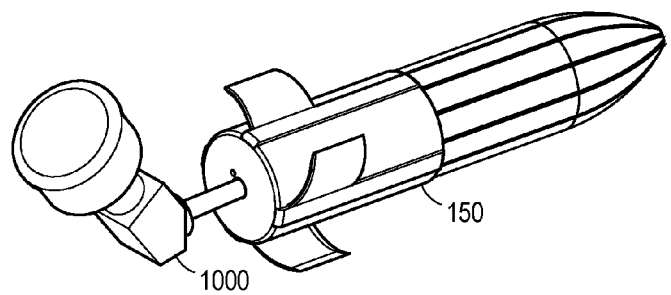
FIG. 10 illustrates a projectile assembly and a pump.
Figure 11:
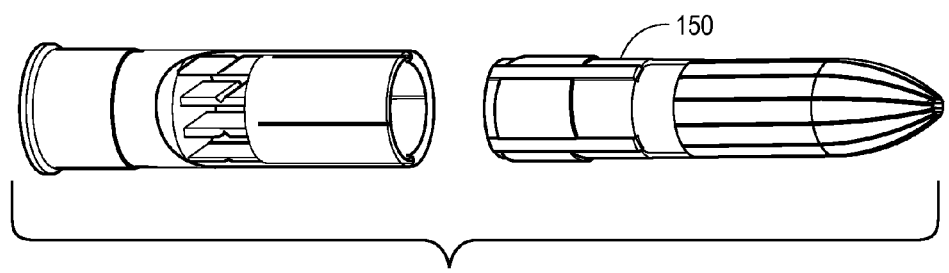
FIG. 11 illustrates a projectile assembly with stowed stabilizing means and a shell.

FIGS. 9-15 illustrate preparation and deployment of the RTS 100. With reference to FIG. 9, a user may compress the cone assembly 200 so that the fore-end ring 210 unseals and exposes the exit port 310. During use, the deformable cone assembly may: a) seal the cannula exit ports, b) deform for filling by moving the fore-end ring toward the hub head to unseal the exit ports, c) reseal by allowing the fore-end ring to spring back toward the bevel tip, d) stay sealed for at least twenty four hours as pressure tries to push the payload out past the exit ports (for the syringe assembly illustrated by FIGS. 3G-I), e) open from the impact kinetic energy that is greater than the pressure that it was able to resist, and f) stay open while the payload is expressed into the target.

Figure 12A:
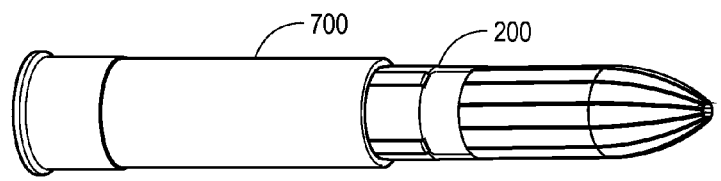
FIGS. 12A and 12B illustrate embodiments of a projectile assembly joined with a shell.
Figure 12B:
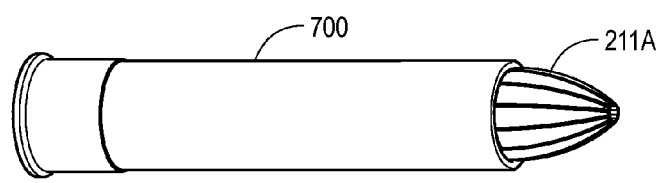
Figure 13:
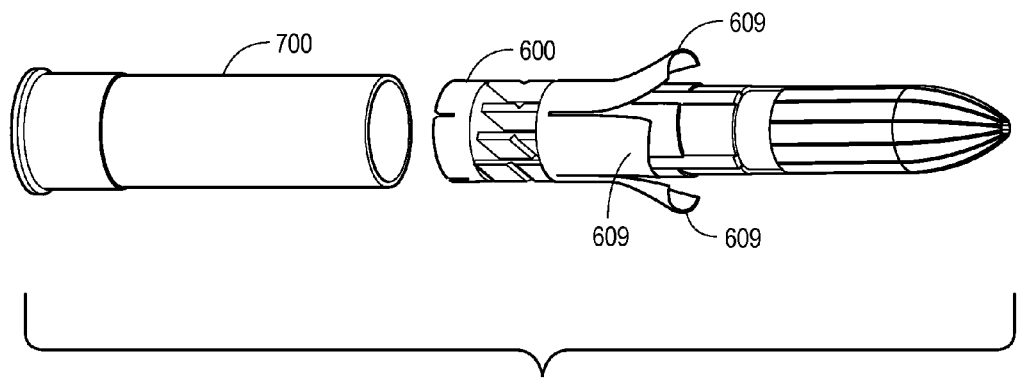
FIG. 13 illustrates a remote treatment system upon firing.
Figure 14:
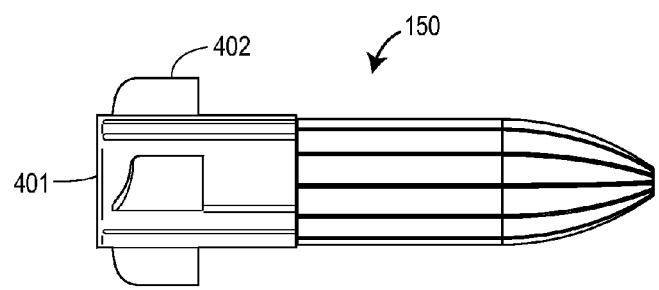
FIG. 14 illustrates the projectile assembly during flight.
Figure 15:
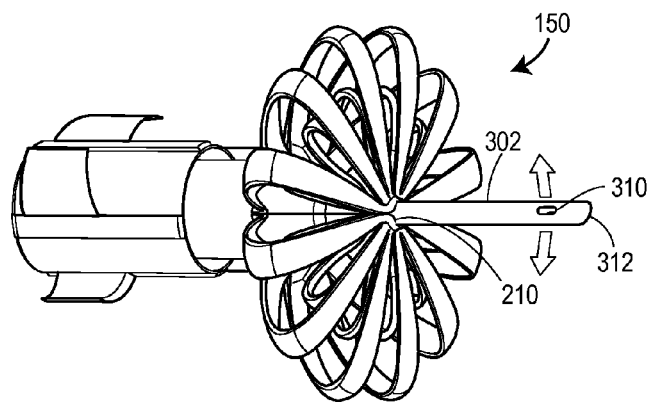
FIG. 15 illustrates the projectile assembly upon impact with a target.

In some embodiments, a filling device 900 may be inserted into the cannula 302 (FIG. 3) of the projectile assembly 150 to fill the payload area of the syringe assembly 300, 350. In some embodiments, a filling device 900 of 20 mL or greater capacity may be inserted into an exit port 310 of the cannula 302 to fill a payload area. The filling device 900 may include a needleless syringe, a syringe fitted with a cannula or soft tube that has a larger diameter than the cannula 302, a syringe fitted with a cannula that is a smaller diameter than the cannula 302, a tube and pump, etc. After filling the payload area, the user may release the cone assembly so that the fore-end ring 210 seals the exit port 310. In other embodiments, the syringe assembly may be filled from a rear filling port or by a device during assembly of the projectile. At FIG. 10, a pressurized fluid dispenser 1000 may be affixed to a valve stem 412 (FIG. 4) of the valve 410 to fill an enclosed or hollow area 307C behind the plunger seal 307A. As described above, the area 307C may be filled to a pressure of approximately 10 to 15 Newton-meters, or 7.3 to 11 foot-pounds to propel the plunger toward the cannula 302 and expel the payload in response to impact with a target. At FIG. 11, the projectile assembly 150 may be fitted into the wad 600. In some embodiments, a twisting motion between a leading edge of the wad and the closed end of the fins-cup assembly may cause the fins 402, 452 to flatten against the fins-cup body 401, 451 and the fins-cup may be inserted within the wad 600. As seen in FIGS. 12A and 12B, the projectile assembly 150 is seated within the wad 600 and the shell 700. As described above, the wad 600 and shell 700 may extend from any point along the fins-cup body 401, 451 to the cone ogive 206 (FIGS. 2A and 2B). FIG. 12A shows the wad 600 and the shell 700 extending to a base of the cone assembly when the projectile assembly is fully seated. FIG. 12A shows the wad 600 and shell 700 extending to a base of the cone assembly and covering the fins-cup assembly 400, 450 when the projectile assembly is fully seated. FIG. 12B shows the wad 600 and shell 700 extending to a base of the ogive 206 on the cone assembly and covering a substantial portion of the cone assembly 200 when the projectile assembly is fully seated. FIG. 13 illustrates part of the RTS 100 upon firing and exiting a firearm barrel. The wad sections 609 (FIG. 6) expand once the wad assembly 600 meets the increased air resistance upon exiting the barrel, causing the wad assembly 600 to fall away from the projectile assembly 150. As illustrated in FIG. 14, the fins 402, 452 extend outward from the fins-cup body 401, 451 once the wad assembly 600 falls away from the projectile assembly. The fins 402, 452 stabilize the projectile assembly 150 while in flight to a target. FIG. 15 illustrates the projectile assembly 150 in response to impact with a target. As described above, the cone assembly 200 is compressed along the cannula 302, moving the fore-end ring 210A from the extended first position toward the hub/head 304 to the retracted second position and the cannula 302 enters the target. Each cone section 202 bends as described above in relation to FIG. 2H, separating the cone sections 202 from each other and releasing a payload from the cone payload area 215. Once the fore-end ring 210A slides below the exit ports 310, pressure within the syringe body 306 or pouch 360 causes the syringe payload to be expressed through the exit ports 310 and into the target. Once the syringe internal pressure is equal to atmospheric pressure at the target, the projectile assembly 150 may fall away from the target.

Figure 16:
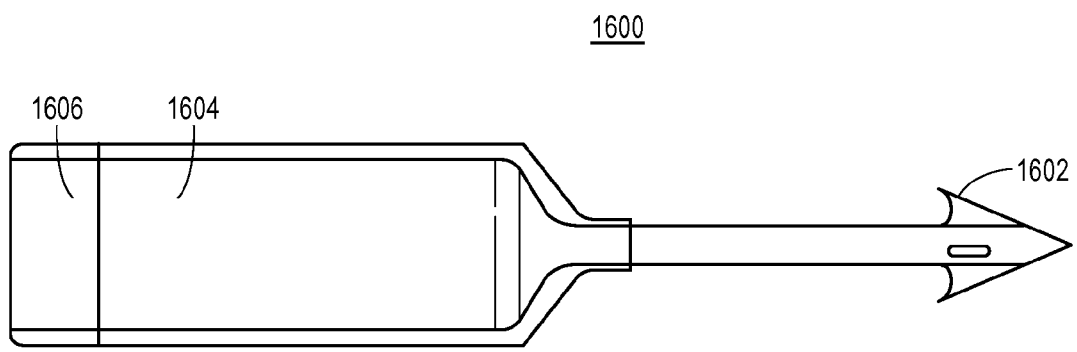
FIG. 16 illustrates an alternative embodiment of a projectile assembly including a barbed hook cannula.

While the projectile assembly 150 described above is generally applicable for intra-muscular delivery of vaccinations, treatments, and inoculants by a twelve-gauge shot or slug-gun or gun of another caliber, the assembly 150 or portions of the assembly may be applicable in other applications. For example, subcutaneous injection, or rather than liquid treatments, inoculants, data and/or tracking system components, the projectile assembly 150 may deliver a payload assembly that includes a device for use with a satellite or radio tracking and information system (e.g., a global positioning system (GPS) locator, an IRIDIUM satellite constellation link microchip, a radio transmitter, a radio frequency identification chip, etc.). Likewise, with reference to FIG. 16, a syringe assembly 1600 cannula may include a barbed hook 1602, with which the RFID and other technologies may hang from the target allowing for externally applied location, tracking, and data harvesting. The payload 1604 may include a transmitting or data gathering device 1604 for use with a satellite or radio frequency tracking and tagging information system. The projectile assembly 150 may implant the barbed hook 1602 in the surface (e.g., skin) of the target without imparting significant, injury-producing shock on the target area. The barbed-hook 1602 may also be self-discarding in that, over time, the hook may work its way out of the target's skin after tracking or data-gathering activities have been concluded. Further, the tracking device 1604 may include a floatation device 1606 that permits recovery of the tracking device in water should the target be found in a marine habitat.

Figure 17:
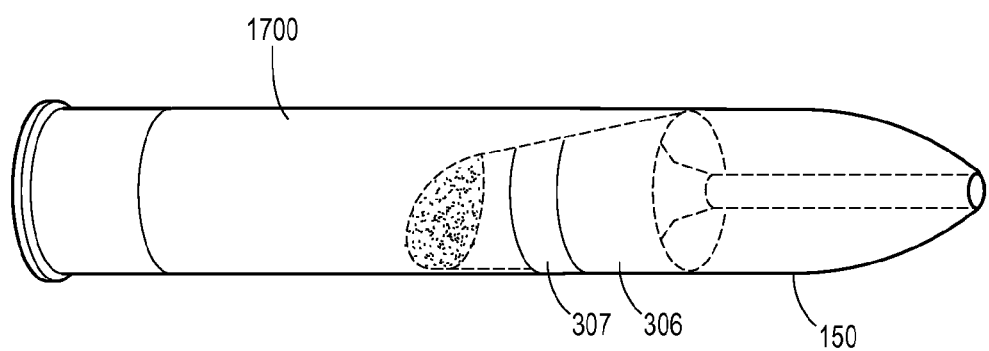
FIG. 17 illustrates a rifle-deployed embodiment of a remote treatment system.
Figure 21A:
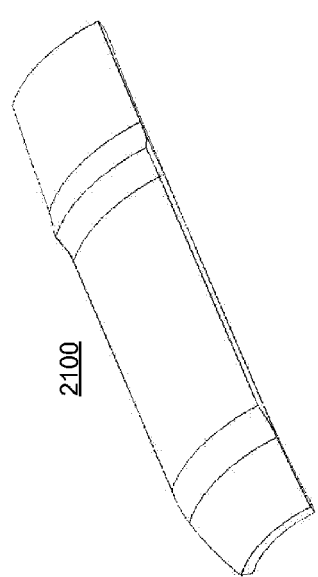
FIGS. 21A, 21B, and 21C are various views of a gourd rib.
Figure 21B:
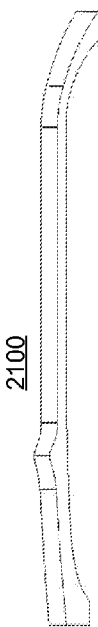
Figure 21C:
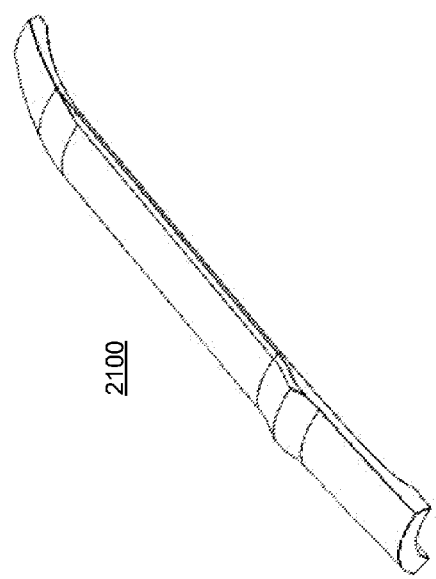
Figure 20C:
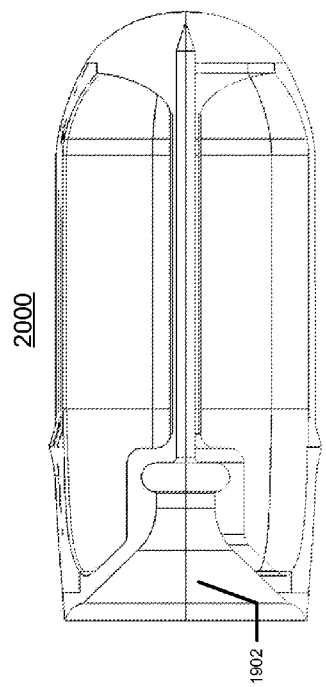
Figure 20D:
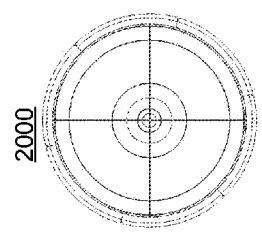

With reference to FIG. 17, the projectile assembly 150 may be sized for delivery systems other than a standard shot or slug-gun. For example, a projectile assembly 150 may be sized for a large-caliber, sub-sonic rifle cartridge 1700 (e.g., a .45-70 Government cartridge, .50-90 Sharps, .300 Whisper, .500 Phantom, etc.) or other type of rifle cartridge. The smaller syringe assembly 300 of a projectile assembly 150 for such rifle cartridges may be reduced from the 4.5 mL capacity of the syringe assembly 300 described herein. A syringe body 306 for a .45-70 Government-sized projectile assembly 150 may be approximately 2 mL. In some embodiments, a projectile assembly 150 used in a rifle cartridge 1700 may be spin-stabilized rather than fin-stabilized or fin inducing spin stabilized, and may not include both the fins 402, 452 of the fins-cup assembly 400 and the wad assembly 600. In other embodiments, the syringe assembly 300 is removed and the RTS 100 is a frangible projectile that is capable of delivering medicine, vitamins, and other inoculants or treatments to a target.

FIGS. 18-27 illustrate another embodiment of a remote treatment system (RTS) 1800. As shown in FIGS. 18A and 18B, the further RTS 1800 may include a two-part cone 1802, a fins-cup 1804, a piston 1806 within a syringe 1808, and a ventil 1810 that is fitted to the rear-end of the fins-cup 1804, but may be located elsewhere. The two-part cone 1802 may include an inner spine 1812 and an outer gourd 1814. The outer gourd 1814 includes a plurality of supporting ribs 1816 and the inner spine 1812 may include a cone spine nose 1813 that may be made as a separate part. The fins-cup 1804 may include a driving band 1818 that is dimensioned to fit within the barrel of a shot or slug gun. Likewise, the outer gourd 1814 may include a supporting rib 1820 that is also dimensioned to fit within the barrel of a shot or slug gun.

As generally described above at FIGS. 4A, 4B, 4C, and 4D, and as shown in FIG. 26, the fins cup 2600 may include a plurality of stabilization fins 2602 that fold backward to a recessed area 2604 on the fins cup 1804 and are held in the folded position by a skirted wad 600. Due to a joining means to the cup itself, the fins may be urged to flip outward when released from the skirted wad 600. The recess into which each fin folds flat on the fins-cup may be configured in reverse to the fin profile, so that when held in place by the skirted-wad, the fins cup 1804 may generally resemble a tube without any bulging features. As described above, the fins-cup 2600 may include a driving band 2606 that is dimensioned to fit within the barrel of a shot or slug gun.

Without a crimp on the shell 704 to hold back the wad and to help build up pressure as the gunpowder burns, the syringe assembly 300, 1824 may not gain sufficient velocity upon firing. The driving band 1818 may create a resistance within the gun barrel upon firing. As an additional feature, the position of the driving band 1818 may cause a firing pressure to build gradually against the syringe assembly 1824 upon firing. Further, because the syringe assembly 1824 may generally rest in the skirted wad 600 at a rear end of the assembly 300, 1824, the driving band 1818 may reduce any rocking or oscillation of the assembly 300, 1824 as it runs along the barrel after firing.

A complete cartridge 700 such as the Winchester WAA12 AA White Wads 12-gauge including a skirted wad 600 may be provided to the system 100, 1800 in a plurality of colors each including a different load for various range options. Alternatively, a bespoke wad may be incorporated. Further, the cartridge may not include a folded crimp or roll crimp at an opening 1822.

Turning to FIGS. 19A, 19B, and 19C, the 1900 may also include a hub head 1902 dimensioned to fit into a base of the two-part cone 1802. The syringe may hold a measure of liquid, for example, a drug, inoculant, or payload. In some embodiments, the syringe is dimensioned to hold approximately six milliliters of fluid.

Turning to FIGS. 20A, 20B, 20C, 20D, 21A, 21B, and 21C the cone gourd 2000 forms the outer piece of the two-part cone 1802. The cone gourd 2000 may be made up of a plurality of flexible cone body segments (e.g., gourd ribs) 2100 that are joined together at seams 2002 between the segments 2100. Upon impact with a target, the cone gourd 2000 may burst along the cone gourd rib seams 2002 or the segments 2100 may themselves break or burst. Generally, the segments 2100 give structure to the cone gourd 2000 and protect the gourd 2000 from damage from any buffing against the gun's barrel and a slug-gun's full or partial bore length rifling.

Turning to FIGS. 22A, 22B, and 22C, an inner spine 2200 may include a nose 2202 and a base 2204. The inner spine 2200 may be sectioned as illustrated in FIGS. 22A, 22B, and 22C. The cone-spine forms the inner piece of the two-part cone. The inner spine 2200 may give stability and structure to the two-part cone 1802 so that it is able to withstand the various forces associated with firing the remote treatment system 100, 1800 without bursting before impacting the target. In use, the inner spine 2200 may break whereas the gourd 2000 may burst. The inner spine 2200 may support the nose 2202 so that it may function as the closure to a cannula 302 as well as holding the ballistic profile of the two-part cone 1802 at firing and during flight. The nose may include a sealing member 2206 such that the nose 2202 provides a seal or closure around the cannula 302 when the inner spine members are joined around the cannula 302. In some embodiments, the sealing member 2206 is punctured by the cannula 302 upon impact. The Remote Treatment System 100, 1800 may be closed or sealed by the nose 2202 such that no amount of the payload may escape from the syringe until it impacts the target.

In some embodiments, the cone 1802 may include a cover (e.g., a cone grip) that is placed on the system 100, 1800, until the operator loads his or her shot- or slug-gun. The cover may protect the cone 1802 and stops the cannula from puncturing through the nose 2202. Further, the cover may allow the operator to easily handle and fit the cone 1802 after filling the syringe 1808. The cover may be color coordinated depending upon the color and type of the dye filling inside the cone, and allows the product to be loaded and stored before being deployed by operators.

Turning to FIG. 23, a cannula 2300 may include an adapted injecting Sprotte type cannula designed for lumbar puncture. In one embodiment, the cannula 2300 may be 35 mm in length. The cannula 2300 may be fixed into the hub-head 1902 (FIG. 19). In some embodiments, the cannula 2300 may be fixed to the hub head 1902 with glue or heat. The cannula 2300 may also include a flared rear end 2302 to make fixing the cannula to the hub-head stronger. The cannula 2300 may sit safely but just behind the nose 2202 without piercing the nose 2202 until impacting on and in the target.

Turning to FIGS. 24A, 24B, and 24C, a piston 2400 may be positioned within the syringe 1808 to express a payload from the area 1828 through the cannula 2300 upon impact. In some embodiments, the piston 2400 may be made of a hard resin. The piston 2400 may be sized to fit within the syringe 1808 sealingly with the aid of a plurality of sealing members 2402A and 2402B such as o-rings. The front o-ring 2402A may keep the payload in the front of the syringe 1808. The rear o-ring 2402B may produce a seal for pressuring the piston 2400 against the payload area 1828. A vacuum may be created between the two o-rings, which may assist in keeping the dry area 1826 dry and the wet area 1828 wet, because, a vacuum may be assisting the process in normal rubber plungers. Sides 2404 may be longer than a regular plunger of a normal or standard syringe so that the piston does not tip over when expressing the payload. The sloping fore end 2406 of the piston 2400 may substantially or exactly fit into a sloping fore end of the syringe 1808 up and slightly into the hub-head 1902 and the cannula 2300 (FIG. 23), minimizing air during filling and maximizing the purging of drug along the needle 2300 into the target.

Turning to FIGS. 25A, 25B, 25C, and 25D, a ventil 2500 may provide a rear seal within the syringe such that an area 1826 between the piston 1806 and the ventil 2500 (1810) may be pressurized. In some embodiments, a ratio between the "wet" payload area 1828 capacity and the "dry" area 1826 is 1:1. For example, both the wet area and the dry area may include a volume of 6 mL. The 6 mL dry area may be pressurized to various pressures to expel the payload (i.e., 750 grams of pressure, 1,500 grams, etc.).

In further embodiments, the ventil 2500 includes an inner rubbery part 2502, a ventil-coupling mechanism taking the form of a ventil-button 2504, and an outer skin (not shown) that partially covers the ventil. Some embodiments may only include the ventil 2500 and the ventil-coupling mechanism 2504. The ventil 2500 may include an opening 2506 extending from a rear end to a fore end to allow a user to insert a needle or other apparatus through the ventil into the "dry area" between the piston 1806 and the ventil 2500 within the fins-cup between the ventil and the plunger to pressurize that area. The fore end that faces the rear-end of the piston may have a slit 2508, not a hole, the difference being vital to the closing of the opening through the ventil and allowing it to hold pressure in the area within the fins-cup between the ventil and the plunger or piston. One aspect of this type of ventil is that the dry area pressure actually assists in sealing the button. The button 2504 includes a detail inside its rear end so that a tool bar may hold it; further details regarding the tool bar will be discussed below. Attached to the tool bar, operators may easily fit the button to the Medic, or the ventil 2500 to the fins-cup, out in the field, after filling the syringe though the needle and before pressurizing via the button, even with gloved hands or in low light. In some embodiments, the button may not extend further rearward than the rear most point of the fins-cup because the fins-cup 'plate' is recessed.

FIGS. 27-35 illustrate still another embodiment of a remote treatment system (RTS) 1800. As shown in FIGS. 27A and 27B, the further RTS 2700 may include a two-part cone 2702, a vanes cup 2704 with six vanes, a piston 2710 within a syringe 2708, and a pressure means 2718. In some embodiments, the vanes cup may have more or less than six vanes, and a ventil may be fitted to the vanes cup (not shown). The pressure means 2718 may include a pressurized fluid, spring, or other means. The two-part cone 2702 may include an inner spine 2712 and an outer gourd 2714. The outer gourd 2714 includes a plurality of supporting ribs 2716 and the inner spine 2712 may include a cone spine nose 2713. The nose portion 2713 may be supported by the spine 2712, and the nose portion 2713 may be configured to seal the cone assembly 2702. A cannula (302, 2300) may be in fluid communication with the syringe 2708. The cannula may be at least partially carried by the spine 2712 and seated behind the nose portion 2713. In response to the impact between the cone assembly 2702 and the target, the cannula may be configured to pierce the nose portion 2713 of the cone assembly 2702 and express the payload from the syringe 2708 onto or into the target. The vanes cup 2704 may include one or more vanes 2705 that are sized to an inner dimension of the barrel of a shotgun or slug gun. The gourd 2714 may by likewise sized.

Figure 29:
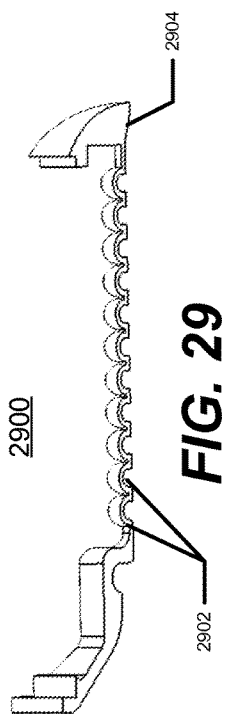
FIG. 29 illustrates a section of a cone spine.
Figure 30:
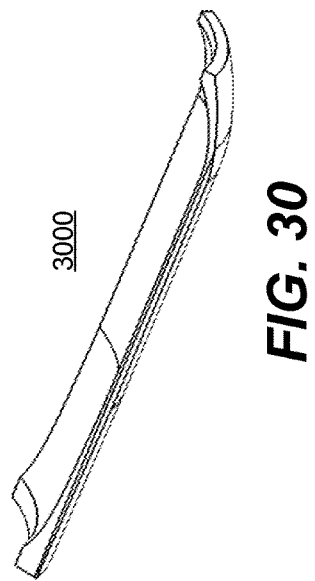
FIG. 30 is a view of a gourd rib.
Figure 28A:
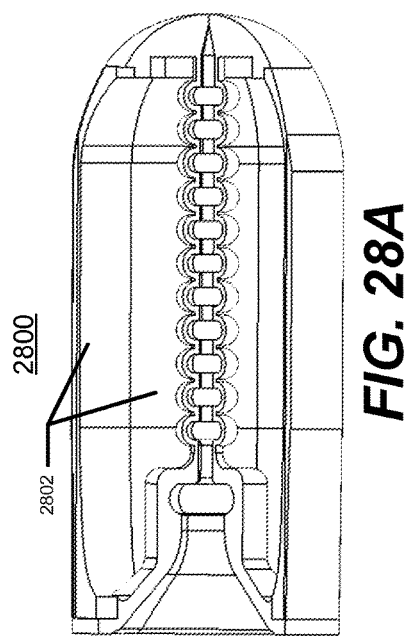
FIGS. 28A and 28B are various views of a further embodiment of a cone assembly.
Figure 28B:
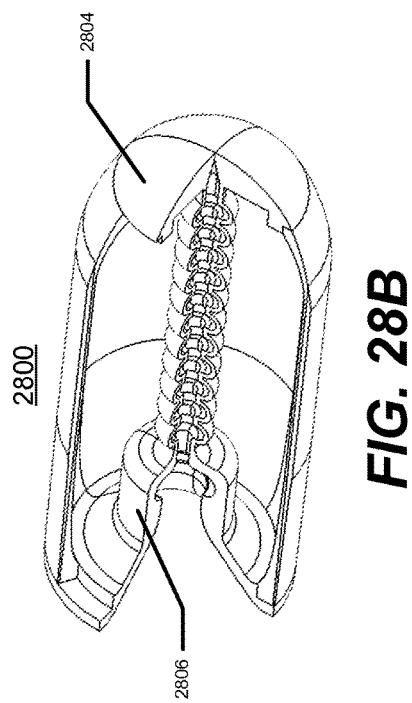

Turning to FIGS. 28A and 28B, the cone gourd 2800 forms the outer piece of the two-part cone 2702. The cone gourd 2800 may be made up of a plurality of flexible cone body segments, e.g., gourd ribs 3000, that are joined together at seams between the ribs 3000. Upon impact with a target, the cone gourd 2800 may burst along the cone gourd rib seams. Turning to FIGS. 29 and 30, an inner spine 2900 may include a nose 2804 and a base 2806. The inner spine 2900 may be sectioned as illustrated in FIG. 29. The spine forms the inner piece of the two-part cone. The inner spine 2900 may be configured to collapse upon impact at the nose 2804. For example, the spine 2900 may be formed by a plurality of joined arches 2902. In use, the inner spine 2900 may collapse whereas the gourd 2800 may burst. The inner spine 2900 may support the nose 2804 so that it may function as the closure to a cannula 302, 2300 as well as holding the ballistic profile of the two-part cone 2702 during firing when the gunpowder burns, and during traveling along a barrel and in flight. The nose may include a sealing member 2904 such that the nose 2804 provides a seal or closure around the cannula 302, 2300 when the inner spine members are joined around the cannula 302, 2300. In some embodiments, the sealing member 2904 is punctured by the cannula 302, 2300 upon impact. The Remote Treatment System 100, 1800, 2700 may be closed or sealed by the nose 2804 such that no amount of the payload may escape from the syringe until it impacts the target.

FIGS. 31A and 31B illustrate a vanes cup (FIG. 31A in partial cross section). The vanes cup 3100 may include stabilization means including a plurality of stabilization vanes 3102. The vanes cup 3100 may have an inner diameter sized to receive an outer diameter of the syringe 2708. The vanes 3102 may be configured to spin-stabilize the assembly 2700 in flight, or may be configured uniformly straight or angled or any other configuration to stabilize the assembly in flight. An outer diameter of the vanes 3102 may also be sized to an inner diameter of a gun barrel such that the vanes cup 3100 is in a sealing relation when inserted to the barrel.

FIGS. 32A and 32B illustrate a sliding, weighted assembly 3200 that is slidably coupled to the vanes cup 3100 and releasingly engages the piston 2710 to bias a pressure means 2718 against applying the pressure against the payload 2720. The sliding assembly 3200 may include an arm assembly 3202 and a weight 3204. The arm assembly may include a plurality of arms 3206 that are affixed to a ring 3208. The weight 3204 may be affixed to a distal end of the arms 3206. The weight 3204 may be affixed to the arms within slots 3210. In one embodiment, the arms 3206 may include on or more affixing means 3212 to attach the weight 3204. Upon impact, the arms assembly 3202 slides toward the cone relative to the vanes cup 3100 and release the piston 2710, such that the pressure means 2718 can apply the pressure against the payload 2720 within the syringe 2708 and the payload 2720 is expressed from the syringe 2708.

Figure 34:
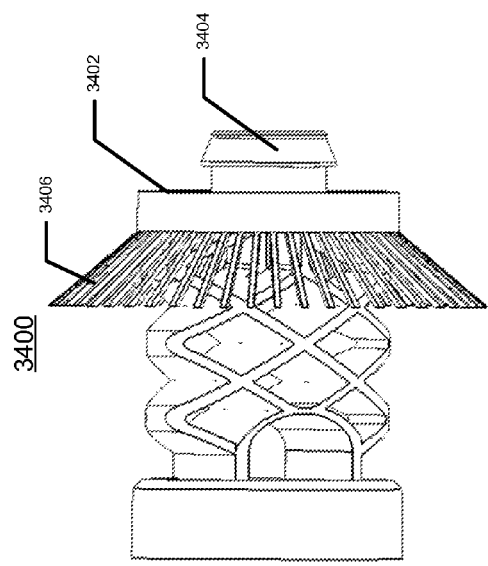
FIG. 34 is a view of a skirted wad.
Figure 35:
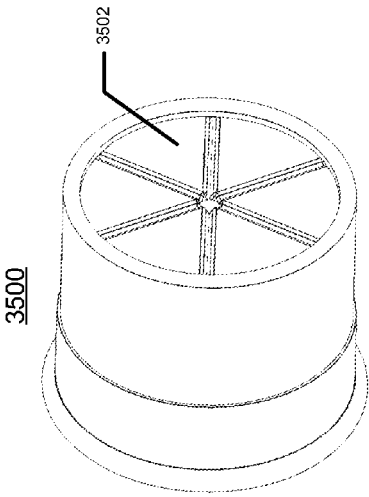
FIG. 35 is a view of a propellant shell.
Figure 33A:
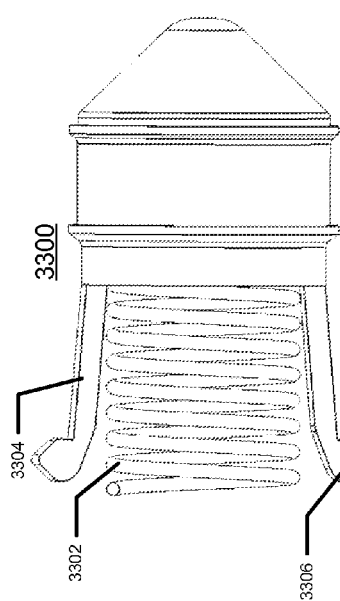
FIGS. 33A, and 33B are various views of another embodiment of a piston.
Figure 33B:
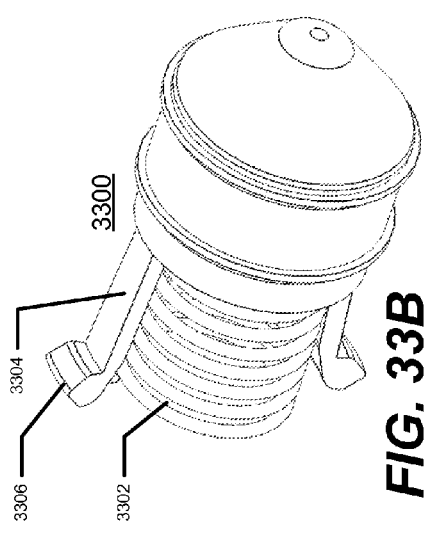
Figure 36A:
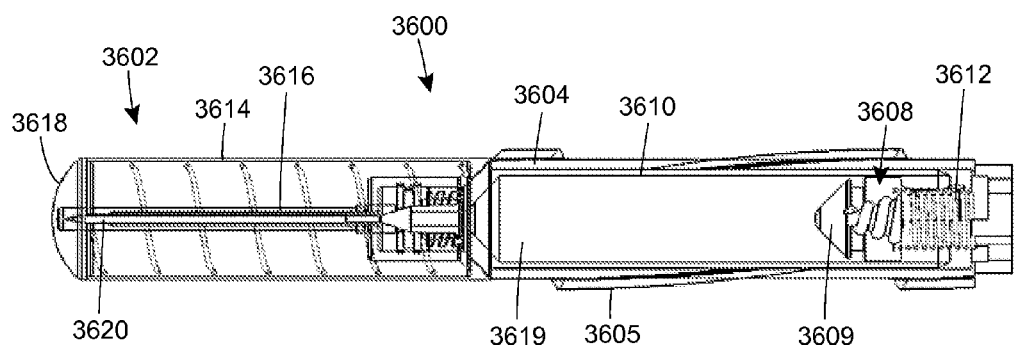
FIGS. 36A and 36B are various views of another embodiment of a remote treatment system having a cone assembly, a vanes cup, a cannula, a piston, and a syringe.
Figure 36B:
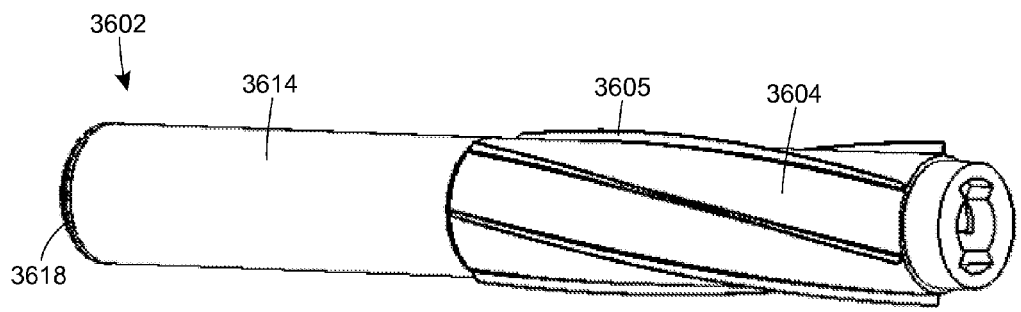

FIGS. 33A and 33B illustrate one embodiments of the piston 3300 and pressure means 3302. The piston may include a threaded hole in its rear area sized to fit a T-shaped, or other shaped, similarly-threaded tool bar. Once the tool bar is affixed to the piston, a user may pull the piston through the vanes cup to pull an amount of fluid into the payload area. The piston 3300 may include one or more firing fingers 3304 having tabs 3306 configured to snap fit into slots (FIGS. 31A and 31B) of the vanes cup 3100. The pressure means 3302 may be biased against a biasing surface 3402 of a wad 3400 (FIG. 34). The wad 3400 in FIG. 34 may also include an affixing means 3404 that is configured to affix the wad 3400 to the base 3106 of the vanes cup 3100. When the piston 3300 is held in the vanes cup 3100 by the tab 3306 and slot 3104 or other affixing means, and when the wad 3400 is then snap fit (e.g., a bayonet, twist, snap fit, or other affixing means) into the base 3106 of the vanes cup 3100, the pressure means 3302 biases the piston 3300 forward toward the cone assembly 2702. The tab 3306 of the piston 3300 firing finger 3304 may fit within the slot 3104 such that when the arm assembly 3202 slides forward upon impact, the ring 3208 of the arm assembly 3202 may bias the firing fingers 3304 inward via the tabs 3306 to release the piston 3300 from being affixed in the slot 3104 and the pressure means 3302 may exert a pressure upon the payload via the piston 3300. Once the cannula 302, 2300 pierces the nose 2804 to expose a cannula outlet 310, 2302, to a lower pressure area than what now exists within the payload area, the higher pressure within the payload area will attempt to equalize, causing the payload to express through the cannula 302, 2300. The wad 3400 may also include a drogue 3406 that may generate a slight amount of drag to slow and stabilize the assembly 100, 1800, 2700. A vent hole through the wad and through the base of the vanes cup 3100 allows a fluid to replace the expressed payload as it leaves the syringe, for example, it allows air to enter the syringe behind the piston so that a vacuum is not created which would otherwise slow or stop the piston purging the syringe payload.

FIG. 35 illustrates one embodiment of a shell 3500. The shell 3500 may include a shortened 12-gauge or similar shotgun shell with a reduced charge. In some embodiments, the shell 3500 includes a fold crimp 3502.

FIGS. 36-46 illustrate still another embodiment of a remote treatment system (RTS) 3600 that can be deployed by a deployment mechanism, as will be described below. As shown in FIGS. 36A and 36B, the RTS 3600 includes a cone assembly 3602, a vanes cup 3604, a piston assembly 3608, a syringe 3610, and a pressure means 3612. The cone assembly 3602 is disposed at a front end of the RTS 3600 and is structured to pierce the hide, skin, or surface of a target and to express a payload held in the syringe 3610. This is facilitated by the piston assembly 3608 having a piston 3609, and, when released, the piston 3609 travels through the syringe 3610 and expels the payload from the syringe 3610 and out of the cone assembly 3602. The vanes cup 3604 structurally frames the syringe 3610, either fully or partially and provides the RTS 3600 with stability and lamination strength as the RTS 3600 travels through the a vacuum or air and/or water toward its target.

The cone assembly 3602 includes a cone body 3614 having an inner spine 3616. A separate or integrated nose portion 3618 may be supported by the inner spine 3616 and may be configured to seal the cone assembly 3602. A cannula 3620, which may, for example, take the form of the cannula 302 or cannula 2300 described above, is disposed within the cone assembly 3602 in fluid communication with the syringe 3610. The cannula 3620 is at least partially surrounded by the inner spine 3616 and seated behind the nose portion 3618. In response to the impact between the cone assembly 3602 and the target, the cannula 3620 is configured to pierce the thin, fore-end nose portion 3618 of the cone assembly 3602 and with the impact release the piston 3609 and thereby the syringe payload from the syringe 3610 onto or into the target. The pressure means 3612 is at least partially disposed within the vanes cup 3604 and is configured to apply a pressure against the payload within the syringe 3610 in response to an impact between the cone assembly 3602 and the target, such that the payload is expressed from the syringe 3610. The pressure means 3612 may include a pressurized fluid, spring, gas, or other means. Once the cannula 3620 pierces the nose portion 3618, exposing a portion of the cannula 3620 to a lower pressure area than what exists within a syringe payload area 3619, the higher pressure within the payload area 3619 will equalize, causing the syringe payload to express through the cannula 3620.

The cone assembly 3602, which is best illustrated in FIGS. 37A and 37B, protects and seals a cone payload, the syringe payload, and enables the RTS 3600 to mark as well as treat the target. As illustrated, the cone assembly 3602 also includes a spiral element 3722 disposed within the cone body 3614 and surrounding the inner spine 3616 and the cannula 3620. The cone body 3614 has a body wall 3724 that is made of the same or similar material as the inner spine 3616, but the body wall 3724 is a different thickness than the inner spine 3616. For instance, the body wall 3724 may be a thin shell composed of a resin or a polymer designed to burst easily upon impact, whereas the inner spine 3616 may be a thicker structure of the same material or similar so as to provide a stiffer, inner support structure. The cone body 3614 may be sized to an inner dimension of a barrel of a shotgun or slug-gun, and may also vary in size according to the length and gauge of the cannula 3620 and/or the target.

A marking material (e.g., a marker dye) or tracking device may be disposed within a space between the body wall 3724 and the inner spine 3616 and sealed within the cone body 3614 by the nose portion 3618. The marking material allows an operator to identify which targets have been treated with the syringe payload or the cone payload itself. For example, upon impact with a target, the body wall 3724 bursts and releases the marking material contained within the cone body 3614 on the target, such that the target can be identified and tracked. The marking material may be a dye of one of a plurality of colors, including industrial standard colors, photo luminescent colors, dyes that are invisible to the naked eye, and customizable forensic traceable liquids that are unique to each customer. Additionally, the marking material may be transferable to mark an object, animal, or person that comes into contact with the marking material, allowing an operator to identify targets that have been marked and/or to tag and track various targets. The cone body 3614 may be transparent to allow an operator to view the contents. Alternatively, the cone body 3614 may be semi-transparent and may include a super bright illuminating LED, e.g., an LED, that may have power for up to twelve hours. To aid in data harvesting and tracking, a programmable Radio Frequency Identification (RFID) or cell phone SIM-card (SIM) tag may be located inside the cone body 3614 until the tag attaches to a target when the cone body 3614 bursts on impact. Using a miniature sender, an operator may be able to communicate with the programmable RFID tag using a smartphone application. The RFID tag may collect and store data related to each deployed RTS 3600 including time and the location of each deployment. Communication between an operator using the smartphone application and the RFID tag may also facilitate RTS 3600 recovery. In another example, a device for filling the syringe 3610 of the RTS 3600 may record and store information regarding the time and location of the RTS 3600 at the time of filling.

The nose portion 3618, best illustrated in FIGS. 38A and 38B, is made of a similar material as the cone body 3614, such as a resin or a polymer, that is very thin at a fore-end of the nose portion 3618 and configured to be easily punctured by the cannula 3620 when the nose portion 3618 makes contact with the target. The RTS 3600 may be closed or sealed by the nose portion 3618 such that no amount of the syringe payload may escape from the syringe 3610 until the RTS 3600 hits the target. The nose portion 3618 may include a drip or seepage discharge sealing member (not shown) configured to grasp the cannula 3620. The sealing member of the nose portion 3618 thus seals the cannula 3620 from seepage of the syringe payload, while also playing a part in isolating the syringe payload from the cone payload marking material contained in the cone body 3614. In some embodiments, the sealing member is punctured by the cannula 3620 upon impact with the target. In other embodiments, the sealing member is gently punctured by the operator when the operator is fitting the cone assembly 3602 over a long cannula 3620 that protrudes past the nose portion 3618. In another embodiment, the nose portion 3618 may have a hole to accommodate a long cannula 3620. The nose portion 3618 may also help to maintain an optimized ballistic profile, for example, by providing thicker side edges where the nose portion 3618 meets the cone body 3614. The optimized ballistic profile would prevent bulging and help maintain the shape. In some cases, the nose portion 3618 may have a color selected based on the marking material carried by the cone body 3614. For example, the nose portion 3618 may be color-coded to match the color of the marker dye filled in the cone body 3614. In yet another example, the nose portion 3618 may display a logo.

Figure 37A:
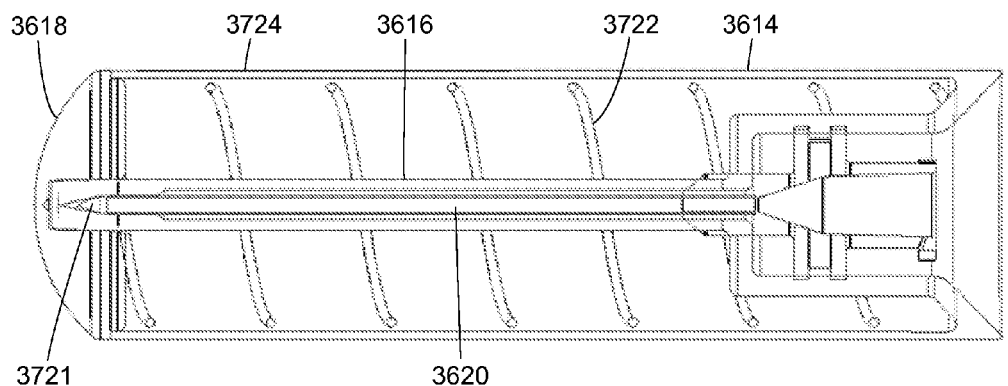
FIGS. 37A and 37B are various views of the cone assembly.
Figure 37B:
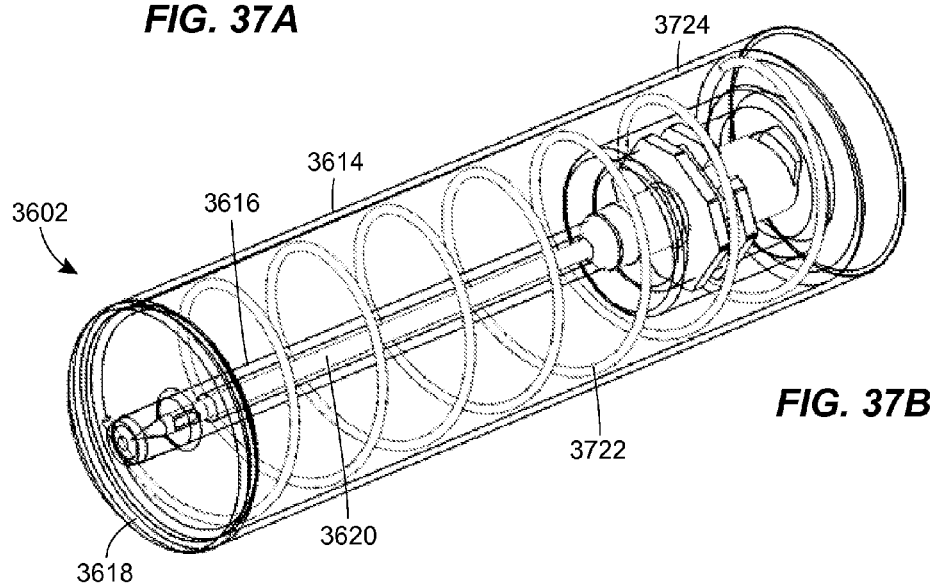
Figure 38A:
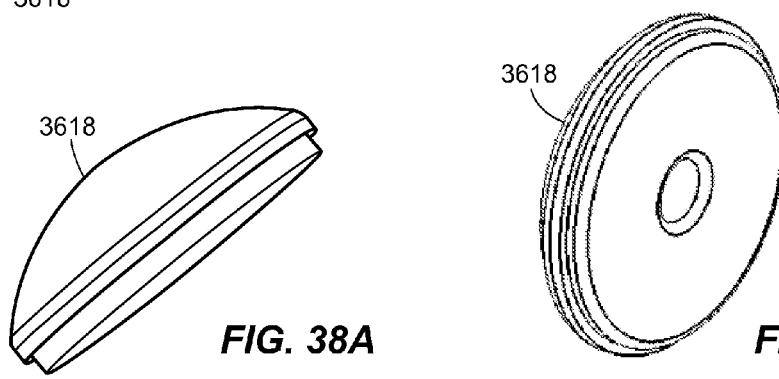
FIGS. 38A and 38B are various views of a nose portion of the cone assembly.
Figure 38B:
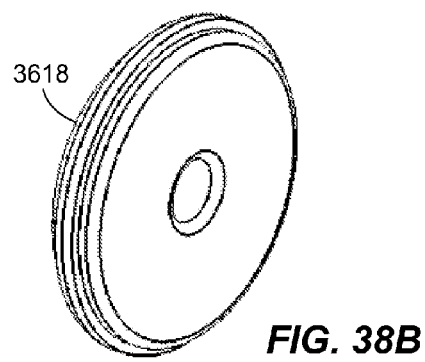

Referring back to FIGS. 37A and 37B, the nose portion 3618 grasps a cannula tip 3721 of the cannula 3620 and seals the cannula 3620 from releasing the syringe payload into the marking material contained in the cone body 3614 (and vice versa). The nose portion 3618 is supported by both the inner spine 3616 of the cone body 3614 and the spiral element 3722 as well as the cannula 3620. The spiral element 3722 provides lateral strength to the cone body 3614 and allows the inner spine 3616 to reach full extension. The spiral element 3722 may extend beyond the cannula tip 3721 of the cannula 3620 and therefore may push the nose portion 3618 to a position seated in front of the cannula tip 3721 of the cannula 3620. As the RTS 3600 hits a target, the spiral element 3722 compresses and exposes the cannula tip 3721 of the cannula 3620, allowing the cannula 3620 to puncture the nose portion 3618, pierce the target, and the combination of kinetic energy and the pressure means 3612 acting on the piston 3609 causes the purging the syringe payload. Once the RTS 3600 has fallen off the target to the ground, in the air, or into or onto water, the spiral element 3722 returns to its original, unbiased position, pushing the nose portion 3618 back to the position in which it is seated in front of the cannula tip 3721, thereby covering the cannula tip 3721 of the cannula 3620. Additionally, the bursting of the cone body 3614 may reduce resistance against the cannula 3620, facilitating movement of the cannula 3620 toward and into contact with the target.

Figure 39A:
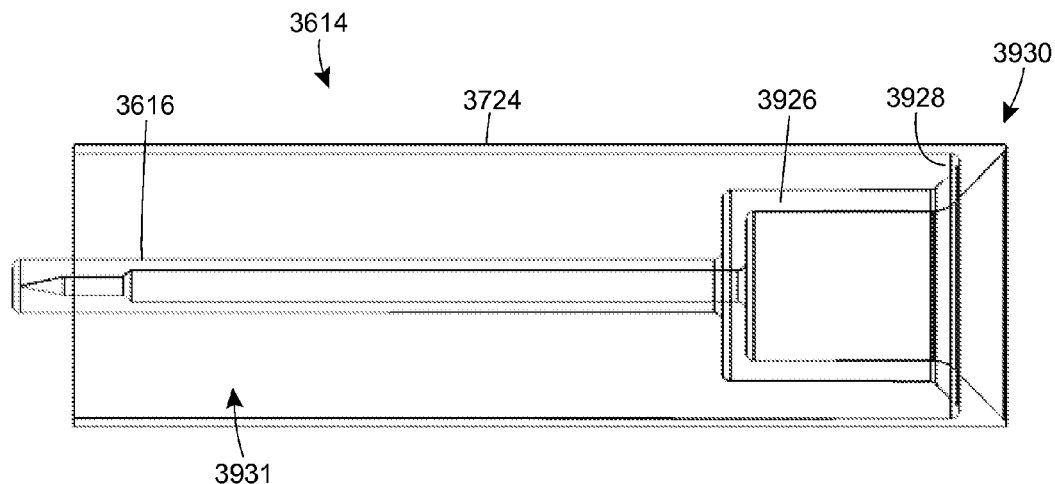
FIGS. 39A and 39B are various cross-sectional views of a cone body of the cone assembly.
Figure 39B:
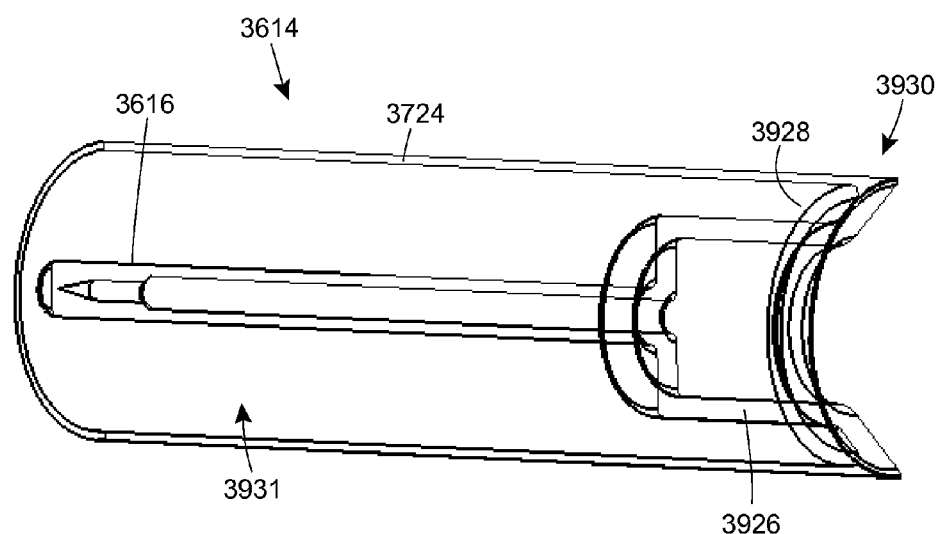

Turning to FIGS. 39A and 39B, the cone body 3614 of the cone assembly 3602 includes the inner spine 3616, the body wall 3724, a base 3926, a spring seat 3928, and a cone payload space 3931. The inner spine 3616 substantially surrounds the cannula 3620 and provides the cone body 3614 with longitudinal strength. At a first end 3930 of the cone body 3614, the base 3926 provides a cylindrical bore sized to fit around an end of the syringe 3610 and a portion of the cannula 3620. Also, at the first end 3930 of the cone body 3614, the spring seat 3928 provides a biasing surface for the spiral element 3722 of the cone assembly 3602. Upon impact with the target, the inner spine 3616 of the cone body 3614 may collapse, whereas the body wall 3724 of the cone body 3614 may burst. The inner spine 3616 may support the nose portion 3618 as well as hold the ballistic profile of the cone assembly 3602 at firing and in-flight. To fit the cone assembly 3602, the cannula 3620 is first fit to the syringe 3610 and then the cone assembly 3602 slides over the cannula 3620 and is positioned such that the inner spine 3616 substantially surrounds the cannula 3620 and the base 3926 substantially surrounds an end of the cannula 3620 and a part of the syringe 3610.

Figure 40A:
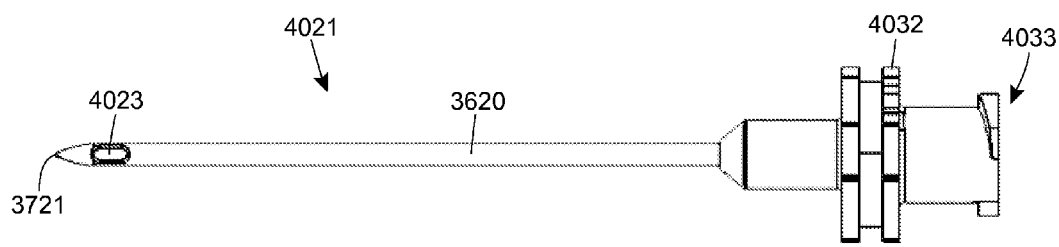
FIGS. 40A and 40B are various views of a cannula and cannula hub of the remote treatment system of FIGS. 36A and 36B.
Figure 40B:
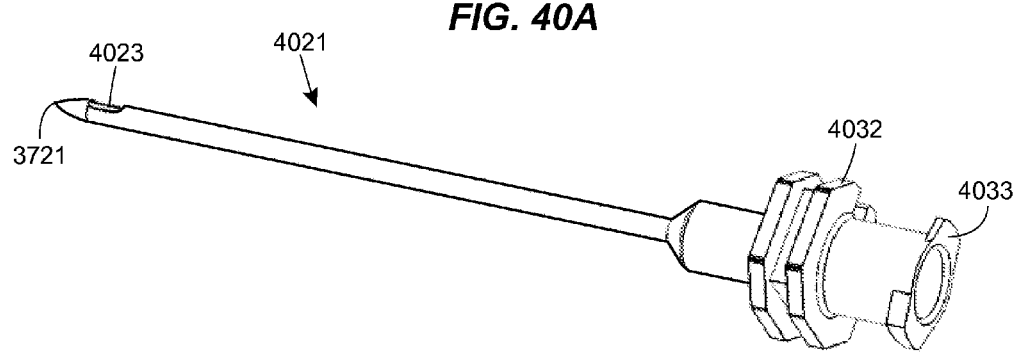
Figure 41:
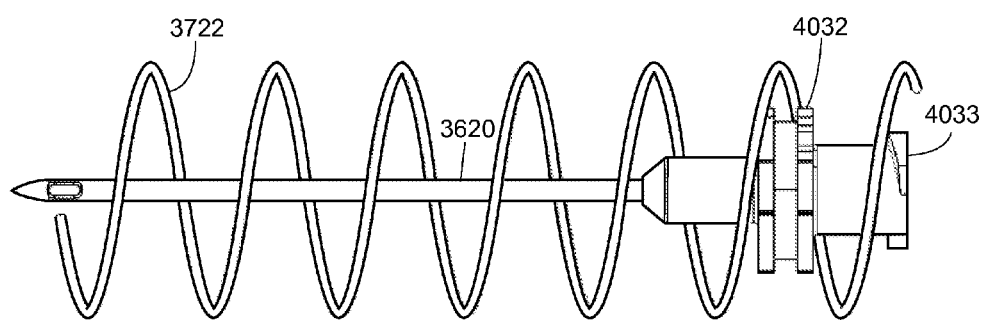
FIG. 41 is a side view of a spiral element of the cone assembly, the cannula, and the cannula hub of the cone assembly.

FIGS. 40A and 40B illustrates a cannula assembly 4021 including the cannula 3620, which may be a Sprotte type, a purge hole 4023 of the cannula 3620, and a cannula hub 4032. The cannula 3620 may, but need not, be a 16 gauge needle and approximately 40 mm long. The RTS 3600 may optionally include a biopsy tissue material sampling cannula, for example, an open fore-end Quincke type, and may be fitted without retooling the cone assembly 3602. The purge hole 4023 may be oval in shape. The cannula hub 4032 is fixed to the cannula 3620 at an end of the cannula 3620 opposite the cannula tip 3721. The cannula hub 4032 may provide a cannula coupler 4033, such as a luer-lock hub, that is designed to couple to a corresponding coupling mechanism of the syringe 3610, such as a luer-lock head. The luer-lock hub and the luer-lock head are conventional coupling mechanisms used in conventional syringes. FIG. 41 illustrates the spiral element 3722 disposed around the cannula 3620 and the cannula hub 4032 of the cannula assembly 4021.

The cone assembly 3602 performs multiple functions including protecting an operator while the RTS 3600 is loaded into the deployment mechanism, protecting the cannula tip 3721 of the cannula 3620 from external forces and contaminants, carrying the marking material, providing an effective ballistic profile, and covering the cannula 3620 after the RTS 3600 has fallen of the target, though it need not perform one or more of these functions.

FIGS. 42A-42D illustrate various views of the vanes cup 3604, which, as noted above, may spin-stabilize the RTS 3600 when the RTS 3600 is in flight. The vanes cup 3604 has a stabilization means 3605 in the form of a plurality of vanes 3605, a first end 4234, and a second end 4236. While not illustrated herein, a ventil (e.g., the ventil 1810, 2500) may be fitted to the vanes cup 3604. The vanes cup 3604 may have an inner diameter sized to receive an outer diameter of the syringe 3610. An outer diameter of each of the vanes 3605 may be sized to an inner diameter of a gun barrel, such that the vanes 3605, and more generally the vanes cup 3604, is in slight contact with the inner diameter of a bore of a slug-gun or shotgun to keep the RTS 3600 centered. In one embodiment, the vanes 3605 may be made of a flexible material that allows the vanes 3605 to accommodate the changing bore size of a barrel of a shotgun and slug-gun. The vanes 3605 may run the length of the vanes cup 3604, stopping short at the first end 4234 where the vanes cup 3604 connects to a bayonet assembly, a wad assembly, or another means of linking with a deployment mechanism, as described further below. In FIGS. 42A-42D, the vanes 3605 form concentric spirals. The first end 4234 of the vanes cup 3604 forms a cup opening 4235 that is configured to receive and couple to a corresponding locking mechanism of a deployment mechanism. In the illustrated embodiment, the cup opening 4235 is a conventional twist-lock female component that is adapted to lock to a corresponding twist-lock male head of a deployment mechanism, as will be discussed further below. The second end 4236 of the vanes cup 3604 mates with an end of the cone assembly 3602. The vanes cup 3604 may, but need not, be transparent so that an operator may view the contents of the syringe 3610 when the RTS 3600 is assembled. In one example, a logo may be displayed on the vanes cup 3604. The vanes cup 3604 and the syringe 3610 are, in some cases, manufactured separately and may either be sonic-welded, press-fitted, glued together, or attached by other fixing methods. Further, the vanes cup 3604 may include a small hole (not shown) that allows air to pass through the deployment mechanism and out the hole in the vanes cup 3604 so that a vacuum is not created behind the piston assembly 3608, which would prevent the piston 3609 from purging the syringe 3610.

Figure 43:
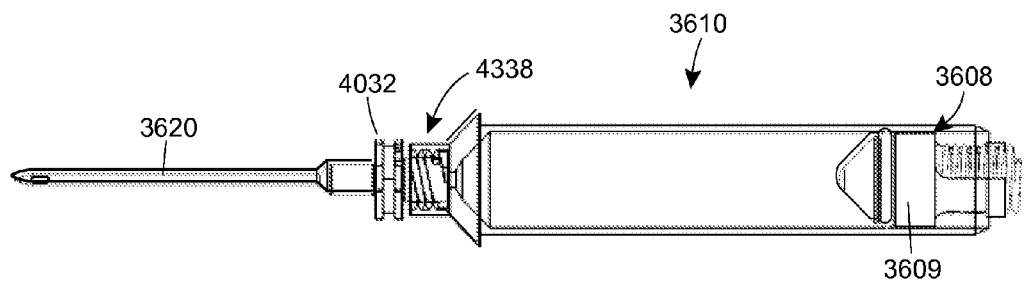
FIG. 43 is a side view illustrating the cannula of FIGS. 40A and 40B affixed to the syringe and the piston assembly.
Figure 44A:
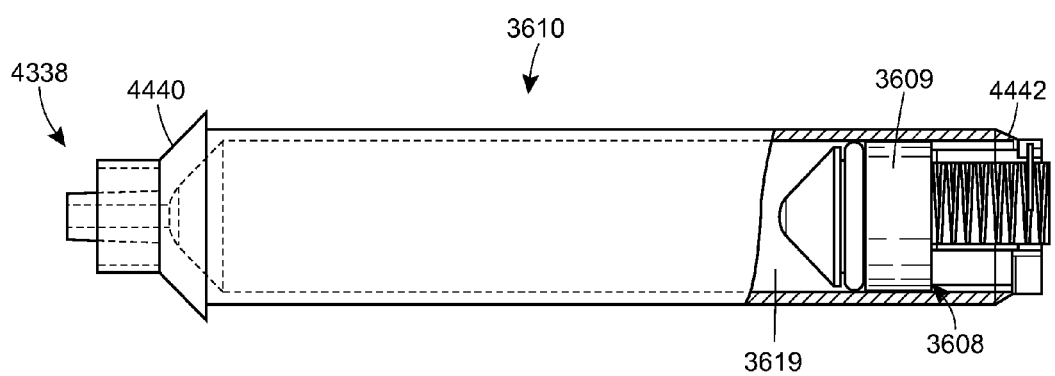
FIGS. 44A and 44B are various views of the syringe.
Figure 44B:
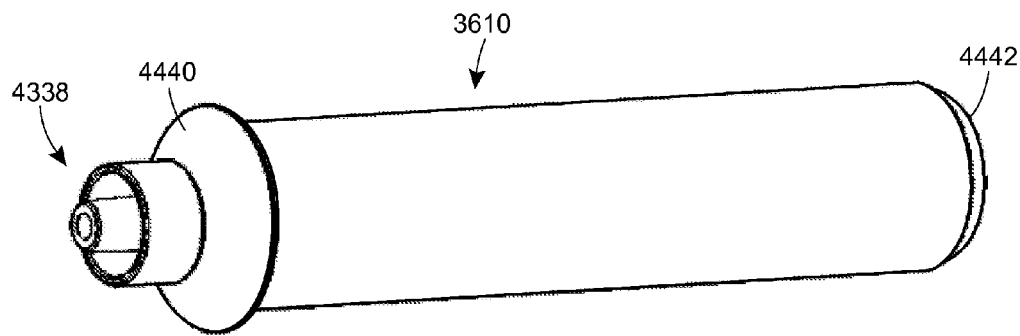

FIG. 43 illustrates the cannula 3620 coupled to and in fluid communication with the syringe 3610. The cannula hub 4032 couples to a first end 4338 of the syringe 3610. In this example, the first end 4338 provides a luer-lock head adapted to receive the luer-lock cannula hub 4032 of the cannula 3620. FIG. 44A illustrates the syringe 3610 coupled to the piston assembly 3608 cocked in a loaded and ready position and FIG. 44B illustrates the syringe 3610. The syringe 3610 includes a payload area 3619, which holds the syringe payload to be dispensed by the RTS 3600, and a collar 4440 at the first end 4338. The piston assembly 3608 is disposed within the syringe 3610 at a tapered end 4442 of the syringe 3610 when in the loaded position. The tapered end 4442 of the syringe 3610 is tapered having a sharp angled edge that is configured to release the piston assembly 3608 when the piston 3609 is activated upon impact with the target. The collar 4440 may be conical in shape, where the first end 4338 of the syringe 3610 mates with the first end 3930 of the cone body 3614 of the cone assembly 3602. The collar 4440 provides a surface for mating with a corresponding surface of the cone assembly 3602, while the foundation of the collar 4440 abuts the vanes cup 3604.

FIGS. 45A, 45B, 46A, and 46B illustrate the piston assembly 3608 and pressure means 3612 for use within the syringe 3610. The piston 3609 includes an inner end 4513 that is threaded to fit a similarly threaded tool bar (e.g., a T-shaped bar loading and cocking tool as described below) or other mechanism, as will be discussed below. Once the tool bar is threadedly coupled to the piston 3609, an operator may pull the piston assembly 3608 through the syringe 3610, and thereby through the vanes cup 3604, until the piston assembly 3608 reaches the loaded position, in order to pull a syringe payload into the payload area 3619 through the first end 4338. By pulling the piston 3609 through the syringe 3610, the piston 3609 provides a compressive force to the pressure means 3612 until one or more firing fingers 4544 (e.g., two or more firing fingers) disposed at a first end 4553 of the piston 3609 engages the tapered end 4442 of the syringe 3610 in the loaded position. Each firing finger 4544 has an outwardly extending tab 4546 configured to engage the sharped angle edge of the tapered end 4442. The firing fingers 4544 hold the piston 3609 in place so there is no force from the pressure means 3612 pushing the syringe payload through the syringe 3610 along the cannula 3620 and out the cannula tip 3721. While FIGS. 45-46 illustrate the piston 3609 having two firing fingers 4544, the piston 3609 may, in other examples, include additional firing fingers 4544 for added stability, one firing finger, or the piston 3609 may not have any firing fingers. An expander ring 4647 may sit in a groove 4548 formed in an inner surface of each of the firing fingers 4544. The expander ring 4647 may exert a radial force on the firing fingers 4544 to ensure that the extending tabs 4546 continue to engage the sharp edge of the tapered end 4442 of the syringe 3610. The expander ring 4647 pushes the firing fingers 4544 beyond a diameter of the syringe 3610 so that the extending tabs 4546 couple (e.g., are secured) to the tapered end 4442 of the syringe 3610. The extending tabs 4546 of the firing fingers 4544 are configured to be clipped off from the firing fingers 4544 by the sharp tapered end 4442 of the syringe 3610 upon impact with the target, allowing the piston assembly 3608 to be released and travel forward through the syringe 3610.

Each extending tab 4546 may include a notch 4549 located at the first end 4553, which allows the extending tab 4546 to flex outwardly when being removed (e.g., clipped off) by tapered end 4442. The deployment mechanism may have a wad rod or a bayonet rod (see reference numbers 5618 and 4906 described below) that exerts a force on the piston 3609 in addition to the kinetic energy of the impact, which causes the tapered end 4442 of the syringe 3610 to slice through the extending tabs 4546 of the firing fingers 4544. The piston 3609 is forced through the syringe 3610, purging the payload area 3619, out the purge hole 4023 of the cannula 3620, and onto or into the target. The piston assembly 3608 also comprises a sealing element 4650, e.g., an O-ring that seals the syringe payload from the pressure means 3612. The sealing element 4650 is disposed inside a channel 4552 formed in a second end 4554 of the piston 3609 opposite the first end 4553. In another embodiment instead of piston disclosed herein, a piston may be manufactured in a multi-pass molding process and the function of sealing would be performed by one or more rubbery elements of a coating over the piston. The sealing element 4650 in this example is configured to provide a seal between the payload area 3619 of the syringe 3610 and the "dry" area of the piston assembly 3608 and is also configured to keep the payload in the syringe 3610 away from the pressure means 3612. To facilitate purging of the payload, the sealing element 4650 and an inner surface of the syringe 3610 may be specifically shaped and formed or made of a material or materials or include an additive that facilitates gliding of the sealing element 4650 and the piston 3609 through the syringe 3610. The piston assembly 3608 may provide more than one sealing element 4650, or alternatively, the piston 3609 may be manufactured to include an FDA approved resin or polymer rubber-like coating with one or more features that function as an O-ring. In one example, the syringe 3610 may be made of a resin that includes or be coated with a lubed resin, such as BASF's "white oil" lubricant, that decreases friction between the syringe 3610 and the piston 3609.

It will be appreciated that the piston 3609 and the sealing element 4650 are each made of an FDA approved resin or polymer because they both come into contact with the syringe payload. The firing fingers 4544 may be made of a flexible material so that the firing fingers 4544 flex from a first position when the extending tabs 4546 engage the tapered end 4442 of the syringe 3610 to a second position after the extending tabs 4546 have been removed and the piston 3609 slides within the syringe 3610. Because the firing fingers 4544 are removed when the RTS 3600 makes contact with the target, the RTS 3600 may only be used a single time. However, in some cases, the firing fingers 4544 or piston assembly 3608 may be replaced so that the RTS 3600 may be used more than once. In another embodiment, the piston may not include firing fingers and the extending tabs may be in a different location than is depicted. In one example, the pressure means 3612 may be a spring sized to fit the dimensions of the syringe 3610. In the case where an extended syringe 3610 is required, the pressure means 3612 may be sized according to the specifications of the syringe 3610 without compromising the appropriate dynamic characteristics required for releasing the piston assembly 3608.

Figure 47A:
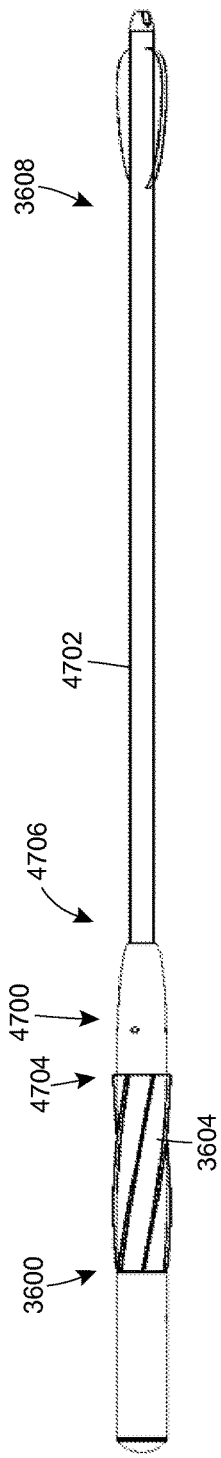
FIGS. 47A and 47B are various views of the remote treatment system coupled to one example of a deployment mechanism.
Figure 47B:
Figure 48:
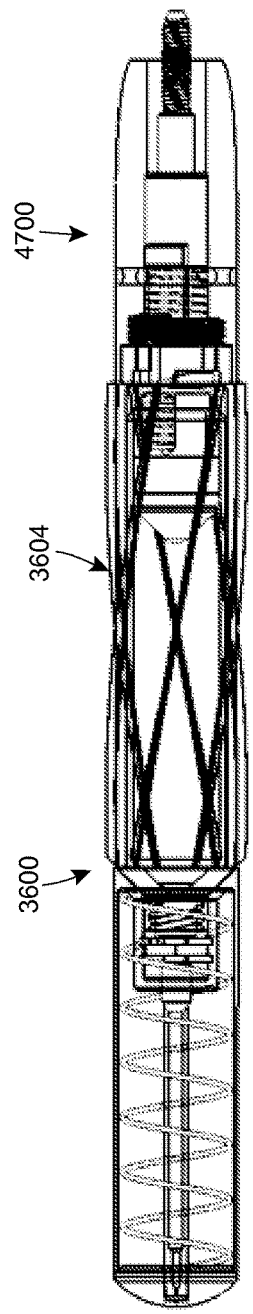
FIG. 48 is a cross-sectional view of the remote treatment system coupled to a bow bayonet assembly of the deployment mechanism.

FIGS. 47A, 47B, and 48 illustrate various views of the RTS 3600 coupled to one example of a deployment mechanism that can be used to deploy the RTS 3600. In this example, the deployment mechanism takes the form of a bow bayonet assembly 4700 and a tip-less shaft 4702, such as a crossbow bolt or longbow arrow. The bayonet assembly 4700 is connected to the RTS 3600, more specifically the vanes cup 3604, at a first end 4704 and is threadedly coupled to an end of the shaft 4702 at a second end 4706. In other examples, the shaft 4702 can be replaced with a jab stick with a threaded end, spear, javelin, or other apparatus that can be thrown by hand for close-target acquisition or projected by a crossbow or a longbow. The bayonet assembly 4700, once coupled to the RTS 3600, exerts a force onto to the piston assembly 3608 of the RTS 3600 to expel the syringe payload.

FIGS. 48 and 49A-C illustrate additional views of the bayonet assembly 4700. As best illustrated in FIG. 49A, the bayonet assembly 4700 has an outer body 4908, a bayonet rod 4906 slidably disposed within the outer body 4908 and disposed within a central portion of the piston assembly 3608, an anchor 4910 threaded into the outer body 4908, and a bayonet coil 4912 disposed between the anchor 4910 and a middle portion 4916 of the bayonet rod 4906. The bayonet rod 4906 has a first end 4902 and a second end 4904 opposite the first end 4902. A first end 4902 of the bayonet rod 4906 is profiled and provides a force to the inner end 4513 of the piston 3609 to assist in releasing the piston assembly 3608 when the RTS 3600 contacts the target. The first end 4902 includes a plurality of bayonet rod slots 4913 that facilitate air travel through the bayonet assembly 4700 and through the cup opening 4235 in the first end 4234 of the vanes cup 3604 to prevent a vacuum from forming in the "dry area" behind the piston 3609, which would otherwise stop the piston 3609 from purging the syringe payload. The rod slots 4913 may be a single filed edge, or may be a plurality of slots having a different shape than the slots 4913 depicted in FIG. 49A-C. The second end 4904 of the bayonet rod 4906 provides bayonet rod threads 4914 that are adapted to threadedly couple to internal threads of the shaft 4702 or other means of facilitating projection. The bayonet rod threads 4914 of the second end 4904 of the bayonet rod 4906 may be in a range of approximately 3 mm to 4 mm in diameter. At the second end 4706 of the bayonet assembly 4700, the outer body 4908 extends a distance to cover the fore-end of the shaft 4702, to steady the bayonet assembly 4700, and to limit latitudinal stress to the connection between the bayonet assembly 4700 and the shaft 4702 by forming a firm but easily working fit between the shaft 4702 and the inside surface of the second end 4706 of the outer body 4908. Although the bayonet rod 4906 is free to slide within the outer body 4908, the bayonet assembly 4700 is configured to keep the bayonet rod 4906 from spinning within the outer body 4908 of the bayonet assembly 4700. The outer body 4908 of the bayonet assembly 4700 may be brightly colored to aid in its recovery. Additionally, a programmable RFID or SIM tag may be located inside the outer body 4908 so that an operator may track the bayonet assembly 4700 and RTS 3600 after it has been deployed and/or to gather data on the activity and use of each bayonet assembly 4700. A smartphone application as described above, will allow an operator to communicate with and track the bayonet assembly 4700 via the RFID or SIM tag. The outer body 4908 may display a logo.

Figure 50:
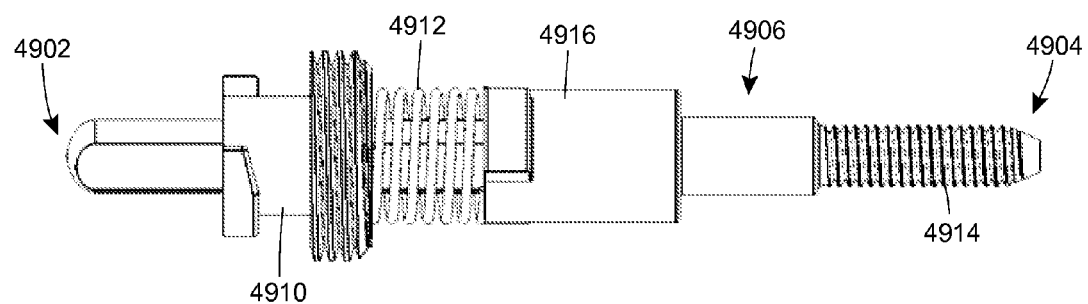
FIG. 50 is a side view of a bayonet rod, an anchor, and a bayonet coil of the bayonet assembly.
Figure 51:
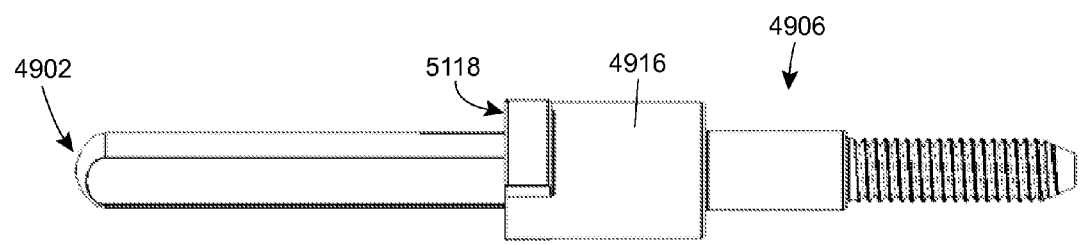
FIG. 51 is a side view of the bayonet rod of the bayonet assembly.

FIGS. 50, 51, 52A, 52B, and 53 illustrate the bayonet rod 4906, the anchor 4910, and the bayonet coil 4912 of the bayonet assembly 4700 in greater detail. As illustrated in FIG. 50, the bayonet coil 4912 is disposed between the anchor 4910 and a middle portion 4916 of the bayonet rod 4906. As best illustrated in FIG. 51, the middle portion 4916 is disposed between the first end 4902 and second end 4904 and provides a seat 5118 for the bayonet coil 4912, allowing the bayonet coil 4912 to bias the first end 4902 of the bayonet rod 4906 away from the piston assembly 3608 to avoid accidental discharge of the syringe payload in the syringe 3610. The bayonet rod 4906 may be made of a material, such as brass, two-part resin, or a solid urethane resin. As illustrated in FIGS. 52A and 52B, the anchor 4910 of the bayonet assembly 4700 has a bayonet coupler 5220 and anchor threads 5222. The bayonet coupler 5220 may be a twist-lock mechanism that is adapted to couple to the cup opening 4235 of the first end 4234 of the vanes cup 3604 of the RTS 3600. The threads 5222 are adapted to threadedly couple the anchor 4910 to the outer body 4908 of the bayonet assembly 4700. An anchor bore 5224 is formed within the anchor 4910 and is sized to receive the first end 4902 of the bayonet rod 4906. Once the RTS 3600 is deployed, the shaft 4702 and the bayonet assembly 4700 may be recovered and reused by de-coupling the RTS 3600 from the bayonet assembly 4700, and more particularly, by de-coupling the coupler 5220 of the anchor 4910 from the vanes cup 3604. While the anchor 4910 is illustrated as component separate from the outer body 4908, the anchor 4910 may be formed together with the outer body 4908 as an integrated component. Finally, as illustrated in FIG. 53, the bayonet coil 4912 of the bayonet assembly 4700 is disposed between the anchor 4910 and the coil seat 5118 and biases the bayonet rod 4906 away from the piston 3609. The bayonet coil 4912 may be strong enough to bias the first end 4902 of the bayonet rod 4906 away from the piston assembly 3608 while the RTS 3600 is being transported over rough terrain or as the operator is attaching RTS 3600 to the shaft 4702 or a stick or throwing deployment device.

Figure 54A:
FIGS. 54A and 54B are various views of the remote treatment system coupled to another example of a deployment mechanism.
Figure 54B:
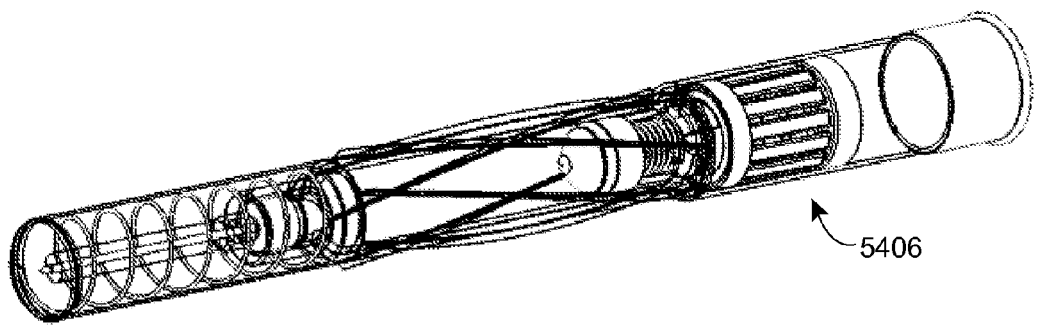
Figure 54C:
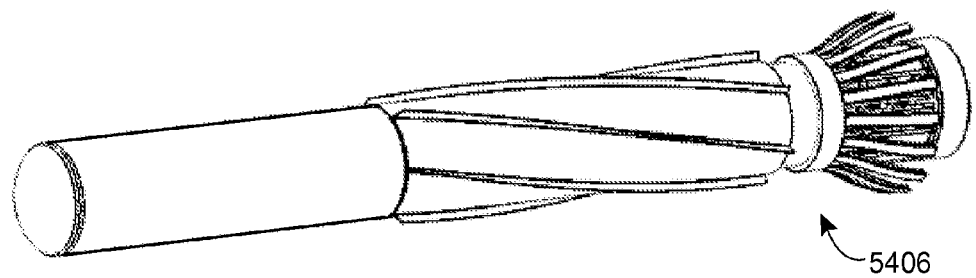
FIG. 54C is a perspective view showing the remote treatment system of FIGS. 54A and 54B "in-flight;"

FIGS. 54A-54C provide various views of the RTS 3600 coupled to a second example of a deployment mechanism. In the illustrated embodiment, the deployment mechanism takes the form of a shell assembly 5400, e.g., a twelve gauge shotgun shell, a shotgun shell of another caliber, or a shotgun shell-like device, which can be deployed by a shotgun or a slug-gun (e.g., a twelve gauge or other size). A wad assembly 5406 is housed within the shell assembly 5400, as will be discussed in greater detail below. FIGS. 54A and 54B illustrate the RTS 3600 and the second example of the deployment mechanism prior to usage. FIG. 54C illustrates the RTS 3600 in flight, soon after being deployed (e.g., from a slug-gun or a shotgun).

Figure 55A:
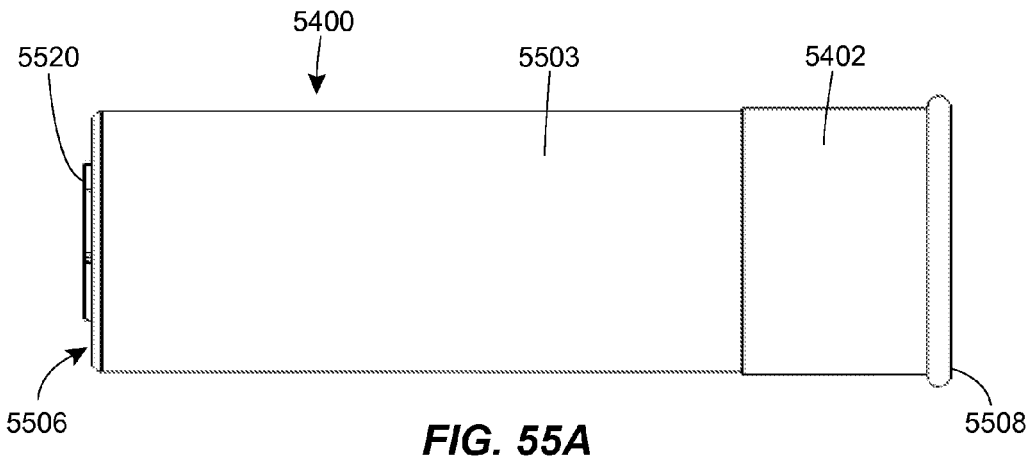
FIGS. 55A, 55B, and 55C are various side views of a shell wad assembly disposed within a shotgun or slug-gun shell and a shell hull of the deployment mechanism of FIGS. 54A-54C.
Figure 55B:
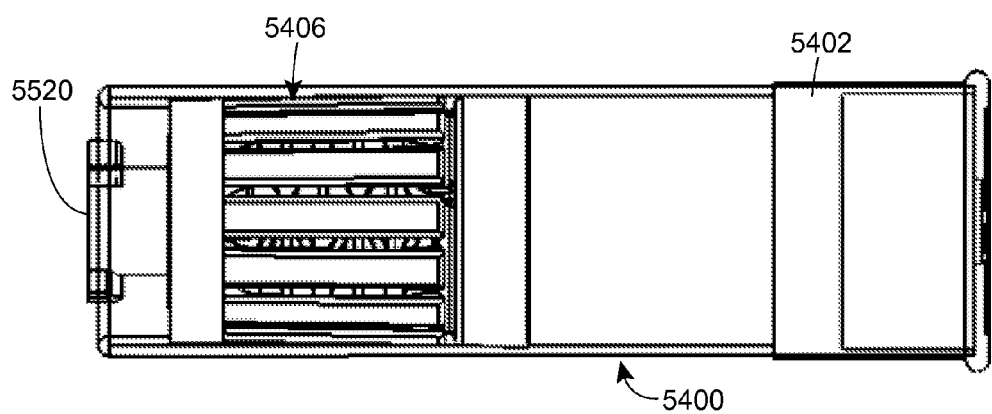
Figure 55C:
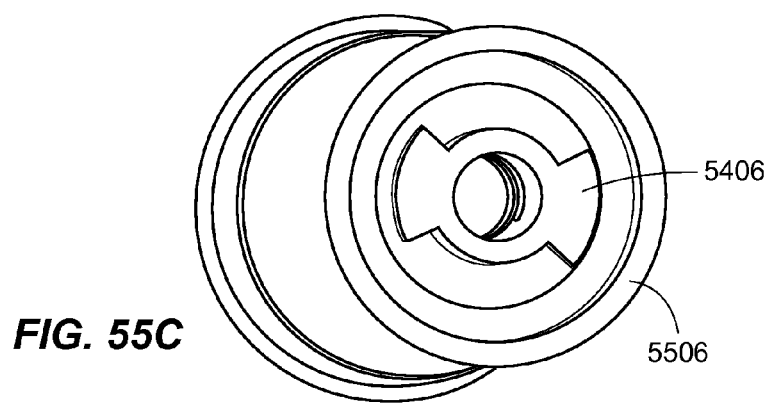

FIGS. 55A, 55B and 55C illustrate various views of the shell assembly 5400, a head 5402, a hull 5503, and a rim 5508 at a rear-end of the head 5402. The shell assembly 5400 may include shortened or lengthened hulls 5503 and full or half-head length heads 5402 for twelve gauge or similar shotgun shells with various gunpowder charges. In some embodiments, the shell assembly 5400 includes a crimp, such as a roll crimp 5506. The RTS 3600 is sized to fit the inner diameter of the hull 5503. For example, the shell assembly 5400 may be what is known as a 2¾ inch shotgun shell. The hull 5503 shown in FIG. 55C has a type of roll crimp 5506 at a first end 5520 of the wad assembly 5406, but another crimp may be used or feature no crimp. The hull 5503 may be color coded and labeled to signify the distance that that particular powder load is estimated distance the RTS 3600 will travel. The rear-end of the head 5402 may also be branded to display head stamp letters, numerals and a shape.

Figure 56A:
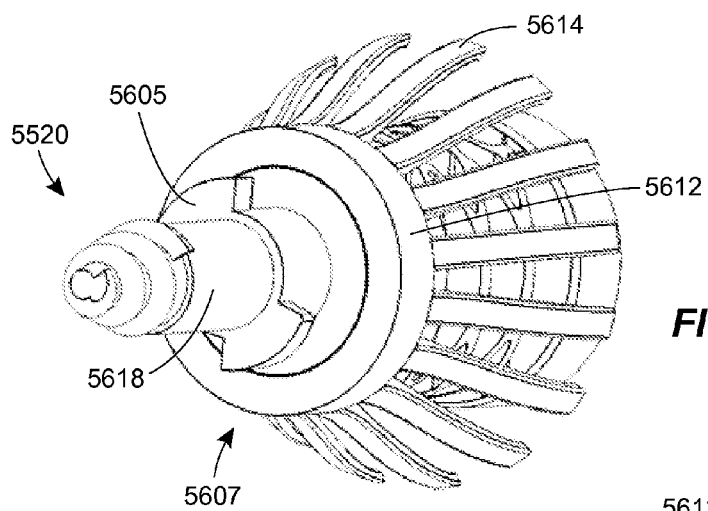
FIGS. 56A, 56B, and 56C are various views of the shell wad assembly of FIGS. 55A-55C "in-flight;"
Figure 56B:
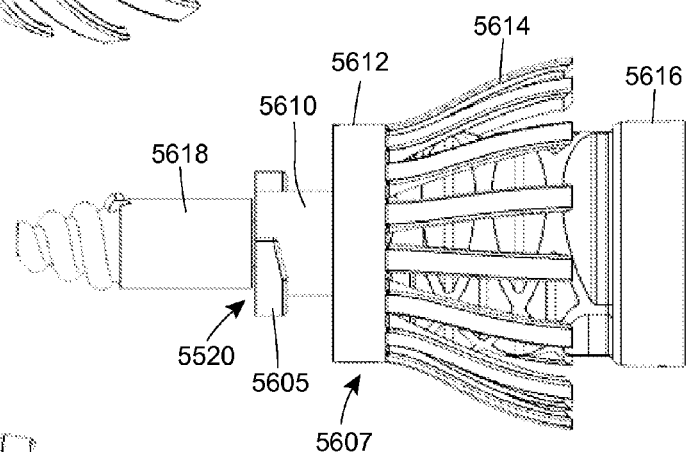
Figure 56C:
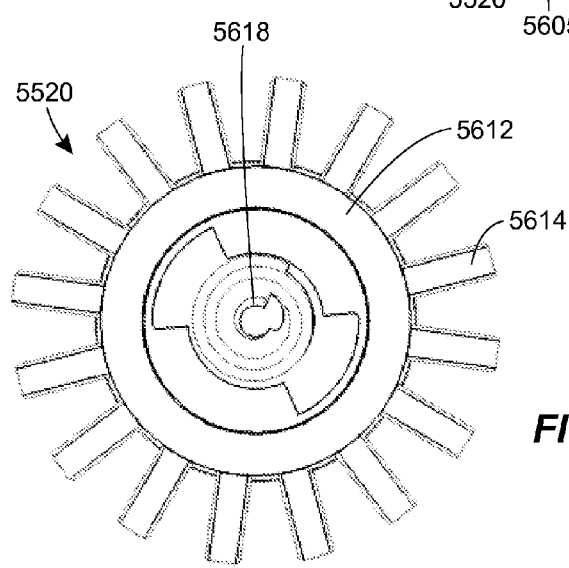

As illustrated in FIGS. 56A, 56B, 56C, 57A, 57B, 58A, 58B, 59A, and 59B, the wad assembly 5406 comprises a wad coupler 5605, wad legs 5808, and a wad cup 5616. Attached to the wad assembly 5406 is a drogue assembly 5607 comprising a belt 5612 and a plurality of flights 5614. The belt 5612 fits onto the wad 5610 between the first end 5520 of the wad assembly 5406 and the wad legs 5808, the connection being fixed by sonic welding, glue or another process. The wad assembly 5406 and the drogue assembly 5607 may be made as a single part. The wad cup 5616 of the wad 5610 is adapted to contact an inner surface of the hull 5503 and bore of a gun. The wad legs 5808 are generally configured to compress when the gunpowder burns upon firing and to compress upon impact with the target, acting as a compressing shock absorber and expander, such that a wad rod 5618 pushes the first end 4553 of the piston 3609, helping to remove the extending tabs 4546. The wad assembly 5406 is disposed within the shell assembly 5400 and the first end 5520 is twist-fitted, or connected by other means, to the cup opening 4235 of the vanes cup 3604, as illustrated in FIGS. 53-54. The first end 5520 protrudes slightly beyond the roll crimp 5506 of the hull 5503 in order to connect the wad assembly 5406 to the vanes cup 3604 of the RTS 3600. FIGS. 56A, 56B, and 56C illustrate the wad assembly 5406 when the RTS 3600 has been deployed, which causes the plurality of flights 5614 to flare out. FIGS. 57A and 57B illustrate the wad assembly 5406 when disposed within the shell assembly 5400. In this position, the plurality of flights 5614 of the belt 5612 is compressed against the wad legs 5808. FIGS. 58A and 58B illustrate the wad 5610 without the drogue assembly 5607, and the drogue assembly 5607 with its belt 5612 and plurality of flights 5614 is illustrated alone in FIGS. 59A and 59B.

The wad rod 5618 of the wad assembly 5406 is illustrated in FIG. 60. The wad rod 5618 is disposed in a central bore of the wad 5610 and is free to move within the central bore of the wad 5610. So positioned, the wad rod 5618 is threadedly attached to the piston 3609 and configured to exert a force against the inner end 4513 of the piston 3609. For example, upon impact with the target, the wad legs 5808 compresses at the first end 5520, forcing the wad rod 5618 against the inner end 4513 of the piston 3609, assisting in the releasing of the piston assembly 3608, and purging the syringe 3610 of the syringe payload into or onto the target. At a first end 6002, the wad rod 5618 is threaded, allowing an operator to threadedly couple the first end 6002 to the threaded inner end 4513 of the piston 3609. Premature firing of the piston assembly 3608 may be prevented by threading the first end 6002 of the wad rod 5618 to the piston 3609. At an opposite end, the wad rod 5618 has one or more filed edges that create slots 6004 similar in structure to the bayonet rod slot (or slots) 4913 of the bayonet rod 4906. The wad rod slots 6004 allow air to flow through the wad assembly 5406 to prevent a vacuum from forming behind the piston 3609. The wad rod 5618 and the wad 5610 may undergo testing in order to determine the dimensions of both the wad rod 5618 and the wad 5610 so that when an operator squeezes the trigger of the deployment mechanism, the wad rod 5618 does not break the extending tabs 4546, activating the piston assembly 3608 and prematurely purging the syringe 3610. The wad rod 5618 may be made of a dense and heavy resin or similar material. In another embodiment, the wad 5610 may be formed together with the drogue assembly 5607 as one component. The second example of the deployment mechanism may include gunpowder of a specific composition to meet the needs of the RTS 3600. The gunpowder provided may create a minimal, or soft burn to limit the risk of damage to the RTS 3600. In a preferred embodiment, the gunpowder will be non-toxic to avoid negative environmental impact. The gunpowder composition will change according to the desired distance of travel of the RTS 3600. For example, different gunpowder compositions may accommodate a travel distance in the ranges of 10-25 yards, 20-45 yards, 40-65 yards, and 60-100 yards. Additionally, the gunpowder composition may provide a 900 feet per second or less muzzle velocity, which is commonly used for being under the transonic zone, i.e. the velocity limit required to suppress the sound of the projectile's supersonic "crack" sound in flight. The gunpowder may also achieve a 100 feet per second velocity when the RTS 3600 impacts the target. Another embodiment of the deployment mechanism may utilize gas or air pressure instead of gunpowder.

A number of accessories may be used with any of the remote treatment systems (e.g., the RTS 3600 disclosed herein. A tool bar 6100, as illustrated in FIG. 61, is used to fill the syringe 3610 with a syringe payload. The tool bar 6100 includes a handle 6102 at a first end 6106 and a threaded bar tip 6104 at a second end 6107. The threaded bar tip 6104 is configured to threadedly couple to the inner end 4513 of the piston 3609. FIGS. 62A and 62B illustrate various views of a safety pin 6200 that is configured for use with the vanes cup 3100, 3604 but can be used with other vanes-type cups. The safety pin 6200 is configured to prevent premature purging of the syringe 3610. The safety pin 6200 may include a ring 6202 having a round finger hole 6204 and two flexible arms 6206. The flexible arms 6206 form a partial circle 6208 and flare out slightly at pin ends 6209. The flexible arms 6206 have a diameter that is slightly smaller than an inner diameter of the vanes cup (e.g., the vanes cup 3100). At a point before the flexible arms 6206 flare out, an inner surface 6210 of each of the flexible arms 6206 is adapted to cover first and second holes in the vanes cup 3604 (see FIGS. 31A and 31B). Through holes or a space in the vanes cup 3604, the safety clip 6200 may engage an outer surface of the tapered end 4442 of the syringe 3610 and prevents the extending tabs 4546 of the each firing finger 4544 of the piston 3609 from being removed. Effectively, the safety pin 6200 prevents the piston 3609 from moving through the syringe 3610 and expelling the syringe payload. The safety pin 6200 is useful, for example, if a shipment of RTSs 3600 filled with syringe payload is transported over rocky terrain where accidental discharge of the piston assembly 3608 may occur.

Figure 63A:
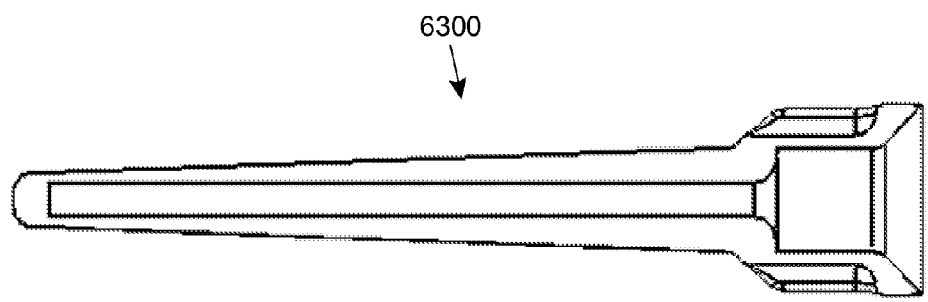
FIGS. 63A and 63B are various views of a cannula shield.
Figure 63B:
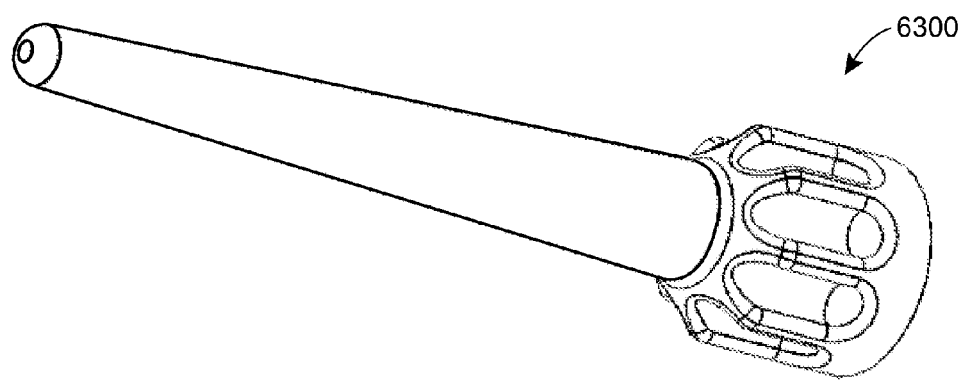
Figure 64A:
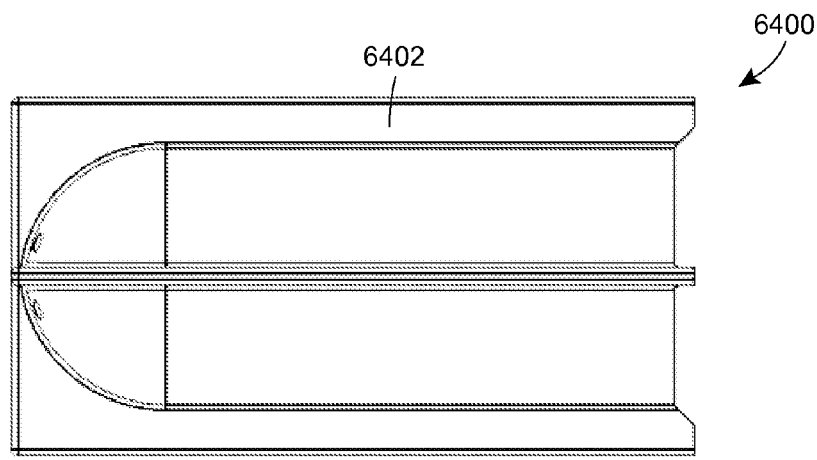
FIGS. 64 A and 64B are various views of an embodiment of a cone grip.
FIGS. 64C and 64D are various views of another embodiment of a cone grip.
Figure 64B:
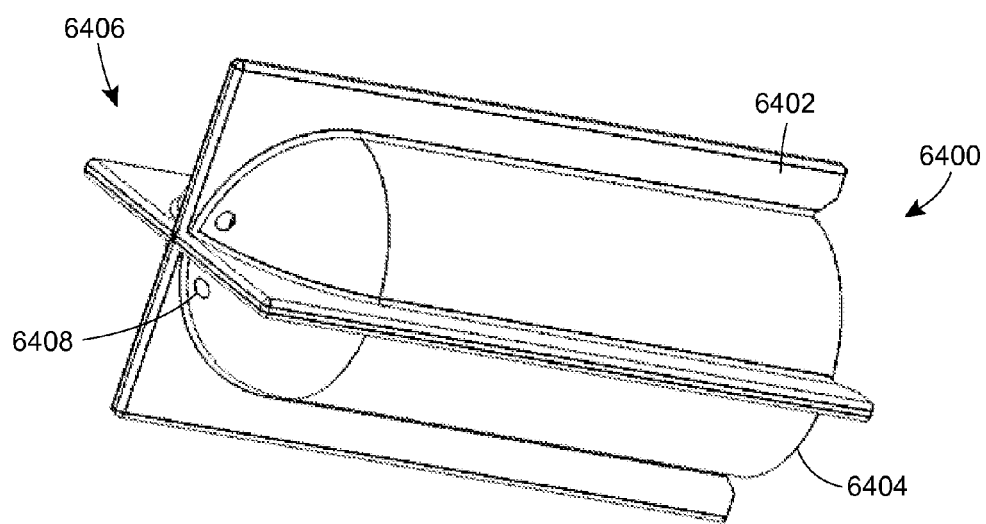
Figure 64C:
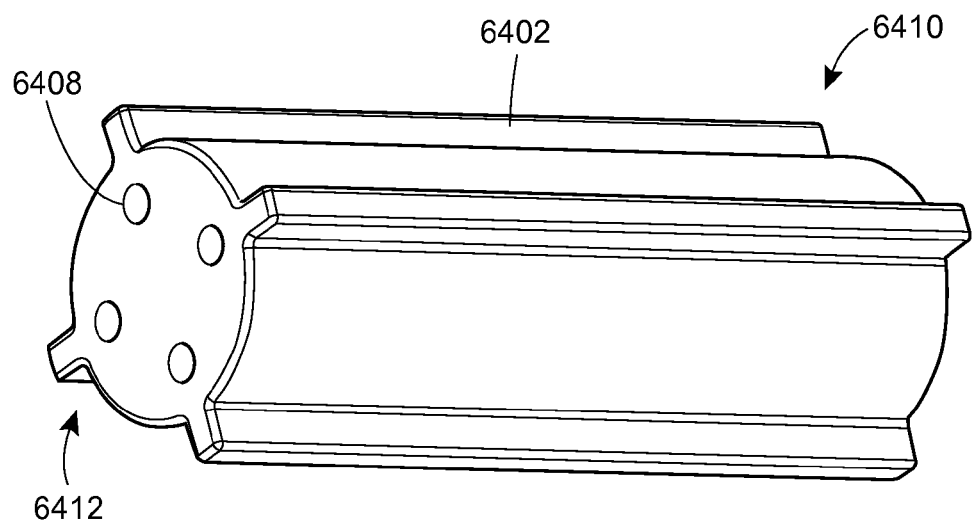
Figure 64D:

FIGS. 63A and 63B illustrate a shield 6300 that may be used to cover the cannula 3620 before the cone assembly 3602 is fitted to the syringe 3610. The shield 6300 protects the cannula assembly 4021 and the cannula tip 3721 of the cannula 3620 from disinfectants and/or damage and may cover the cannula 3620 until an operator is ready to fit the cone assembly 3602 to the syringe 3610. A protective dome grip 6400, illustrated in FIGS. 64A and 64B, provides a hard, external body for the cone assembly 3602 so that an operator may handle the RTS 3600 without bursting or rupturing the thin body wall 3724 of the cone body 3614. The dome grip 6400 keeps the cone body 3614, which is filled with the marking material, safe from rupture, and may provide an operator with the opportunity to assemble the RTS 3600, for example, when the operator arrives at the location where the RTS 3600 will be deployed. The dome grip 6400 provides a plurality of spars 6402 that allow the operator to easily hold the RTS 3600 while attaching the RTS 3600 to a deployment mechanism. The plurality of spars 6402 also provides the RTS 3600 with stability, allowing the cone assembly 3602 to stand upright before being attached to the syringe 3610. The spars 6402 also allow the RTS 3600 to stand upright after the syringe 3610 is filled, the piston assembly 3608 is cocked, the cannula assembly 4021 is fitted (optionally, and with or without the shield 6300), and the cone assembly 3602 is attached to the syringe 3610 over the first end 4338. At a first end 6404, the dome grip 6400 provides an opening so that during assembly, at manufacture, or for an operator, to slide the cone assembly 3602 into a cavity of the dome grip 6400. At a second end 6406 opposite the opening, the dome grip 6400 provides a plurality of vents 6408 to allow the cone assembly 3602 to slide down into the cavity. To facilitate transporting a plurality of RTSs 3600, a crate may provide an inside profile onto which the dome grip 6400 may stand, allowing an operator to fill the RTSs 3600 before transporting the RTSs 3600 to a different location. The dome grip 6400 may, in some cases, be transparent, so that the operator may still see the marking material contained in the payload space 3931 of the cone body 3614. The dome grip 6400 may display a logo. FIGS. 64C and 64D illustrate another embodiment of a flat grip 6410 having a flat second end 6412 to facilitate easier upright standing of RTS 3600.

It will be appreciated that the components that come into contact with the syringe payload, for example, the syringe 3610, the piston 3609, the sealing element 4650, the cannula hub 4032, and the nose portion 3618, are, at least in this example, made from an FDA approved material. The cone body 3614 and the shield 6300 may also be made from an FDA approved material. In one embodiment, the components of the RTS 3600 are made of biodegradable materials. Additionally, a non-toxic gunpowder may be used by the second deployment mechanism to deploy the RTS 3600.

The RTS 3600 may be customized where each component is selected and assembled by an operator. Customization provides an operator with the opportunity to design an RTS 3600 that best suits the operator's purpose. For example, a RTS 3600 may be customized for marking or tagging purposes only. In this case, the operator would assemble the RTS 3600 without a cannula 3620, or a syringe 3610 filled with a syringe payload. Instead, the operator would choose a cone assembly 3602 loaded with a desired marking material or tracking tag, fit the cone assembly 3602 onto a syringe 3610, and attach the customized RTS 3600 to a preferred deployment mechanism. Other examples include selecting a cone body 3614 without a marking material, a cone body 3614 having a particular marking material, a cannula for taking tissue samples, a cannula for a target having a tough surface or thick hide, a cannula for a target having a delicate surface or thin hide, etc.

The above-described embodiments are given for describing rather than limiting the scope of the invention, and modifications and variations may be resorted to without departing from the spirit and scope of the invention as those skilled in the art readily understand. Such modifications and variations are considered to be within the scope of the invention and the appended claims. The protection scope of the invention is defined by the accompanying claims. In addition, any of the reference numerals in the claims should not be interpreted as a limitation to the claims. Use of the verb "comprise" and its conjugations does not exclude the presence of elements or steps other than those stated in a claim. The indefinite article "a" or "an" preceding an element or step does not exclude the presence of a plurality of such elements or steps.

What is claimed:

1. A remote treatment system, comprising:
   a cone assembly including a spine, a cone body at least partially surrounding the spine, and a nose portion supported by the spine;
   a syringe coupled to a portion of the cone assembly and adapted to store a payload for treating a target;
   a cannula in fluid communication with the syringe, the cannula being at least partially surrounded by the spine, and the cannula being seated behind the nose portion;
   a vanes cup having an inner diameter sized to receive an outer diameter of the syringe, the vanes cup including means for stabilizing the remote treatment system; and
   pressure means at least partially disposed within the vanes cup, the pressure means being configured to apply a pressure against the payload within the syringe in response to an impact between the cone assembly and the target, such that the payload is expressed from the syringe.

2. The remote treatment system of claim 1, wherein the nose portion is configured to seal the cone assembly.

3. The remote treatment system of claim 2, wherein the cone body further comprises a cylindrical wall adapted to carry a marking payload, the cylindrical wall being a thin material configured to rupture in response to the impact between the cone assembly and the target, thereby expelling the marking payload onto the target.

4. The remote treatment system of claim 3, wherein the nose portion has a color selected based on the marking payload carried by the cone body.

5. The remote treatment system of claim 1, wherein the syringe has a first end and a collar formed at the first end, wherein the collar mates with the cone assembly.

6. The remote treatment system of claim 1, wherein the vanes cup is a frame and the stabilizing means comprises a plurality of vanes formed on and extending outward from an outer surface of the frame.

7. The remote treatment system of claim 1, further comprising a piston movably disposed within the syringe and in communication with the pressure means, the pressure means configured to apply the pressure against the payload through the piston.

8. The remote treatment system of claim 7, further comprising a groove formed in an outer surface of the piston and a sealing element disposed within the groove, the sealing element being configured to provide a seal between the pressure means and the syringe and being configured to force the payload away from the pressure means.

9. The remote treatment system of claim 7, wherein the piston comprises one or more firing fingers, and wherein the syringe releasingly engages the one or more firing fingers to bias the pressure means away from applying the pressure against the payload.

10. The remote treatment system of claim 9, wherein each of the one or more firing fingers comprises a tab having an inner groove to hold an expander ring disposed therein, wherein the expander ring biases the tabs beyond a diameter of the syringe to couple the tabs to an end of the syringe.

11. The remote treatment system of claim 10, wherein the syringe is configured to remove the tabs of the firing fingers in response to the impact between the cone assembly and the target, thereby releasing the piston, such that the pressure means applies pressure against the payload within the syringe and the payload is expressed from the syringe.

12. The remote treatment system of claim 7, further comprising a bayonet coupled to the vanes cup.

13. The remote treatment system of claim 12, wherein the bayonet further comprises a body, a bayonet rod movably disposed in the body, an anchor threadedly coupled to the body and coupled to a portion of the vanes cup, and a biasing element arranged within the body and configured to bias the bayonet rod away from the piston.

14. The remote treatment system of claim 13, wherein the bayonet rod comprises a front end and a rear end, wherein the front end applies pressure against the piston in response to the impact between the cone assembly and the target, and the rear end comprises threads to threadedly couple the bayonet rod to a shaft.

15. A remote treatment system, comprising:
   a cone assembly including a spine and a cone body at least partially surrounding the spine;
   a syringe coupled to a portion of the cone assembly and adapted to store a payload for treating a target;
   a cannula in fluid communication with the syringe;
   a vanes cup having an inner diameter sized to receive an outer diameter of the syringe, the vanes cup including means for stabilizing the remote treatment system; and
   pressure means at least partially disposed within the vanes cup, the pressure means being configured to apply a pressure against the payload within the syringe in response to an impact between the cone assembly and the target, such that the payload is expressed from the syringe,
   wherein the cone body further comprises a nose portion supported by the spine, the nose portion being configured to seal the cone assembly, and
   wherein the cone assembly further comprises a spiral element surrounding the spine, the cone body surrounding the spiral element, and the spiral element being configured to engage the nose portion.

16. The remote treatment system of claim 15, wherein the cannula is at least partially surrounded by the spiral element, wherein the cannula and is grasped by the nose portion, and the cannula is configured to pierce the nose portion of the cone assembly and express the payload from the syringe onto or into the target in response to the impact between the cone assembly and the target.

17. The remote treatment system of claim 16, wherein the spiral element compresses and carries the nose portion away from the syringe in response to the impact between the cone assembly and the target.

18. A remote treatment system, comprising:
   a cone assembly including a spine and a cone body at least partially surrounding the spine;
   a syringe coupled to a portion of the cone assembly and adapted to store a payload for treating a target;
   a cannula in fluid communication with the syringe;
   a vanes cup having an inner diameter sized to receive an outer diameter of the syringe, the vanes cup including means for stabilizing the remote treatment system;
   pressure means at least partially disposed within the vanes CUP, the pressure means being configured to apply a pressure against the payload within the syringe in response to an impact between the cone assembly and the target, such that the payload is expressed from the syringe; and
   a wad coupled to the vanes cup, the wad comprising a plurality of compression legs and an outer surface adapted to contact an inner surface of a shell.

19. The remote treatment system of claim 1, further comprising a safety clip coupled to the vanes cup and engaged with the syringe to prevent the payload from being expressed.

20. The remote treatment system of claim 1, wherein the pressure means comprises at least one of a pressurized fluid and a spring.

* * * * *